United States Patent
Andersen et al.

(10) Patent No.: US 11,384,347 B2
(45) Date of Patent: Jul. 12, 2022

(54) ALPHA-AMYLASE VARIANTS AND POLYNUCLEOTIDES ENCODING SAME

(71) Applicant: NOVOZYMES A/S, Bagsvaerd (DK)

(72) Inventors: Carsten Andersen, Vaerloese (DK); Lars Giger, Valby (DK); Johanne Mørch Jensen, Holte (DK); Louis Patrick Lessard, Wake Forest, NC (US)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 16/770,853

(22) PCT Filed: Dec. 7, 2018

(86) PCT No.: PCT/US2018/064415
§ 371 (c)(1),
(2) Date: Jun. 8, 2020

(87) PCT Pub. No.: WO2019/113415
PCT Pub. Date: Jun. 13, 2019

(65) Prior Publication Data
US 2020/0392474 A1  Dec. 17, 2020

Related U.S. Application Data

(60) Provisional application No. 62/765,268, filed on Aug. 20, 2018, provisional application No. 62/596,231, filed on Dec. 8, 2017.

(51) Int. Cl.
*C12N 9/28* (2006.01)
*C12N 9/34* (2006.01)

(52) U.S. Cl.
CPC ......... *C12N 9/2417* (2013.01); *C12N 9/2428* (2013.01); *C12Y 302/01001* (2013.01); *C12Y 302/01003* (2013.01)

(58) Field of Classification Search
CPC .. C12N 9/2414; C12N 9/2417; C12N 9/2428; C12Y 302/01003; C12Y 302/01001
See application file for complete search history.

(56) References Cited

U.S. PATENT DOCUMENTS

| | | | |
|---|---|---|---|
| 8,084,240 B2 | 12/2011 | Cuevas | |
| 8,507,243 B2 | 8/2013 | Paulson et al. | |
| 2009/0314286 A1* | 12/2009 | Cuevas | C12N 9/2417 |
| | | | 127/38 |

FOREIGN PATENT DOCUMENTS

| | | |
|---|---|---|
| WO | 96/23873 A1 | 8/1996 |
| WO | 99/19467 A2 | 4/1999 |
| WO | 00/60059 A2 | 10/2000 |
| WO | 2009/061379 A2 | 5/2009 |
| WO | 2009/061381 A2 | 5/2009 |
| WO | 2009/149130 A2 | 12/2009 |
| WO | 2010115021 A2 | 10/2010 |
| WO | 2011/082425 A2 | 7/2011 |
| WO | 2012/088303 A2 | 6/2012 |
| WO | 2013/057141 A2 | 4/2013 |
| WO | 2013/057143 A2 | 4/2013 |
| WO | 2013/082486 A1 | 6/2013 |
| WO | 2017/015329 A1 | 1/2015 |
| WO | 2015/050723 A1 | 4/2015 |

OTHER PUBLICATIONS

Gandhi et al, 2015, Biomed research international 2015, 1-9.
Nam et al, 2009, EBI Accession No. AWV26017.
Pujadas et al, 2001, Mol Biol Evol, 38-54.

(Continued)

*Primary Examiner* — Ganapathirama Raghu
(74) *Attorney, Agent, or Firm* — David Fazzolare

(57) ABSTRACT

The present invention relates to alpha-amylase variants comprising substitutions at positions corresponding to positions 268 and 293 of SEQ ID NO: 1, in particular substitutions selected from the group consisting of: 268G+293Y; 268G+293F; 268G+293W; 268G+293H; 268G+293A; 268G+293Q; 268A+293Y; 268A+293F; 268A+293W; 268A+293H; 268A+293A; 268A+293Q; 268P+293Y; 268P+293F; 268P+293W; 268P+293H; 268P+293A; 268P+293Q; 268S+293Y; 268S+293F; 268S+293W; 268S+293H; 268S+293A; 268S+293Q; 268T+293Y; 268T+293F; 268T+293W; 268T+293H; 268T+293A; 268T+293Q; 268V+293Y; 268V+293F; 268V+293W; 268V+293H; 268V+293A; 268V+293Q; 268I+293Y; 268I+293F; 268I+293W; 268I+293H; 268I+293A; 268I+293Q; 268L+293Y; 268L+293F; 268L+293W; 268L+293H; 268L+293A; 268L+293Q; 268M+293Y; 268M+293F; 268M+293W; 268M+293H; 268M+293A; 268M+293Q; and wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of SEQ ID NO: 1, SEQ ID NO: 2, SEQ ID NO: 3, SEQ ID NO: 4, and SEQ ID NO: 18. The present invention also relates to polynucleotides encoding the variants; nucleic acid constructs, vectors, and host cells comprising the polynucleotides; and methods of using the variants.

37 Claims, No Drawings
Specification includes a Sequence Listing.

(56) References Cited

OTHER PUBLICATIONS

WO 2015-050723 A1—EBI Accession No. JE823914.
Exhibit "B", Janecek et al., "The invariant residues in the α-amylase family: just the catalytic triad," Biologia, Bratislava, 58/6: 1127-1132, 2003.
Exhibit "C", Devos et al., "Practical Limits of Function Prediction," Proteins: Structure, Function, and Genetics 41: 98-107 (2000).

* cited by examiner

SEQUENCE LISTING

```
<160> NUMBER OF SEQ ID NOS: 18

<210> SEQ ID NO 1
<211> LENGTH: 484
<212> TYPE: PRT
<213> ORGANISM: Bacillus stearothermophilus
```

<400> SEQUENCE: 1

```
Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
                100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
        130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
                180                 185                 190

Asn Gly Asn Tyr Asp Tyr Leu Met Tyr Ala Asp Leu Asp Met Asp His
            195                 200                 205

Pro Glu Val Val Thr Glu Leu Lys Asn Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
                260                 265                 270

Leu His Asn Tyr Ile Thr Lys Thr Asn Gly Thr Met Ser Leu Phe Asp
            275                 280                 285

Ala Pro Leu His Asn Lys Phe Tyr Thr Ala Ser Lys Ser Gly Gly Ala
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
```

```
                       405                 410                 415
Thr Glu Lys Pro Gly Ser Gly Leu Ala Ala Leu Ile Thr Asp Gly Pro
                420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Ser Val Ser Val Trp
465                 470                 475                 480

Val Pro Arg Lys

<210> SEQ ID NO 2
<211> LENGTH: 583
<212> TYPE: PRT
<213> ORGANISM: Bacillus subtilis

<400> SEQUENCE: 2

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
                20                  25                  30

Asn Leu Ser Ser Leu Gly Ile Thr Ala Leu Trp Leu Pro Pro Ala Tyr
            35                  40                  45

Lys Gly Thr Ser Gln Ser Asp Val Gly Tyr Gly Val Tyr Asp Leu Tyr
        50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
                100                 105                 110

Gly Thr Glu Phe Val Asp Ala Val Glu Val Asp Pro Ser Asn Arg Asn
            115                 120                 125

Gln Glu Thr Ser Gly Thr Tyr Gln Ile Gln Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Ser Thr Gly Lys Ala Trp Asp Trp Glu Val Asp Thr
            180                 185                 190

Glu Asn Gly Asn Tyr Asp Tyr Leu Met Phe Ala Asp Leu Asp Met Asp
        195                 200                 205

His Pro Glu Val Val Thr Glu Leu Lys Asn Trp Gly Thr Trp Tyr Val
    210                 215                 220

Asn Thr Thr Asn Ile Asp Gly Phe Arg Leu Asp Ala Val Lys His Ile
225                 230                 235                 240

Lys Tyr Ser Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Thr Ala Ser Lys Ser Ser Gly
```

```
            290                 295                 300
Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
                325                 330                 335

Gln Ser Leu Gln Ser Trp Val Glu Pro Trp Phe Lys Pro Leu Ala Tyr
                340                 345                 350

Ala Phe Ile Leu Thr Arg Gln Glu Gly Tyr Pro Cys Val Phe Tyr Gly
            355                 360                 365

Asp Tyr Tyr Gly Ile Pro Lys Tyr Asn Ile Pro Gly Leu Lys Ser Lys
        370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415

Ile Asp Thr Lys Pro Asn Ser Gly Leu Ala Ala Leu Ile Thr Asp Gly
            420                 425                 430

Pro Gly Gly Ser Lys Trp Met Tyr Val Gly Lys Lys His Ala Gly Lys
        435                 440                 445

Val Phe Tyr Asp Leu Thr Gly Asn Arg Ser Asp Thr Val Thr Ile Asn
    450                 455                 460

Ala Asp Gly Trp Gly Glu Phe Lys Val Asn Gly Gly Ser Val Ser Ile
465                 470                 475                 480

Trp Val Ala Lys Thr Ser Asn Val Thr Phe Thr Val Asn Asn Ala Thr
                485                 490                 495

Thr Thr Ser Gly Gln Asn Val Tyr Val Val Ala Asn Ile Pro Glu Leu
            500                 505                 510

Gly Asn Trp Asn Thr Ala Asn Ala Ile Lys Met Asn Pro Ser Ser Tyr
        515                 520                 525

Pro Thr Trp Lys Ala Thr Ile Ala Leu Pro Gln Gly Lys Ala Ile Glu
    530                 535                 540

Phe Lys Phe Ile Lys Lys Asp Gln Ala Gly Asn Val Ile Trp Glu Ser
545                 550                 555                 560

Thr Ser Asn Arg Thr Tyr Thr Val Pro Phe Ser Ser Thr Gly Ser Tyr
                565                 570                 575

Thr Ala Ser Trp Asn Val Pro
            580

<210> SEQ ID NO 3
<211> LENGTH: 586
<212> TYPE: PRT
<213> ORGANISM: Bacillus sp

<400> SEQUENCE: 3

Gly Ser Val Pro Val Asn Gly Thr Met Met Gln Tyr Phe Glu Trp Tyr
1               5                   10                  15

Leu Pro Asp Asp Gly Thr Leu Trp Thr Lys Val Ala Asn Asn Ala Gln
                20                  25                  30

Ser Leu Ala Asn Leu Gly Ile Thr Ala Leu Trp Leu Pro Pro Ala Tyr
            35                  40                  45

Lys Gly Thr Ser Ser Asp Val Gly Tyr Gly Val Tyr Asp Leu Tyr
        50                  55                  60

Asp Leu Gly Glu Phe Asn Gln Lys Gly Thr Val Arg Thr Lys Tyr Gly
65                  70                  75                  80
```

-continued

```
Thr Lys Thr Gln Tyr Ile Gln Ala Ile Gln Ala Ala His Thr Ala Gly
                    85                  90                  95
Met Gln Val Tyr Ala Asp Val Val Phe Asn His Lys Ala Gly Ala Asp
            100                 105                 110
Gly Thr Glu Leu Val Asp Ala Val Glu Val Asn Pro Ser Asp Arg Asn
        115                 120                 125
Gln Glu Ile Ser Gly Thr Tyr Gln Ile Gln Ala Trp Thr Lys Phe Asp
    130                 135                 140
Phe Pro Gly Arg Gly Asn Thr Tyr Ser Ser Phe Lys Trp Arg Trp Tyr
145                 150                 155                 160
His Phe Asp Gly Thr Asp Trp Asp Glu Ser Arg Lys Leu Asn Arg Ile
                165                 170                 175
Tyr Lys Phe Arg Gly Thr Gly Lys Ala Trp Asp Trp Glu Val Asp Thr
            180                 185                 190
Glu Asn Gly Asn Tyr Asp Tyr Leu Met Tyr Ala Asp Leu Asp Met Asp
        195                 200                 205
His Pro Glu Val Val Ser Glu Leu Lys Asn Trp Gly Lys Trp Tyr Val
    210                 215                 220
Thr Thr Thr Asn Ile Asp Gly Phe Arg Leu Asp Ala Val Lys His Ile
225                 230                 235                 240
Lys Tyr Ser Phe Phe Pro Asp Trp Leu Ser Tyr Val Arg Thr Gln Thr
                245                 250                 255
Gln Lys Pro Leu Phe Ala Val Gly Glu Phe Trp Ser Tyr Asp Ile Ser
            260                 265                 270
Lys Leu His Asn Tyr Ile Thr Lys Thr Asn Gly Ser Met Ser Leu Phe
        275                 280                 285
Asp Ala Pro Leu His Asn Asn Phe Tyr Ile Ala Ser Lys Ser Gly Gly
    290                 295                 300
Tyr Phe Asp Met Arg Thr Leu Leu Asn Asn Thr Leu Met Lys Asp Gln
305                 310                 315                 320
Pro Thr Leu Ala Val Thr Leu Val Asp Asn His Asp Thr Glu Pro Gly
                325                 330                 335
Gln Ser Leu Gln Ser Trp Val Glu Pro Trp Phe Lys Pro Leu Ala Tyr
            340                 345                 350
Ala Phe Ile Leu Thr Arg Gln Glu Gly Tyr Pro Cys Val Phe Tyr Gly
        355                 360                 365
Asp Tyr Tyr Gly Ile Pro Lys Tyr Asn Ile Pro Ala Leu Lys Ser Lys
    370                 375                 380
Leu Asp Pro Leu Leu Ile Ala Arg Arg Asp Tyr Ala Tyr Gly Thr Gln
385                 390                 395                 400
His Asp Tyr Ile Asp Ser Ala Asp Ile Ile Gly Trp Thr Arg Glu Gly
                405                 410                 415
Val Ala Glu Lys Ala Asn Ser Gly Leu Ala Ala Leu Ile Thr Asp Gly
            420                 425                 430
Pro Gly Gly Ser Lys Trp Met Tyr Val Gly Lys Gln His Ala Gly Lys
        435                 440                 445
Thr Phe Tyr Asp Leu Thr Gly Asn Arg Ser Asp Thr Val Thr Ile Asn
    450                 455                 460
Ala Asp Gly Trp Gly Glu Phe Lys Val Asn Gly Gly Ser Val Ser Ile
465                 470                 475                 480
Trp Val Pro Lys Ile Ser Thr Ser Gln Ile Thr Phe Thr Val Asn
                485                 490                 495
Asn Ala Thr Thr Val Trp Gly Gln Asn Val Tyr Val Val Gly Asn Ile
```

```
                500             505             510
Ser Gln Leu Gly Asn Trp Asp Pro Val His Ala Val Gln Met Thr Pro
        515                 520                 525

Ser Ser Tyr Pro Thr Trp Thr Val Thr Ile Pro Leu Leu Gln Gly Gln
        530                 535                 540

Asn Ile Gln Phe Lys Phe Ile Lys Lys Asp Ser Ala Gly Asn Val Ile
545                 550                 555                 560

Trp Glu Asp Ile Ser Asn Arg Thr Tyr Thr Val Pro Thr Ala Ala Ser
                565                 570                 575

Gly Ala Tyr Thr Ala Ser Trp Asn Val Pro
                580                 585

<210> SEQ ID NO 4
<211> LENGTH: 491
<212> TYPE: PRT
<213> ORGANISM: Artificial
<220> FEATURE:
<223> OTHER INFORMATION: Variant of SEQ ID NO: 1

<400> SEQUENCE: 4

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
            35                  40                  45

Gly Thr Ser Arg Ser Asp Val Gly Tyr Gly Ala Tyr Asp Leu Tyr Asp
        50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
                100                 105                 110

Thr Glu Trp Val Asp Ala Val Glu Val Asn Pro Ser Asp Arg Asn Gln
            115                 120                 125

Val Ile Ser Gly Thr Tyr Gln Ile Gln Ala Trp Thr Lys Phe Asp Phe
        130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Leu Phe Glu Gly Lys Ala Trp Asp Trp Glu Val Asp Thr Glu Phe Gly
                180                 185                 190

Asn Tyr Asp Tyr Leu Met Tyr Ala Asp Leu Asp Met Asp His Pro Glu
            195                 200                 205

Val Thr Thr Glu Leu Lys Asn Trp Gly Lys Trp Tyr Val Asn Thr Thr
        210                 215                 220

Asn Ile Asp Gly Phe Arg Leu Asp Ala Val Lys His Ile Lys Phe Ser
225                 230                 235                 240

Phe Phe Pro Asp Trp Leu Ser Tyr Val Arg Ser Ser Thr Gly Lys Pro
                245                 250                 255

Leu Phe Thr Val Gly Glu Tyr Trp Ser Tyr Asp Ile Asn Lys Leu His
                260                 265                 270

Asn Tyr Ile Thr Lys Thr Asp Gly Thr Val Ser Leu Phe Asp Ala Pro
```

```
            275                 280                 285
Leu His Asn Lys Phe Tyr Thr Ala Ser Lys Ser Gly Gly Ala Phe Asp
290                 295                 300

Met Arg Thr Leu Met Thr Asn Thr Leu Met Lys Asp Gln Pro Thr Leu
305                 310                 315                 320

Ala Val Thr Phe Val Asp Asn His Asp Thr Glu Pro Gly Gln Ala Leu
                325                 330                 335

Gln Ser Trp Val Asp Pro Trp Phe Lys Pro Leu Ala Tyr Ala Phe Ile
            340                 345                 350

Leu Thr Arg Gln Glu Gly Tyr Pro Cys Val Phe Tyr Gly Asp Tyr Tyr
        355                 360                 365

Gly Ile Pro Gln Tyr Asn Ile Pro Ser Leu Lys Ser Lys Ile Asp Pro
    370                 375                 380

Leu Leu Ile Ala Arg Arg Asp Tyr Ala Tyr Gly Thr Gln His Asp Tyr
385                 390                 395                 400

Leu Asp His Ser Asp Ile Ile Gly Trp Thr Arg Glu Gly Gly Thr Glu
                405                 410                 415

Lys Pro Gly Ser Gly Leu Ala Ala Leu Ile Thr Asp Gly Pro Gly Gly
            420                 425                 430

Ser Lys Trp Met Tyr Val Gly Lys Gln His Ala Gly Lys Val Phe Tyr
        435                 440                 445

Asp Leu Thr Gly Asn Arg Ser Asp Thr Val Thr Ile Asn Ser Asp Gly
    450                 455                 460

Trp Gly Glu Phe Lys Val Asn Gly Gly Ser Val Ser Val Trp Val Pro
465                 470                 475                 480

Arg Lys Thr Thr Val Ser Thr Ile Ala Arg Pro
                485                 490

<210> SEQ ID NO 5
<211> LENGTH: 491
<212> TYPE: PRT
<213> ORGANISM: Artificial
<220> FEATURE:
<223> OTHER INFORMATION: Variant of SEQ ID NO: 1

<400> SEQUENCE: 5

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Ala Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Val Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
```

```
        145                 150                 155                 160
Phe Asp Gly Val Asp Trp Asp Glu Ser Arg Lys Leu Ser Arg Ile Tyr
                165                 170                 175

Leu Phe Glu Gly Lys Ala Trp Asp Trp Glu Val Asp Thr Glu Phe Gly
                180                 185                 190

Asn Tyr Asp Tyr Leu Met Tyr Ala Asp Leu Asp Met Asp His Pro Glu
                195                 200                 205

Val Thr Thr Glu Leu Lys Asn Trp Gly Lys Trp Tyr Val Asn Thr Thr
    210                 215                 220

Asn Ile Asp Gly Phe Arg Leu Asp Ala Val Lys His Ile Lys Phe Ser
225                 230                 235                 240

Phe Phe Pro Asp Trp Leu Ser Tyr Val Arg Ser Ser Thr Gly Lys Pro
                245                 250                 255

Leu Phe Thr Val Gly Glu Tyr Trp Ser Gly Asp Ile Asn Lys Leu His
                260                 265                 270

Asn Tyr Ile Thr Lys Thr Asp Gly Thr Val Ser Leu Phe Asp Ala Pro
                275                 280                 285

Leu His Tyr Lys Phe Tyr Asn Ala Ser Lys Ser Gly Gly Ala Phe Asp
                290                 295                 300

Met Arg Thr Leu Met Thr Asn Thr Leu Met Lys Asp Gln Pro Thr Leu
305                 310                 315                 320

Ala Val Thr Phe Val Asp Asn His Asp Thr Glu Pro Gly Gln Ala Leu
                325                 330                 335

Gln Ser Trp Val Asp Pro Trp Phe Lys Pro Leu Ala Tyr Ala Phe Ile
                340                 345                 350

Leu Thr Arg Gln Glu Gly Tyr Pro Cys Val Phe Tyr Gly Asp Tyr Tyr
                355                 360                 365

Gly Ile Pro Gln Tyr Asn Ile Pro Ser Leu Lys Ser Lys Ile Asp Pro
                370                 375                 380

Leu Leu Ile Ala Arg Arg Asp Tyr Ala Tyr Gly Thr Gln His Asp Tyr
385                 390                 395                 400

Leu Asp His Ser Asp Ile Ile Gly Trp Thr Arg Glu Gly Gly Thr Glu
                405                 410                 415

Lys Pro Gly Ser Gly Leu Ala Ala Leu Ile Thr Asp Gly Pro Gly Gly
                420                 425                 430

Ser Lys Trp Met Tyr Val Gly Lys Gln His Ala Gly Lys Val Phe Tyr
                435                 440                 445

Asp Leu Thr Gly Asn Arg Ser Asp Thr Val Thr Ile Asn Ser Asp Gly
                450                 455                 460

Trp Gly Glu Phe Lys Val Asn Gly Gly Ser Val Ser Val Trp Val Pro
465                 470                 475                 480

Arg Lys Thr Thr Val Ser Thr Ile Ala Arg Pro
                485                 490

<210> SEQ ID NO 6
<211> LENGTH: 485
<212> TYPE: PRT
<213> ORGANISM: Cytophaga

<400> SEQUENCE: 6

Ala Ala Thr Asn Gly Thr Met Met Gln Tyr Phe Glu Trp Tyr Val Pro
1               5                   10                  15

Asn Asp Gly Gln Gln Trp Asn Arg Leu Arg Thr Asp Ala Pro Tyr Leu
                20                  25                  30
```

```
Ser Ser Val Gly Ile Thr Ala Val Trp Thr Pro Pro Ala Tyr Lys Gly
         35                  40                  45

Thr Ser Gln Ala Asp Val Gly Tyr Gly Pro Tyr Asp Leu Tyr Asp Leu
 50                  55                  60

Gly Glu Phe Asn Gln Lys Gly Thr Val Arg Thr Lys Tyr Gly Thr Lys
 65                  70                  75                  80

Gly Glu Leu Lys Ser Ala Val Asn Thr Leu His Ser Asn Gly Ile Gln
             85                  90                  95

Val Tyr Gly Asp Val Val Met Asn His Lys Ala Gly Ala Asp Tyr Thr
             100                 105                 110

Glu Asn Val Thr Ala Val Glu Val Asn Pro Ser Asn Arg Asn Gln Glu
             115                 120                 125

Thr Ser Gly Glu Tyr Asn Ile Gln Ala Trp Thr Gly Phe Asn Phe Pro
 130                 135                 140

Gly Arg Gly Thr Thr Tyr Ser Asn Phe Lys Trp Gln Trp Phe His Phe
 145                 150                 155                 160

Asp Gly Thr Asp Trp Asp Gln Ser Arg Ser Leu Ser Arg Ile Phe Lys
                 165                 170                 175

Phe Arg Gly Thr Gly Lys Ala Trp Asp Trp Glu Val Ser Ser Glu Asn
             180                 185                 190

Gly Asn Tyr Asp Tyr Leu Met Tyr Ala Asp Ile Asp Tyr Asp His Pro
             195                 200                 205

Asp Val Val Asn Glu Met Lys Lys Trp Gly Val Trp Tyr Ala Asn Glu
             210                 215                 220

Val Gly Leu Asp Gly Tyr Arg Leu Asp Ala Val Lys His Ile Lys Phe
225                 230                 235                 240

Ser Phe Leu Lys Asp Trp Val Asp Asn Ala Arg Ala Ala Thr Gly Lys
                 245                 250                 255

Glu Met Phe Thr Val Gly Glu Tyr Trp Gln Asn Asp Leu Gly Ala Leu
             260                 265                 270

Asn Asn Tyr Leu Ala Lys Val Asn Tyr Asn Gln Ser Leu Phe Asp Ala
             275                 280                 285

Pro Leu His Tyr Asn Phe Tyr Ala Ala Ser Thr Gly Gly Gly Tyr Tyr
             290                 295                 300

Asp Met Arg Asn Ile Leu Asn Asn Thr Leu Val Ala Ser Asn Pro Thr
305                 310                 315                 320

Lys Ala Val Thr Leu Val Glu Asn His Asp Thr Gln Pro Gly Gln Ser
                 325                 330                 335

Leu Glu Ser Thr Val Gln Pro Trp Phe Lys Pro Leu Ala Tyr Ala Phe
             340                 345                 350

Ile Leu Thr Arg Ser Gly Gly Tyr Pro Ser Val Phe Tyr Gly Asp Met
             355                 360                 365

Tyr Gly Thr Lys Gly Thr Thr Thr Arg Glu Ile Pro Ala Leu Lys Ser
 370                 375                 380

Lys Ile Glu Pro Leu Leu Lys Ala Arg Lys Asp Tyr Ala Tyr Gly Thr
385                 390                 395                 400

Gln Arg Asp Tyr Ile Asp Asn Pro Asp Val Ile Gly Trp Thr Arg Glu
                 405                 410                 415

Gly Asp Ser Thr Lys Ala Lys Ser Gly Leu Ala Thr Val Ile Thr Asp
             420                 425                 430

Gly Pro Gly Gly Ser Lys Arg Met Tyr Val Gly Thr Ser Asn Ala Gly
             435                 440                 445

Glu Ile Trp Tyr Asp Leu Thr Gly Asn Arg Thr Asp Lys Ile Thr Ile
```

```
              450                 455                 460
Gly Ser Asp Gly Tyr Ala Thr Phe Pro Val Asn Gly Gly Ser Val Ser
465                 470                 475                 480

Val Trp Val Gln Gln
            485

<210> SEQ ID NO 7
<211> LENGTH: 413
<212> TYPE: PRT
<213> ORGANISM: Pyrococcus furiosus

<400> SEQUENCE: 7

Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
                20                  25                  30

Ile Asp Thr Gly Ile Asp Ala Ser His Pro Asp Leu Gln Gly Lys Val
            35                  40                  45

Ile Gly Trp Val Asp Phe Val Asn Gly Arg Ser Tyr Pro Tyr Asp Asp
        50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly
        195                 200                 205

Arg Leu Lys Pro Glu Val Val Ala Pro Gly Asn Trp Ile Ile Ala Ala
210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
        275                 280                 285

Asp Ile Ala Tyr Gly Ala Gly Arg Val Asn Ala Tyr Lys Ala Ile Asn
290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335
```

```
Ala Thr Leu Tyr Trp Asp Asn Ala Asn Ser Asp Leu Asp Leu Tyr Leu
            340                 345                 350

Tyr Asp Pro Asn Gly Asn Gln Val Asp Tyr Ser Tyr Thr Ala Tyr Tyr
        355                 360                 365

Asp Phe Glu Lys Val Gly Tyr Tyr Asn Pro Thr Asp Gly Thr Trp Thr
    370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser Pro
                405                 410

<210> SEQ ID NO 8
<211> LENGTH: 177
<212> TYPE: PRT
<213> ORGANISM: Thermoascus aurantiacus

<400> SEQUENCE: 8

Thr Arg Ile Ser Ser Cys Ser Gly Ser Arg Gln Ser Ala Leu Thr Thr
1               5                   10                  15

Ala Leu Arg Asn Ala Ala Ser Leu Ala Asn Ala Ala Asp Ala Ala
            20                  25                  30

Gln Ser Gly Ser Ala Ser Lys Phe Ser Glu Tyr Phe Lys Thr Thr Ser
        35                  40                  45

Ser Ser Thr Arg Gln Thr Val Ala Ala Arg Leu Arg Ala Val Ala Arg
    50                  55                  60

Glu Ala Ser Ser Ser Ser Gly Ala Thr Thr Tyr Tyr Cys Asp Asp
65                  70                  75                  80

Pro Tyr Gly Tyr Cys Ser Ser Asn Val Leu Ala Tyr Thr Leu Pro Ser
                85                  90                  95

Tyr Asn Ile Ile Ala Asn Cys Asp Ile Phe Tyr Thr Tyr Leu Pro Ala
            100                 105                 110

Leu Thr Ser Thr Cys His Ala Gln Asp Gln Ala Thr Thr Ala Leu His
        115                 120                 125

Glu Phe Thr His Ala Pro Gly Val Tyr Ser Pro Gly Thr Asp Asp Leu
    130                 135                 140

Ala Tyr Gly Tyr Gln Ala Ala Met Gly Leu Ser Ser Ser Gln Ala Val
145                 150                 155                 160

Met Asn Ala Asp Thr Tyr Ala Leu Tyr Ala Asn Ala Ile Tyr Leu Gly
                165                 170                 175

Cys

<210> SEQ ID NO 9
<211> LENGTH: 595
<212> TYPE: PRT
<213> ORGANISM: Penicillium oxalicum

<400> SEQUENCE: 9

Arg Pro Asp Pro Lys Gly Gly Asn Leu Thr Pro Phe Ile His Lys Glu
1               5                   10                  15

Gly Glu Arg Ser Leu Gln Gly Ile Leu Asp Asn Leu Gly Gly Arg Gly
            20                  25                  30

Lys Lys Thr Pro Gly Thr Ala Ala Gly Leu Phe Ile Ala Ser Pro Asn
        35                  40                  45

Thr Glu Asn Pro Asn Tyr Tyr Tyr Thr Trp Thr Arg Asp Ser Ala Leu
    50                  55                  60

Thr Ala Lys Cys Leu Ile Asp Leu Phe Glu Asp Ser Arg Ala Lys Phe
```

```
            65                  70                  75                  80
Pro Ile Asp Arg Lys Tyr Leu Glu Thr Gly Ile Arg Asp Tyr Lys Ser
                    85                  90                  95

Ser Gln Ala Ile Leu Gln Ser Val Ser Asn Pro Ser Gly Thr Leu Lys
            100                 105                 110

Asp Gly Ser Gly Leu Gly Glu Pro Lys Phe Glu Ile Asp Leu Asn Pro
            115                 120                 125

Phe Ser Gly Ala Trp Gly Arg Pro Gln Arg Asp Gly Pro Ala Leu Arg
            130                 135                 140

Ala Thr Ala Met Ile Thr Tyr Ala Asn Tyr Leu Ile Ser His Gly Gln
145                 150                 155                 160

Lys Ser Asp Val Ser Gln Val Met Trp Pro Ile Ile Ala Asn Asp Leu
                    165                 170                 175

Ala Tyr Val Gly Gln Tyr Trp Asn Asn Thr Gly Phe Asp Leu Trp Glu
            180                 185                 190

Glu Val Asp Gly Ser Ser Phe Phe Thr Ile Ala Val Gln His Arg Ala
                    195                 200                 205

Leu Val Glu Gly Ser Gln Leu Ala Lys Lys Leu Gly Lys Ser Cys Asp
            210                 215                 220

Ala Cys Asp Ser Gln Pro Pro Gln Ile Leu Cys Phe Leu Gln Ser Phe
225                 230                 235                 240

Trp Asn Gly Lys Tyr Ile Thr Ser Asn Ile Asn Thr Gln Ala Ser Arg
                    245                 250                 255

Ser Gly Ile Asp Leu Asp Ser Val Leu Gly Ser Ile His Thr Phe Asp
            260                 265                 270

Pro Glu Ala Ala Cys Asp Asp Ala Thr Phe Gln Pro Cys Ser Ala Arg
                    275                 280                 285

Ala Leu Ala Asn His Lys Val Tyr Val Asp Ser Phe Arg Ser Ile Tyr
            290                 295                 300

Lys Ile Asn Ala Gly Leu Ala Glu Gly Ser Ala Ala Asn Val Gly Arg
305                 310                 315                 320

Tyr Pro Glu Asp Val Tyr Gln Gly Gly Asn Pro Trp Tyr Leu Ala Thr
                    325                 330                 335

Leu Gly Ala Ser Glu Leu Leu Tyr Asp Ala Leu Tyr Gln Trp Asp Arg
            340                 345                 350

Leu Gly Lys Leu Glu Val Ser Glu Thr Ser Leu Ser Phe Phe Lys Asp
            355                 360                 365

Phe Asp Ala Thr Val Lys Ile Gly Ser Tyr Ser Arg Asn Ser Lys Thr
            370                 375                 380

Tyr Lys Lys Leu Thr Gln Ser Ile Lys Ser Tyr Ala Asp Gly Phe Ile
385                 390                 395                 400

Gln Leu Val Gln Gln Tyr Thr Pro Ser Asn Gly Ser Leu Ala Glu Gln
                    405                 410                 415

Tyr Asp Arg Asn Thr Ala Ala Pro Leu Ser Ala Asn Asp Leu Thr Trp
            420                 425                 430

Ser Phe Ala Ser Phe Leu Thr Ala Thr Gln Arg Arg Asp Ala Val Val
            435                 440                 445

Pro Pro Ser Trp Gly Ala Lys Ser Ala Asn Lys Val Pro Thr Thr Cys
            450                 455                 460

Ser Ala Ser Pro Val Val Gly Thr Tyr Lys Ala Pro Thr Ala Thr Phe
465                 470                 475                 480

Ser Ser Lys Thr Lys Cys Val Pro Ala Lys Asp Ile Val Pro Ile Thr
                    485                 490                 495
```

```
Phe Tyr Leu Ile Glu Asn Thr Tyr Tyr Gly Glu Asn Val Phe Met Ser
            500                 505                 510

Gly Asn Ile Thr Ala Leu Gly Asn Trp Asp Ala Lys Lys Gly Phe Pro
            515                 520                 525

Leu Thr Ala Asn Leu Tyr Thr Gln Asp Gln Asn Leu Trp Phe Ala Ser
530                 535                 540

Val Glu Phe Ile Pro Ala Gly Thr Pro Phe Glu Tyr Lys Tyr Tyr Lys
545                 550                 555                 560

Val Glu Pro Asn Gly Asp Ile Thr Trp Glu Lys Gly Pro Asn Arg Val
                565                 570                 575

Phe Val Ala Pro Thr Gly Cys Pro Val Gln Pro His Ser Asn Asp Val
            580                 585                 590

Trp Gln Phe
        595
```

<210> SEQ ID NO 10
<211> LENGTH: 598
<212> TYPE: PRT
<213> ORGANISM: Talaromyces emersonii

<400> SEQUENCE: 10

```
Arg Ala Pro Val Ala Ala Arg Ala Thr Gly Ser Leu Asp Ser Phe Leu
1               5                   10                  15

Ala Thr Glu Thr Pro Ile Ala Leu Gln Gly Val Leu Asn Asn Ile Gly
            20                  25                  30

Pro Asn Gly Ala Asp Val Ala Gly Ala Ser Ala Gly Ile Val Val Ala
        35                  40                  45

Ser Pro Ser Arg Ser Asp Pro Asn Tyr Phe Tyr Ser Trp Thr Arg Asp
50                  55                  60

Ala Ala Leu Thr Ala Lys Tyr Leu Val Asp Ala Phe Ile Ala Gly Asn
65                  70                  75                  80

Lys Asp Leu Glu Gln Thr Ile Gln Gln Tyr Ile Ser Ala Gln Ala Lys
                85                  90                  95

Val Gln Thr Ile Ser Asn Pro Ser Gly Asp Leu Ser Thr Gly Gly Leu
            100                 105                 110

Gly Glu Pro Lys Phe Asn Val Asn Glu Thr Ala Phe Thr Gly Pro Trp
        115                 120                 125

Gly Arg Pro Gln Arg Asp Gly Pro Ala Leu Arg Ala Thr Ala Leu Ile
130                 135                 140

Ala Tyr Ala Asn Tyr Leu Ile Asp Asn Gly Glu Ala Ser Thr Ala Asp
145                 150                 155                 160

Glu Ile Ile Trp Pro Ile Val Gln Asn Asp Leu Ser Tyr Ile Thr Gln
                165                 170                 175

Tyr Trp Asn Ser Ser Thr Phe Asp Leu Trp Glu Glu Val Glu Gly Ser
            180                 185                 190

Ser Phe Phe Thr Thr Ala Val Gln His Arg Ala Leu Val Glu Gly Asn
        195                 200                 205

Ala Leu Ala Thr Arg Leu Asn His Thr Cys Ser Asn Cys Val Ser Gln
210                 215                 220

Ala Pro Gln Val Leu Cys Phe Leu Gln Ser Tyr Trp Thr Gly Ser Tyr
225                 230                 235                 240

Val Leu Ala Asn Phe Gly Gly Ser Gly Arg Ser Gly Lys Asp Val Asn
                245                 250                 255

Ser Ile Leu Gly Ser Ile His Thr Phe Asp Pro Ala Gly Gly Cys Asp
```

Asp Ser Thr Phe Gln Pro Cys Ser Ala Arg Ala Leu Ala Asn His Lys
            275                 280                 285

Val Val Thr Asp Ser Phe Arg Ser Ile Tyr Ala Ile Asn Ser Gly Ile
            290                 295                 300

Ala Glu Gly Ser Ala Val Ala Val Gly Arg Tyr Pro Glu Asp Val Tyr
305                 310                 315                 320

Gln Gly Gly Asn Pro Trp Tyr Leu Ala Thr Ala Ala Ala Glu Gln
            325                 330                 335

Leu Tyr Asp Ala Ile Tyr Gln Trp Lys Lys Ile Gly Ser Ile Ser Ile
            340                 345                 350

Thr Asp Val Ser Leu Pro Phe Phe Gln Asp Ile Tyr Pro Ser Ala Ala
            355                 360                 365

Val Gly Thr Tyr Asn Ser Gly Ser Thr Thr Phe Asn Asp Ile Ile Ser
            370                 375                 380

Ala Val Gln Thr Tyr Gly Asp Gly Tyr Leu Ser Ile Val Glu Lys Tyr
385                 390                 395                 400

Thr Pro Ser Asp Gly Ser Leu Thr Glu Gln Phe Ser Arg Thr Asp Gly
            405                 410                 415

Thr Pro Leu Ser Ala Ser Ala Leu Thr Trp Ser Tyr Ala Ser Leu Leu
            420                 425                 430

Thr Ala Ser Ala Arg Arg Gln Ser Val Val Pro Ala Ser Trp Gly Glu
            435                 440                 445

Ser Ser Ala Ser Ser Val Pro Ala Val Cys Ser Ala Thr Ser Ala Thr
450                 455                 460

Gly Pro Tyr Ser Thr Ala Thr Asn Thr Val Trp Pro Ser Ser Gly Ser
465                 470                 475                 480

Gly Ser Ser Thr Thr Thr Ser Ser Ala Pro Cys Thr Thr Pro Thr Ser
            485                 490                 495

Val Ala Val Thr Phe Asp Glu Ile Val Ser Thr Ser Tyr Gly Glu Thr
            500                 505                 510

Ile Tyr Leu Ala Gly Ser Ile Pro Glu Leu Gly Asn Trp Ser Thr Ala
            515                 520                 525

Ser Ala Ile Pro Leu Arg Ala Asp Ala Tyr Thr Asn Ser Asn Pro Leu
            530                 535                 540

Trp Tyr Val Thr Val Asn Leu Pro Pro Gly Thr Ser Phe Glu Tyr Lys
545                 550                 555                 560

Phe Phe Lys Asn Gln Thr Asp Gly Thr Ile Val Trp Glu Asp Pro
            565                 570                 575

Asn Arg Ser Tyr Thr Val Pro Ala Tyr Cys Gly Gln Thr Thr Ala Ile
            580                 585                 590

Leu Asp Asp Ser Trp Gln
        595

<210> SEQ ID NO 11
<211> LENGTH: 555
<212> TYPE: PRT
<213> ORGANISM: Pycnoporus sanguinea

<400> SEQUENCE: 11

Gln Ser Ser Ala Val Asp Ala Tyr Val Ala Ser Glu Ser Pro Ile Ala
1               5                   10                  15

Lys Gln Gly Val Leu Asn Asn Ile Gly Pro Asn Gly Ser Lys Ala His
            20                  25                  30

-continued

```
Gly Ala Lys Ala Gly Ile Val Val Ala Ser Pro Ser Thr Glu Asn Pro
            35                  40                  45

Asp Tyr Leu Tyr Thr Trp Thr Arg Asp Ser Ser Leu Val Phe Lys Leu
 50                  55                  60

Leu Ile Asp Gln Phe Thr Ser Gly Asp Thr Ser Leu Arg Gly Leu
65                  70                  75                  80

Ile Asp Asp Phe Thr Ser Ala Glu Ala Ile Leu Gln Gln Val Ser Asn
                85                  90                  95

Pro Ser Gly Thr Val Ser Thr Gly Leu Gly Glu Pro Lys Phe Asn
            100                 105                 110

Ile Asp Glu Thr Ala Phe Thr Gly Ala Trp Gly Arg Pro Gln Arg Asp
            115                 120                 125

Gly Pro Ala Leu Arg Ala Thr Ser Ile Ile Arg Tyr Ala Asn Trp Leu
130                 135                 140

Leu Asp Asn Gly Asn Thr Thr Tyr Val Ser Asn Thr Leu Trp Pro Val
145                 150                 155                 160

Ile Gln Leu Asp Leu Asp Tyr Val Ala Asp Asn Trp Asn Gln Ser Thr
                165                 170                 175

Phe Asp Leu Trp Glu Glu Val Asp Ser Ser Phe Phe Thr Thr Ala
            180                 185                 190

Val Gln His Arg Ala Leu Arg Glu Gly Ala Thr Phe Ala Ser Arg Ile
            195                 200                 205

Gly Gln Ser Ser Val Val Ser Gly Tyr Thr Thr Gln Ala Asp Asn Leu
            210                 215                 220

Leu Cys Phe Leu Gln Ser Tyr Trp Asn Pro Ser Gly Gly Tyr Val Thr
225                 230                 235                 240

Ala Asn Thr Gly Gly Gly Arg Ser Gly Lys Asp Ser Asn Thr Val Leu
                245                 250                 255

Thr Ser Ile His Thr Phe Asp Pro Ala Ala Gly Cys Asp Ala Ala Thr
                260                 265                 270

Phe Gln Pro Cys Ser Asp Lys Ala Leu Ser Asn Leu Lys Val Tyr Val
            275                 280                 285

Asp Ala Phe Arg Ser Ile Tyr Thr Ile Asn Asn Gly Ile Ala Ser Asn
            290                 295                 300

Ala Ala Val Ala Thr Gly Arg Tyr Pro Glu Asp Ser Tyr Met Gly Gly
305                 310                 315                 320

Asn Pro Trp Tyr Leu Thr Thr Ser Ala Val Ala Glu Gln Leu Tyr Asp
                325                 330                 335

Ala Leu Tyr Val Trp Asp Gln Leu Gly Gly Leu Asn Val Thr Ser Thr
            340                 345                 350

Ser Leu Ala Phe Phe Gln Gln Phe Ala Ser Gly Leu Ser Thr Gly Thr
            355                 360                 365

Tyr Ser Ala Ser Ser Ser Thr Tyr Ala Thr Leu Thr Ser Ala Ile Arg
370                 375                 380

Ser Phe Ala Asp Gly Phe Leu Ala Ile Asn Ala Lys Tyr Thr Pro Ala
385                 390                 395                 400

Asp Gly Gly Leu Ala Glu Gln Tyr Ser Arg Asn Asp Gly Thr Pro Leu
                405                 410                 415

Ser Ala Val Asp Leu Thr Trp Ser Tyr Ala Ala Leu Thr Ala Phe
            420                 425                 430

Ala Ala Arg Glu Gly Lys Thr Tyr Gly Ser Trp Gly Ala Ala Gly Leu
            435                 440                 445

Thr Val Pro Ala Ser Cys Ser Gly Gly Gly Gly Ala Thr Val Ala Val
```

```
                450           455           460
Thr Phe Asn Val Gln Ala Thr Thr Val Phe Gly Glu Asn Ile Tyr Ile
465                 470                 475                 480

Thr Gly Ser Val Ala Ala Leu Gln Asn Trp Ser Pro Asp Asn Ala Leu
                485                 490                 495

Ile Leu Ser Ala Ala Asn Tyr Pro Thr Trp Ser Ile Thr Val Asn Leu
                500                 505                 510

Pro Ala Asn Thr Val Val Gln Tyr Lys Tyr Ile Arg Lys Phe Asn Gly
                515                 520                 525

Gln Val Thr Trp Glu Ser Asp Pro Asn Gln Ile Thr Thr Pro Ser
                530                 535                 540

Gly Gly Ser Phe Thr Gln Asn Asp Val Trp Arg
545                 550                 555
```

<210> SEQ ID NO 12
<211> LENGTH: 556
<212> TYPE: PRT
<213> ORGANISM: Gloeophyllum sepiarium

<400> SEQUENCE: 12

```
Gln Ser Val Asp Ser Tyr Val Ser Ser Glu Gly Pro Ile Ala Lys Ala
1               5                   10                  15

Gly Val Leu Ala Asn Ile Gly Pro Asn Gly Ser Lys Ala Ser Gly Ala
                20                  25                  30

Ser Ala Gly Val Val Ala Ser Pro Ser Thr Ser Asp Pro Asp Tyr
                35                  40                  45

Trp Tyr Thr Trp Thr Arg Asp Ser Ser Leu Val Phe Lys Ser Leu Ile
50                  55                  60

Asp Gln Tyr Thr Thr Gly Ile Asp Ser Thr Ser Ser Leu Arg Thr Leu
65                  70                  75                  80

Ile Asp Asp Phe Val Thr Ala Glu Ala Asn Leu Gln Gln Val Ser Asn
                85                  90                  95

Pro Ser Gly Thr Leu Thr Thr Gly Gly Leu Gly Glu Pro Lys Phe Asn
                100                 105                 110

Val Asp Glu Thr Ala Phe Thr Gly Ala Trp Gly Arg Pro Gln Arg Asp
                115                 120                 125

Gly Pro Ala Leu Arg Ser Thr Ala Leu Ile Thr Tyr Gly Asn Trp Leu
130                 135                 140

Leu Ser Asn Gly Asn Thr Ser Tyr Val Thr Ser Asn Leu Trp Pro Ile
145                 150                 155                 160

Ile Gln Asn Asp Leu Gly Tyr Val Val Ser Tyr Trp Asn Gln Ser Thr
                165                 170                 175

Tyr Asp Leu Trp Glu Glu Val Asp Ser Ser Phe Phe Thr Thr Ala
                180                 185                 190

Val Gln His Arg Ala Leu Arg Glu Gly Ala Ala Phe Ala Thr Ala Ile
                195                 200                 205

Gly Gln Thr Ser Gln Val Ser Ser Tyr Thr Thr Gln Ala Asp Asn Leu
                210                 215                 220

Leu Cys Phe Leu Gln Ser Tyr Trp Asn Pro Ser Gly Gly Tyr Ile Thr
225                 230                 235                 240

Ala Asn Thr Gly Gly Gly Arg Ser Gly Lys Asp Ala Asn Thr Leu Leu
                245                 250                 255

Ala Ser Ile His Thr Tyr Asp Pro Ser Ala Gly Cys Asp Ala Ala Thr
                260                 265                 270
```

```
Phe Gln Pro Cys Ser Asp Lys Ala Leu Ser Asn Leu Lys Val Tyr Val
            275                 280                 285

Asp Ser Phe Arg Ser Val Tyr Ser Ile Asn Ser Gly Val Ala Ser Asn
290                 295                 300

Ala Ala Val Ala Thr Gly Arg Tyr Pro Glu Asp Ser Tyr Gln Gly Gly
305                 310                 315                 320

Asn Pro Trp Tyr Leu Thr Thr Phe Ala Val Ala Glu Gln Leu Tyr Asp
            325                 330                 335

Ala Leu Asn Val Trp Glu Ser Gln Gly Ser Leu Glu Val Thr Ser Thr
            340                 345                 350

Ser Leu Ala Phe Phe Gln Gln Phe Ser Ser Gly Val Thr Ala Gly Thr
            355                 360                 365

Tyr Ser Ser Ser Ser Thr Tyr Ser Thr Leu Thr Ser Ala Ile Lys
            370                 375                 380

Asn Phe Ala Asp Gly Phe Val Ala Ile Asn Ala Lys Tyr Thr Pro Ser
385                 390                 395                 400

Asn Gly Gly Leu Ala Glu Gln Tyr Ser Lys Ser Asp Gly Ser Pro Leu
            405                 410                 415

Ser Ala Val Asp Leu Thr Trp Ser Tyr Ala Ser Ala Leu Thr Ala Phe
            420                 425                 430

Glu Ala Arg Asn Asn Thr Gln Phe Ala Gly Trp Gly Ala Ala Gly Leu
            435                 440                 445

Thr Val Pro Ser Ser Cys Ser Gly Asn Ser Gly Pro Thr Val Ala
450                 455                 460

Val Thr Phe Asn Val Asn Ala Glu Thr Val Trp Gly Glu Asn Ile Tyr
465                 470                 475                 480

Leu Thr Gly Ser Val Asp Ala Leu Glu Asn Trp Ser Ala Asp Asn Ala
            485                 490                 495

Leu Leu Leu Ser Ser Ala Asn Tyr Pro Thr Trp Ser Ile Thr Val Asn
            500                 505                 510

Leu Pro Ala Ser Thr Ala Ile Glu Tyr Lys Tyr Ile Arg Lys Asn Asn
            515                 520                 525

Gly Ala Val Thr Trp Glu Ser Asp Pro Asn Asn Ser Ile Thr Thr Pro
530                 535                 540

Ala Ser Gly Ser Thr Thr Glu Asn Asp Thr Trp Arg
545                 550                 555

<210> SEQ ID NO 13
<211> LENGTH: 559
<212> TYPE: PRT
<213> ORGANISM: Gloeophyllum trabeum

<400> SEQUENCE: 13

Gln Ser Val Asp Ser Tyr Val Gly Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ala Ala Gly Val Val Val Ala Ser Pro Ser Lys Ser Asp Pro Asp Tyr
            35                  40                  45

Trp Tyr Thr Trp Thr Arg Asp Ser Ser Leu Val Phe Lys Ser Leu Ile
50                  55                  60

Asp Gln Tyr Thr Thr Gly Ile Asp Ser Thr Ser Ser Leu Arg Ser Leu
65                  70                  75                  80

Ile Asp Ser Phe Val Ile Ala Glu Ala Asn Ile Gln Gln Val Ser Asn
            85                  90                  95
```

```
Pro Ser Gly Thr Leu Thr Thr Gly Gly Leu Gly Glu Pro Lys Phe Asn
            100                 105                 110

Val Asp Glu Thr Ala Phe Thr Gly Ala Trp Gly Arg Pro Gln Arg Asp
            115                 120                 125

Gly Pro Ala Leu Arg Ala Thr Ala Leu Ile Thr Tyr Gly Asn Trp Leu
            130                 135                 140

Leu Ser Asn Gly Asn Thr Thr Trp Val Thr Ser Thr Leu Trp Pro Ile
145                 150                 155                 160

Ile Gln Asn Asp Leu Asn Tyr Val Val Gln Tyr Trp Asn Gln Thr Thr
                165                 170                 175

Phe Asp Leu Trp Glu Glu Val Asn Ser Ser Phe Phe Thr Thr Ala
            180                 185                 190

Val Gln His Arg Ala Leu Arg Glu Gly Ala Ala Phe Ala Thr Lys Ile
            195                 200                 205

Gly Gln Thr Ser Ser Val Ser Ser Tyr Thr Thr Gln Ala Ala Asn Leu
            210                 215                 220

Leu Cys Phe Leu Gln Ser Tyr Trp Asn Pro Thr Ser Gly Tyr Ile Thr
225                 230                 235                 240

Ala Asn Thr Gly Gly Gly Arg Ser Gly Lys Asp Ala Asn Thr Leu Leu
                245                 250                 255

Ala Ser Ile His Thr Tyr Asp Pro Ser Ala Gly Cys Asp Ala Thr Thr
                260                 265                 270

Phe Gln Pro Cys Ser Asp Lys Ala Leu Ser Asn Leu Lys Val Tyr Val
            275                 280                 285

Asp Ser Phe Arg Ser Val Tyr Ser Ile Asn Ser Gly Ile Ala Ser Asn
            290                 295                 300

Ala Ala Val Ala Thr Gly Arg Tyr Pro Glu Asp Ser Tyr Gln Gly Gly
305                 310                 315                 320

Asn Pro Trp Tyr Leu Thr Thr Phe Ala Val Ala Glu Gln Leu Tyr Asp
                325                 330                 335

Ala Leu Asn Val Trp Ala Ala Gln Gly Ser Leu Asn Val Thr Ser Ile
            340                 345                 350

Ser Leu Pro Phe Phe Gln Gln Phe Ser Ser Val Thr Ala Gly Thr
            355                 360                 365

Tyr Ala Ser Ser Ser Thr Thr Tyr Thr Thr Leu Thr Ser Ala Ile Lys
370                 375                 380

Ser Phe Ala Asp Gly Phe Val Ala Ile Asn Ala Gln Tyr Thr Pro Ser
385                 390                 395                 400

Asn Gly Gly Leu Ala Glu Gln Phe Ser Arg Ser Asn Gly Ala Pro Val
                405                 410                 415

Ser Ala Val Asp Leu Thr Trp Ser Tyr Ala Ser Ala Leu Thr Ala Phe
            420                 425                 430

Glu Ala Arg Asn Asn Thr Gln Phe Ala Gly Trp Gly Ala Val Gly Leu
            435                 440                 445

Thr Val Pro Thr Ser Cys Ser Ser Asn Ser Gly Gly Gly Gly Ser
            450                 455                 460

Thr Val Ala Val Thr Phe Asn Val Asn Ala Gln Thr Val Trp Gly Glu
465                 470                 475                 480

Asn Ile Tyr Ile Thr Gly Ser Val Asp Ala Leu Ser Asn Trp Ser Pro
                485                 490                 495

Asp Asn Ala Leu Leu Leu Ser Ser Ala Asn Tyr Pro Thr Trp Ser Ile
            500                 505                 510
```

```
Thr Val Asn Leu Pro Ala Ser Thr Ala Ile Gln Tyr Lys Tyr Ile Arg
        515                 520                 525

Lys Asn Asn Gly Ala Val Thr Trp Glu Ser Asp Pro Asn Asn Ser Ile
530                 535                 540

Thr Thr Pro Ala Ser Gly Ser Val Thr Glu Asn Asp Thr Trp Arg
545                 550                 555

<210> SEQ ID NO 14
<211> LENGTH: 583
<212> TYPE: PRT
<213> ORGANISM: Artificial
<220> FEATURE:
<223> OTHER INFORMATION: Alpha amylase core from Rhizomucor pusilus with
      linker and starch binding domain from A. niger glucoamylase

<400> SEQUENCE: 14

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
    130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Ala Gly Val
        195                 200                 205

Phe Ala Thr Gly Glu Val Phe Asn Gly Asp Pro Ala Tyr Val Gly Pro
    210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
    275                 280                 285

Ser Asp Lys Ala Leu Phe Lys Asn Ala Leu Thr Tyr Val Leu Leu Gly
    290                 295                 300

Glu Gly Ile Pro Ile Val Tyr Tyr Gly Ser Glu Gln Gly Phe Ser Gly
305                 310                 315                 320
```

```
Gly Ala Asp Pro Ala Asn Arg Glu Val Leu Trp Thr Thr Asn Tyr Asp
            325                 330                 335

Thr Ser Ser Asp Leu Tyr Gln Phe Ile Lys Thr Val Asn Ser Val Arg
        340                 345                 350

Met Lys Ser Asn Lys Ala Val Tyr Met Asp Ile Tyr Val Gly Asp Asn
    355                 360                 365

Ala Tyr Ala Phe Lys His Gly Asp Ala Leu Val Val Leu Asn Asn Tyr
370                 375                 380

Gly Ser Gly Ser Thr Asn Gln Val Ser Phe Val Ser Gly Lys Phe
385                 390                 395                 400

Asp Ser Gly Ala Ser Leu Met Asp Ile Val Ser Asn Ile Thr Thr Thr
                405                 410                 415

Val Ser Ser Asp Gly Thr Val Thr Phe Asn Leu Lys Asp Gly Leu Pro
            420                 425                 430

Ala Ile Phe Thr Ser Ala Thr Gly Gly Thr Thr Thr Ala Thr Pro
        435                 440                 445

Thr Gly Ser Gly Ser Val Thr Ser Thr Ser Lys Thr Thr Ala Thr Ala
    450                 455                 460

Ser Lys Thr Ser Thr Ser Thr Ser Thr Ser Cys Thr Thr Pro Thr
465                 470                 475                 480

Ala Val Ala Val Thr Phe Asp Leu Thr Ala Thr Thr Thr Tyr Gly Glu
                485                 490                 495

Asn Ile Tyr Leu Val Gly Ser Ile Ser Gln Leu Gly Asp Trp Glu Thr
            500                 505                 510

Ser Asp Gly Ile Ala Leu Ser Ala Asp Lys Tyr Thr Ser Ser Asp Pro
        515                 520                 525

Leu Trp Tyr Val Thr Val Thr Leu Pro Ala Gly Glu Ser Phe Glu Tyr
    530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Thr Asp Thr Trp Arg
            580

<210> SEQ ID NO 15
<211> LENGTH: 481
<212> TYPE: PRT
<213> ORGANISM: Artificial
<220> FEATURE:
<223> OTHER INFORMATION: Synthetic construct

<400> SEQUENCE: 15

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Ala Ile Ser
        35                  40                  45

Gln Ala Asp Val Gly Tyr Gly Ala Tyr Asp Leu Tyr Asp Leu Gly Glu
    50                  55                  60

Phe His Gln Lys Gly Thr Val Arg Thr Lys Tyr Gly Thr Lys Gly Glu
65                  70                  75                  80

Leu Gln Ser Ala Ile Lys Ser Leu His Ser Arg Asp Ile Asn Val Tyr
                85                  90                  95
```

```
Gly Asp Val Val Ile Asn His Lys Ala Gly Asp Ala Thr Glu Asp
                100                 105                 110
Val Thr Ala Val Glu Val Asp Pro Ala Asp Arg Asn Arg Val Ile Ser
            115                 120                 125
Gly Glu His Leu Ile Lys Ala Trp Thr His Phe His Phe Pro Gly Arg
        130                 135                 140
Gly Ser Thr Tyr Ser Asp Phe Lys Trp Tyr Trp Tyr His Phe Asp Gly
145                 150                 155                 160
Thr Asp Trp Asp Glu Ser Arg Lys Leu Asn Arg Ile Tyr Lys Phe Gln
                165                 170                 175
Gly Lys Thr Trp Asp Trp Glu Val Ser Asn Glu Phe Gly Asn Tyr Asp
            180                 185                 190
Tyr Leu Met Tyr Ala Asp Phe Asp Tyr Asp His Pro Asp Val Val Ala
        195                 200                 205
Glu Ile Lys Arg Trp Gly Thr Trp Tyr Ala Asn Glu Leu Gln Leu Asp
    210                 215                 220
Gly Phe Arg Leu Asp Ala Val Lys His Ile Lys Phe Ser Phe Leu Arg
225                 230                 235                 240
Asp Trp Val Asn His Val Arg Glu Lys Thr Gly Lys Glu Met Phe Thr
                245                 250                 255
Val Ala Glu Tyr Trp Ser Asn Asp Leu Gly Ala Leu Glu Asn Tyr Leu
            260                 265                 270
Asn Lys Thr Asn Phe Asn His Ser Val Phe Asp Val Pro Leu His Tyr
        275                 280                 285
Gln Phe His Ala Ala Ser Thr Gln Gly Gly Gly Tyr Asp Met Arg Lys
    290                 295                 300
Leu Leu Asn Gly Thr Val Val Ser Lys His Pro Leu Lys Ser Val Thr
305                 310                 315                 320
Phe Val Asp Asn His Asp Thr Gln Pro Gly Gln Ser Leu Glu Ser Thr
                325                 330                 335
Val Gln Thr Trp Phe Lys Pro Leu Ala Tyr Ala Phe Ile Leu Thr Arg
            340                 345                 350
Glu Ser Gly Tyr Pro Gln Val Phe Tyr Gly Asp Met Tyr Gly Thr Lys
        355                 360                 365
Gly Asp Ser Gln Arg Glu Ile Pro Ala Leu Lys His Lys Ile Glu Pro
    370                 375                 380
Ile Leu Lys Ala Arg Lys Gln Tyr Ala Tyr Gly Ala Gln His Asp Tyr
385                 390                 395                 400
Phe Asp His His Asp Ile Val Gly Trp Thr Arg Glu Gly Asp Ser Ser
                405                 410                 415
Val Ala Asn Ser Gly Leu Ala Ala Leu Ile Thr Asp Gly Pro Gly Gly
            420                 425                 430
Ala Lys Arg Met Tyr Val Gly Arg Gln Asn Ala Gly Glu Thr Trp His
        435                 440                 445
Asp Ile Thr Gly Asn Arg Ser Glu Pro Val Val Ile Asn Ser Glu Gly
    450                 455                 460
Trp Gly Glu Phe His Val Asn Gly Gly Ser Val Ser Ile Tyr Val Gln
465                 470                 475                 480
Arg

<210> SEQ ID NO 16
<211> LENGTH: 481
<212> TYPE: PRT
```

<213> ORGANISM: Artificial
<220> FEATURE:
<223> OTHER INFORMATION: Synthetic construct

<400> SEQUENCE: 16

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Ala Ile Ser
        35                  40                  45

Gln Ala Asp Val Gly Tyr Gly Ala Tyr Asp Leu Tyr Asp Leu Gly Glu
    50                  55                  60

Phe Trp Gln Lys Gly Thr Val Arg Thr Lys Tyr Gly Thr Lys Gly Glu
65                  70                  75                  80

Leu Gln Ser Ala Ile Lys Ser Leu His Ser Arg Asp Ile Asn Val Tyr
                85                  90                  95

Gly Asp Val Val Ile Asn His Lys Ala Gly Ala Asp Ala Thr Glu Asp
            100                 105                 110

Val Thr Ala Val Glu Val Asp Pro Ala Asp Arg Asn Arg Val Ile Ser
        115                 120                 125

Gly Glu His Leu Ile Lys Ala Trp Thr His Phe His Phe Pro Gly Arg
    130                 135                 140

Gly Ser Thr Tyr Ser Asp Phe Lys Trp Tyr Trp Tyr His Phe Asp Gly
145                 150                 155                 160

Thr Asp Trp Asp Glu Ser Arg Lys Leu Asn Arg Ile Tyr Leu Phe Gln
                165                 170                 175

Gly Lys Thr Trp Asp Trp Pro Val Ser Asn Glu Phe Gly Asn Tyr Asp
            180                 185                 190

Tyr Leu Met Tyr Ala Asp Tyr Asp Tyr Asp Pro Asp Val Val Ala
        195                 200                 205

Glu Ile Thr Arg Trp Gly Thr Trp Tyr Ala Asn Glu Leu Gln Leu Asp
    210                 215                 220

Gly Phe Arg Leu Asp Ala Val Lys His Ile Lys Phe Ser Phe Leu Arg
225                 230                 235                 240

Asp Trp Val Asn His Val Arg Glu Lys Thr Gly Lys Glu Met Phe Thr
                245                 250                 255

Val Ala Glu Tyr Trp Ser Asn Asp Leu Gly Ala Leu Glu Asn Tyr Leu
            260                 265                 270

Asn Lys Thr Asn Phe Asn His Ser Val Phe Asp Val Pro Leu His Tyr
        275                 280                 285

Gln Phe His Ala Ala Ser Thr Gln Gly Gly Gly Tyr Asp Met Arg Lys
    290                 295                 300

Leu Leu Asn Gly Thr Val Val Ser Lys His Pro Leu Lys Ser Val Thr
305                 310                 315                 320

Phe Val Asp Asn His Asp Thr Gln Pro Gly Gln Ser Leu Glu Ser Thr
                325                 330                 335

Val Gln Thr Trp Phe Lys Pro Leu Ala Tyr Ala Phe Ile Leu Thr Arg
            340                 345                 350

Glu Ser Gly Tyr Pro Ser Val Phe Tyr Gly Asp Met Tyr Gly Thr Lys
        355                 360                 365

Gly Asp Ser Gln Arg Glu Ile Pro Ala Leu Lys His Lys Ile Glu Pro
    370                 375                 380

Ile Leu Lys Ala Arg Lys Gln Tyr Ala Tyr Gly Ala Gln His Asp Tyr

```
                385                 390                 395                 400
Phe Asp His His Asp Ile Val Gly Trp Thr Arg Glu Gly Val Ser Ser
                    405                 410                 415

Val Ala Asn Ser Gly Leu Ala Ala Leu Ile Thr Asp Gly Pro Gly Gly
                420                 425                 430

Ala Lys Trp Met Tyr Val Gly Arg Gln Asn Ala Gly Glu Thr Trp His
                435                 440                 445

Asp Ile Thr Gly Asn Arg Ser Glu Pro Val Val Ile Asn Ser Glu Gly
            450                 455                 460

Trp Gly Glu Phe His Val Asn Gly Gly Ser Val Ser Ile Tyr Val Gln
465                 470                 475                 480

Arg

<210> SEQ ID NO 17
<211> LENGTH: 483
<212> TYPE: PRT
<213> ORGANISM: Bacillus licheniformis

<400> SEQUENCE: 17

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
                20                  25                  30

Ala Glu His Gly Ile Thr Ala Val Trp Ile Pro Pro Ala Tyr Lys Gly
            35                  40                  45

Thr Ser Gln Ala Asp Val Gly Tyr Gly Ala Tyr Asp Leu Tyr Asp Leu
        50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
```

-continued

```
            275                 280                 285
His Tyr Gln Phe His Ala Ala Ser Thr Gln Gly Gly Gly Tyr Asp Met
290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
    450                 455                 460

Glu Gly Trp Gly Glu Phe His Val Asn Gly Gly Ser Val Ser Ile Tyr
465                 470                 475                 480

Val Gln Arg

<210> SEQ ID NO 18
<211> LENGTH: 484
<212> TYPE: PRT
<213> ORGANISM: Bacillus stearothermophilus

<400> SEQUENCE: 18

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
```

-continued

```
                165                 170                 175
Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
            195                 200                 205

Pro Glu Val Val Thr Glu Leu Lys Asn Trp Gly Lys Trp Tyr Val Asn
            210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
                260                 265                 270

Leu His Asn Tyr Ile Thr Lys Thr Asp Gly Thr Met Ser Leu Phe Asp
        275                 280                 285

Ala Pro Leu His Asn Lys Phe Tyr Thr Ala Ser Lys Ser Gly Gly Ala
        290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
                340                 345                 350

Phe Ile Leu Thr Arg Gln Glu Gly Tyr Pro Cys Val Phe Tyr Gly Asp
                355                 360                 365

Tyr Tyr Gly Ile Pro Gln Tyr Asn Ile Pro Ser Leu Lys Ser Lys Ile
        370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
                420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
        450                 455                 460

Asp Gly Trp Gly Glu Phe Lys Val Asn Gly Gly Ser Val Ser Val Trp
465                 470                 475                 480

Val Pro Arg Lys
```

ALPHA-AMYLASE VARIANTS AND POLYNUCLEOTIDES ENCODING SAME

CROSS-REFERENCE TO RELATED APPLICATIONS

This application is a 35 U.S.C. 371 national application of international application no. PCT/US2018/064415 filed Dec. 7, 2018, which claims priority or the benefit under 35 U.S.C. 119 of U.S. application Nos. 62/596,231 and 62/765,268 filed Dec. 8, 2017 and Aug. 20, 2018, respectively, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to alpha-amylase variants, polynucleotides encoding the variants, methods of producing the variants, and methods of using the variants.

Description of the Related Art

Alpha-amylases (alpha-1,4-glucan-4-glucanohydrolases, E.C. 3.2.1.1) constitute a group of enzymes, which catalyze hydrolysis of starch and other linear and branched 1,4-glucosidic oligo- and polysaccharides.

Alpha-amylases are used commercially for a variety of purposes such as in the initial stages of starch processing (e.g., liquefaction); in wet milling processes; and in alcohol production from carbohydrate sources. They are also used as cleaning agents or adjuncts in detergent matrices; in the textile industry for starch desizing; in baking applications; in the beverage industry; in oil fields in drilling processes; in recycling processes, e.g., for de-inking paper; and in animal feed.

Fermentation products, such as ethanol, are typically produced by first grinding starch-containing material in a dry-grind or wet-milling process, then degrading the material into fermentable sugars using enzymes and finally converting the sugars directly or indirectly into the desired fermentation product using a fermenting organism. Liquid fermentation products are recovered from the fermented mash (often referred to as "beer mash"), e.g., by distillation, which separate the desired fermentation product from other liquids and/or solids.

For an alpha-amylase to be used in a starch liquefaction process it is of particular interest that it is thermostable and able to function at low pH and low calcium concentrations. Altered $Ca^{2+}$ stability means the stability of the enzyme under $Ca^{2+}$ depletion has been improved, i.e., higher stability. In the context of the present invention, mutations (including amino acid substitutions) of importance are mutations achieving altered $Ca^{2+}$ stability, in particular improved $Ca^{2+}$ stability, i.e., higher stability, at especially low pH (i.e., pH 4-6).

WO2000/060059 discloses Termamyl like alpha-amylase variants having increased stability at low $Ca^{2+}$ levels. WO2013/057143 and WO2013/057141 disclose variants of alpha-amylases from *Bacillus liquefaciens* having improved properties such as increased stability at low calcium concentrations.

An alpha-amylase from *Bacillus stearothermophilus* is disclosed in WO 99/19467 as SEQ ID NO: 3, and variants thereof have been disclosed in WO1996/023873, and WO1999/019467. Further variants of the *Bacillus stearothermophilus* alpha-amylase are disclosed in WO 2011/082425.

WO 2012/088303 (Novozymes) discloses processes for producing fermentation products by liquefying starch-containing material at a pH in the range from 4.5-5.0 at a temperature in the range from 80-90° C. using a combination of alpha-amylase having a T½ (min) at pH 4.5, 85° C., 0.12 mM CaCl2)) of at least 10 and a protease having a thermostability value of more than 20% determined as Relative Activity at 80° C./70° C.; followed by saccharification and fermentation.

WO 2013/082486 (Novozymes) discloses processes for producing fermentation products by liquefying starch-containing material at a pH in the range between from above 5.0-7.0 at a temperature above the initial gelatinization temperature using an alpha-amylase variant.

U.S. Pat. No. 8,084,240 discloses the E188P substitution in a *Bacillus stearothermophilus* alpha-amylase resulting in increased stability. WO2009/061381 describes substitutions at position 242 resulting in improved performance when S is substituted with A, Q, E, D, or M whereas other substitutions resulted in less activity compared to wild type.

WO 2017/015329 discloses variants of a *Bacillus stearothermophilus* alpha-amylase. It is shown that when using said variants in a liquefaction process it results in a reduced viscosity of a liquefied mash from ground corn performed at pH 4.8 and 85° C. for 2 hours, compared to the control (parent) alpha-amylase.

It is an object of the present invention to provide alpha-amylase variants having an increased stability at low pH and/or at high temperature.

The present invention provides alpha-amylase variants with improved properties compared to its parent.

SUMMARY OF THE INVENTION

The present invention relates to an alpha-amylase variant comprising substitutions at positions corresponding to positions 268 and 293 of SEQ ID NO: 1, in particular substitutions selected from the group consisting of: 268G+293Y; 268G+293F; 268G+293W; 268G+293H; 268G+293A; 268G+293Q; 268A+293Y; 268A+293F; 268A+293W; 268A+293H; 268A+293A; 268A+293Q; 268P+293Y; 268P+293F; 268P+293W; 268P+293H; 268P+293A; 268P+293Q; 268S+293Y; 268S+293F; 268S+293W; 268S+293H; 268S+293A; 268S+293Q; 268T+293Y; 268T+293F; 268T+293W; 268T+293H; 268T+293A; 268T+293Q; 268V+293Y; 268V+293F; 268V+293W; 268V+293H; 268V+293A; 268V+293Q; 268I+293Y; 268I+293F; 268I+293W; 268I+293H; 268I+293A; 268I+293Q; 268L+293Y; 268L+293F; 268L+293W; 268L+293H; 268L+293A; 268L+293Q; 268M+293Y; 268M+293F; 268M+293W; 268M+293H; 268M+293A; 268M+293Q; and wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of SEQ ID NO: 1, SEQ ID NO: 2, SEQ ID NO: 3, SEQ ID NO: 4, and SEQ ID NO: 18.

The present invention also relates to polynucleotides encoding the variants; nucleic acid constructs, vectors, and host cells comprising the polynucleotides; and methods of producing the variants.

Furthermore, the invention relates to compositions comprising the alpha-amylase variant of the invention.

The present invention also relates to methods of producing an alpha-amylase variant of the invention, comprising:
a) cultivating the host cell of the invention under conditions suitable for expression of the variant; and
b) optionally recovering the variant.

The present invention also relates to a process for producing a syrup from starch-containing material comprising the steps of:
a) liquefying the starch-containing material at a temperature above the initial gelatinization temperature in the presence of a variant alpha-amylase according to the invention or a composition of the invention; and
b) saccharifying the product of step a) in the presence of a glucoamylase.

DEFINITIONS

Alpha-amylase variants: Alpha-amylases (E.C. 3.2.1.1) are a group of enzymes which catalyze the hydrolysis of starch and other linear and branched 1,4 glucosidic oligo- and polysaccharides. The skilled person will know how to determine alpha-amylase activity. It may be determined according to the procedure described in the Examples, e.g., by the PNP-G7 assay or the EnzCheck assay. In one aspect, the variants of the present invention have at least 20%, e.g., at least 40%, at least 50%, at least 60%, at least 70%, at least 80%, at least 90%, at least 95%, or at least 100% of the alpha-amylase activity of the polypeptide of SEQ ID NO: 1-5. In one aspect, a variant of the present application has at least 20%, e.g., at least 40%, at least 50%, at least 60%, at least 70%, at least 80%, at least 90%, at least 95%, or at least 100% of the alpha-amylase activity of its parent.

In a further embodiment the variant alpha-amylases of the invention have an increased stability compared to a parent alpha-amylase, particularly the parent disclosed as SEQ ID NO: 1-5, and 18, and wherein the increased stability is measured as residual alpha-amylase activity after heast shock determined by any suitable alpha-amylase assay and at a suitable temperature. Such assays will be known to the skilled person. Suitable assays have been included in the examples. Such increased stability may include increased thermo-stability at pH 4.5-5.0 over the parent alpha-amylase. Residual activity (% RA) can be calculated as Activity in heat stressed sample/Activity in control sample*100. Increased thermo-stability may be expressed as Half-life improvement factor (HIF). Assuming logarithmic decay, half life time (T½ (min)) was calculated using the equation: T½ (min)=T(min)*LN(0.5)/LN(% RA/100), where T is assay incubation time in minutes, and % RA is % residual activity determined in assay. Half-life improvement factor (HIF) was calculated as: Half-life improvement Factor (HIF) of variant=(half-life (T½) of the variant/half-life (T½) of the reference backbone). In one embodiment the variant alpha-amylases of the invention has a HIF of at least 1.1, at least 1.2, at least 1.3, at least 1.4, at least 1.5, at least 1.6, at least 1.7, at least 1.8, at least 1.9, at least 2.0.

In another embodiment the variant alpha-amylases according to the invention have increased thermo-stability at pH 4.5-5.0, particularly increased stability determined as an improvement factor (IF) over the parent alpha-amylase, particularly an improvement factor greater than 1.0 and wherein the improvement factor is calculated as the ratio of retained activity (measured as ratio of DP3/DP4+ at 91° C. to DP3/DP4+ at 85° C.) for a given variant to the retained activity of the parent alpha-amylase, more particularly the alpha-amylase of SEQ ID NO: 5. The improvement factor is at least 1.05, at least 1.1, at least 1.2, at least 1.3, at least 1.4, at least 1.5, at least 1.6. The skilled person will know how to modify the assay based on the themo-stabillity of the parent alpha-amylase. Thus, if the parent alpha-amylase is a wild type enzyme testing ratio of DP3/DP4+ at 91° C. compared to DP3/DP4+ at 85° C., may need to be performed at lower temperatures.

In another particular embodiment the variant alpha-amylases according to the invention have increased thermo-stability at pH 4.5-5.0, particularly increased stability determined as an improvement factor (IF) over the parent alpha-amylase, wherein the IF is determined as residual activity of the variant alpha-amylase (ratio of activity in a themo-stressed sample over activity in a sample incubated at 4° C.) over residual activity of the parent alpha-amylase (ratio of activity in a themo-stressed sample over activity in a sample incubated at 4° C.), in particular the variants have an IF of at least 1.1, at least 1.2, at least 1.3, at least 1.4, at least 1.5, at least 1.6, at least 1.7, at least 1.8, at least 1.9, at least 2.0, in particular compared to the parent alpha-amylase of SEQ ID NO: 1, SEQ ID NO: 2, SEQ ID NO: 3, SEQ ID NO: 4, SEQ ID NO: 5, and SEQ ID NO: 18.

Residual activity may be measured using the EnzCheck assay or the Phadebas assay after, e.g., 40 min heat-stress at 75° C., or 15-30 min incubation at 90-95° C., pH 4.5-5.0, 5 ppm $Ca^{2+}$. See examples for details. The residual activity is in one embodiment at least 10% improved, at least 15% improved, particularly at least 20% improved over the parent.

In another embodiment the variant has increased specific activity compared to the parent alpha-amylase measured in the same assay under the same conditions, particularly compared to a parent alpha-amylase selected from the group of SEQ ID NO: 1, SEQ ID NO: 2, SEQ ID NO: 3, SEQ ID NO: 4, SEQ ID NO: 5, and SEQ ID NO: 18.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has alpha-amylase activity.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to, increased stability, e.g., increased thermo-stability measured as residual alpha-amylase activity after heast shock determined by any suitable alpha-amylase assay. Such assays will be known to the skilled person. Suitable assays have been included in the examples. Such increased stability may include increased thermo-stability at pH 4.5-5.0 over the parent alpha-amylase. Residual activity (% RA) can be calculated as Activity in heat stressed sample/Activity in control sample*100. Increased thermo-stability may be expressed as Half-life improvement factor (HIF). Assuming logarithmic decay, half life time (T½ (min)) was calculated using the equation: T½ (min)=T(min) *LN(0.5)/LN(% RA/100), where T is assay incubation time in minutes, and % RA is % residual activity determined in assay. Half-life improvement factor (HIF) was calculated as: Half-life improvement Factor (HIF) of variant=(half-life (T½) of the variant/half-life (T½) of the reference backbone). In one embodiment the variant alpha-amylases of the invention has a HIF of at least 1.1, at least 1.2, at least 1.3, at least 1.4, at least 1.5, at least 1.6, at least 1.7, at least 1.8, at least 1.9, at least 2.0.

In another embodiment the variant alpha-amylases according to the invention have increased thermo-stability at pH 4.5-5.0, particularly increased stability determined as an improvement factor (IF) over the parent alpha-amylase, particularly an improvement factor greater than 1.0 and wherein the improvement factor is calculated as the ratio of retained activity (measured as ratio of DP3/DP4+ at 91° C. to DP3/DP4+ at 85° C.) for a given variant to the retained activity of the parent alpha-amylase, more particularly the alpha-amylase of SEQ ID NO: 5. The improvement factor is at least 1.05, at least 1.1, at least 1.2, at least 1.3, at least 1.4, at least 1.5, at least 1.6. The skilled person will know how to modify the assay based on the themo-stabillity of the parent alpha-amylase. Thus, if the parent alpha-amylase is a wild type enzyme testing ratio of DP3/DP4+ at 91° C. compared to DP3/DP4+ at 85° C., may need to be performed at lower temperatures.

In another particular embodiment the variant alpha-amylases according to the invention have increased thermo-stability at pH 4.5-5.0, particularly increased stability determined as an improvement factor (IF) over the parent alpha-amylase, wherein the IF is determined as residual activity of the variant alpha-amylase (ratio of activity in a themo-stressed sample over activity in a sample incubated at 4° C.) over residual activity of the parent alpha-amylase (ratio of activity in a themo-stressed sample over activity in a sample incubated at 4° C.), in particular the variants have an IF of at least 1.1, at least 1.2, at least 1.3, at least 1.4, at least 1.5, at least 1.6, at least 1.7, at least 1.8, at least 1.9, at least 2.0, in particular compared to the parent alpha-amylase of SEQ ID NO: 1, SEQ ID NO: 2, SEQ ID NO: 3, SEQ ID NO: 4, SEQ ID NO: 5, and SEQ ID NO: 18.

Residual activity may be measured using the EnzCheck assay or the Phadebas assay after, e.g., 40 min heat-stress at 75° C., or 15-30 min heat-stress at 90-95° C., pH 4.5-5.0, 5 ppm $Ca^{2+}$. See examples for details.

The residual activity is in one embodiment at least 10% improved, at least 15% improved, particularly at least 20% improved over the parent.

In another embodiment the variant has increased specific activity compared to the parent alpha-amylase measured in the same assay under the same conditions, particularly compared to a parent alpha-amylase selected from the group of SEQ ID NO: 1, SEQ ID NO: 2, SEQ ID NO: 3, SEQ ID NO: 4, SEQ ID NO: 5, and SEQ ID NO: 18. Relevant assays for this purpose may be assays using natural starch, amylose or amylopectin combined with measuring formation of reducing ends, e.g., the Phadebas activity assay.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation.

It is known in the art that a host cell may produce a mixture of two of more different mature polypeptides (i.e., with a different C-terminal and/or N-terminal amino acid) expressed by the same polynucleotide. The wild type alpha-amylases disclosed herein, SEQ ID NO: 1, 2, 3, 6, 15, and 17 are well known in the art and are disclosed in their mature form.

Mature polypeptide coding sequence: The term "mature polypeptide coding sequence" means a polynucleotide that encodes a mature polypeptide having glucoamylase activity.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent alpha-amylase: The term "parent" or "parent alpha-amylase" means any polypeptide with alpha-amylase activity to which an alteration is made to produce the enzyme variants of the present invention.

S8A Protease: The term "S8A protease" means an S8 protease belonging to subfamily A. Subtilisins, EC 3.4.21.62, are a subgroup in subfamily S8A. The S8A protease hydrolyses the substrate Suc-Ala-Ala-Pro-Phe-pNA. The release of p-nitroaniline (pNA) results in an increase of absorbance at 405 nm and is proportional to the enzyme activity.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of
Alignment–Total Number of Gaps in Alignment)

Variant: The term "variant" means a polypeptide having glucoamylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

In one embodiment the parent alpha-amylase is selected from the polypeptide of SEQ ID NO: 1, 2, 3, 4, 5 or 18.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type alpha-amylase: The term "wild-type" alpha-amylase means an alpha-amylase expressed by a naturally occurring microorganism, such as a bacterium, yeast, or filamentous fungus found in nature.

Conventions for Designation of Variants

A wild type alpha-amylase from *Bacillus stearothermophilus* is disclosed in WO 99/19467 as SEQ ID NO: 3 (SEQ ID NO: 1 in the present disclosure). For purposes of the present invention, the mature polypeptide disclosed in SEQ ID NO: 1 is used to determine the corresponding amino acid residue in another alpha-amylase unless other wise stated. The amino acid sequence of another alpha-amylase is aligned with the polypeptide disclosed in SEQ ID NO: 1, and based on the alignment, the amino acid position number corresponding to any amino acid residue in the polypeptide disclosed as SEQ ID NO: 1 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another alpha-amylase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 1 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, Proteins 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G - K - A |

Multiple alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to alpha-amylase variant comprising substitutions at positions corresponding to positions 268 and 293 of SEQ ID NO: 1, in particular substitutions selected from the group consisting of:
268G+293Y; 268G+293F; 268G+293W; 268G+293H; 268G+293A; 268G+293Q; 268A+293Y; 268A+293F; 268A+293W; 268A+293H; 268A+293A; 268A+293Q; 268P+293Y; 268P+293F; 268P+293W; 268P+293H; 268P+293A; 268P+293Q; 268S+293Y; 268S+293F; 268S+293W; 268S+293H; 268S+293A; 268S+293Q; 268T+293Y; 268T+293F; 268T+293W; 268T+293H; 268T+293A; 268T+293Q; 268V+293Y; 268V+293F; 268V+293W; 268V+293H; 268V+293A; 268V+293Q; 268I+293Y; 268I+293F; 268I+293W; 268I+293H; 268I+293A; 268I+293Q; 268L+293Y; 268L+293F; 268L+293W; 268L+293H; 268L+293A; 268L+293Q; 268M+293Y; 268M+293F; 268M+293W;

268M+293H; 268M+293A; 268M+293Q; and wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of SEQ ID NO: 1, SEQ ID NO: 2, SEQ ID NO: 3, SEQ ID NO: 4, and SEQ ID NO: 18.

Variants

The variants of the present invention have increased thermo-stability compared to a parent alpha-amylase, particularly a parent alpha-amylase selected from SEQ ID NO: 1, SEQ ID NO: 2, SEQ ID NO: 3, SEQ ID NO: 4, and SEQ ID NO: 18, and wherein the variants comprise at least substitutions corresponding to position 268 and 293 of SEQ ID NO: 1, in particular substitutions selected from the group consisting of:
268G+293Y; 268G+293F; 268G+293W; 268G+293H; 268G+293A; 268G+293Q; 268A+293Y; 268A+293F; 268A+293W; 268A+293H; 268A+293A; 268A+293Q; 268P+293Y; 268P+293F; 268P+293W; 268P+293H; 268P+293A; 268P+293Q; 268S+293Y; 268S+293F; 268S+293W; 268S+293H; 268S+293A; 268S+293Q; 268T+293Y; 268T+293F; 268T+293W; 268T+293H; 268T+293A; 268T+293Q; 268V+293Y; 268V+293F; 268V+293W; 268V+293H; 268V+293A; 268V+293Q; 268I+293Y; 268I+293F; 268I+293W; 268I+293H; 268I+293A; 268I+293Q; 268L+293Y; 268L+293F; 268L+293W; 268L+293H; 268L+293A; 268L+293Q; 268M+293Y; 268M+293F; 268M+293W; 268M+293H; 268M+293A; 268M+293Q. The starting amino acid at the corresponding positions to 268 and 293 of SEQ ID NO: 1 will depend on the parent Alpha-amylase, thus for SEQ ID NO: 1 the amino acid in position 268 is Y, and in position 293 it is N. In particular the increased thermo-stability is measured as residual alpha-amylase activity after heat-stress compared to a parent alpha-amylase, particularly a parent amylase selected from the group consisting of SEQ ID NO: 1, SEQ ID NO: 2, SEQ ID NO: 3, SEQ ID NO: 4, and SEQ ID NO: 5.

The increased thermo-stability may be determined using any suitable alpha-amylase assay, e.g., it may be determined as a Half-life Improvement Factor (HIF), wherein HIF is at least 1.1, at least 1.2, at least 1.3, at least 1.4, at least 1.5, at least 1.6, at least 1.7, at least 1.8, at least 1.9, at least 2.0. In another embodiment, increased thermo-stability may be determined as an improvement factor (IF) over the parent alpha-amylase, wherein the IF is determined as residual activity of the variant alpha-amylase (ratio of activity in a themo-stressed sample over activity in a sample incubated at 4° C.) over residual activity of the parent alpha-amylase (ratio of activity in a themo-stressed sample over activity in a sample incubated at 4° C.), in particular the variants have an IF of at least 1.1, at least 1.2, at least 1.3, at least 1.4, at least 1.5, at least 1.6, at least 1.7, at least 1.8, at least 1.9, at least 2.0 compared to the alpha-amylase of SEQ ID NO: 1, SEQ ID NO: 2, SEQ ID NO: 3, SEQ ID NO: 4, SEQ ID NO: 5, and SEQ ID NO: 18.

The variants of the invention may further have a substitution corresponding to T297N of SEQ ID NO: 1, particularly the variants comprises the substitutions Y268G+N293Y+T297N.

In one particular embodiment therefore the present invention relates to alpha-amylase variants comprising at least substitutions corresponding to position 268 and 293 of SEQ ID NO: 1, in particular substitutions selected from the group consisting of:
268G+293Y; 268G+293F; 268G+293W; 268G+293H; 268G+293A; 268G+293Q; 268A+293Y; 268A+293F; 268A+293W; 268A+293H; 268A+293A; 268A+293Q; 268P+293Y; 268P+293F; 268P+293W; 268P+293H; 268P+293A; 268P+293Q; 268S+293Y; 268S+293F; 268S+293W; 268S+293H; 268S+293A; 268S+293Q; 268T+293Y; 268T+293F; 268T+293W; 268T+293H; 268T+293A; 268T+293Q; 268V+293Y; 268V+293F; 268V+293W; 268V+293H; 268V+293A; 268V+293Q; 268I+293Y; 268I+293F; 268I+293W; 268I+293H; 268I+293A; 268I+293Q; 268L+293Y; 268L+293F; 268L+293W; 268L+293H; 268L+293A; 268L+293Q; 268M+293Y; 268M+293F; 268M+293W; 268M+293H; 268M+293A; 268M+293Q, and wherein the variant has at least 60%, at least 65%, at least 70%, at least 75%, at least 80%, at least 85%, at least 90%, at least 95%, at least 96%, at least 97%, at least 98%, or at least 99%, but less than 100% sequence identity to SEQ ID NO: 1, and wherein the variants have increased thermo-stability determined as an improvement factor (IF) over the parent alpha-amylase, wherein the IF is determined as residual activity of the variant alpha-amylase (ratio of activity in a themo-stressed sample over activity in a sample incubated at 4° C.) over residual activity of the parent alpha-amylase (ratio of activity in a themo-stressed sample over activity in a sample incubated at 4° C.), in particular the variants have an IF of at least 1.1, at least 1.2, at least 1.3, at least 1.4, at least 1.5, at least 1.6, at least 1.7, at least 1.8, at least 1.9, at least 2.0 compared to the alpha-amylase of SEQ ID NO: 1.

In another embodiment the present invention relates to alpha-amylase variants comprising at least substitutions corresponding to position 268 and 293 of SEQ ID NO: 1, in particular substitutions selected from the group consisting of:
268G+293Y; 268G+293F; 268G+293W; 268G+293H; 268G+293A; 268G+293Q; 268A+293Y; 268A+293F; 268A+293W; 268A+293H; 268A+293A; 268A+293Q; 268P+293Y; 268P+293F; 268P+293W; 268P+293H; 268P+293A; 268P+293Q; 268S+293Y; 268S+293F; 268S+293W; 268S+293H; 268S+293A; 268S+293Q; 268T+293Y; 268T+293F; 268T+293W; 268T+293H; 268T+293A; 268T+293Q; 268V+293Y; 268V+293F; 268V+293W; 268V+293H; 268V+293A; 268V+293Q; 268I+293Y; 268I+293F; 268I+293W; 268I+293H; 268I+293A; 268I+293Q; 268L+293Y; 268L+293F; 268L+293W; 268L+293H; 268L+293A; 268L+293Q; 268M+293Y; 268M+293F; 268M+293W; 268M+293H; 268M+293A; 268M+293Q, and wherein the variant has at least 60%, at least 65%, at least 70%, at least 75%, at least 80%, at least 85%, at least 90%, at least 95%, at least 96%, at least 97%, at least 98%, or at least 99%, but less than 100% sequence identity to SEQ ID NO: 2, and wherein the variants have increased thermo-stability determined as an improvement factor (IF) over the parent alpha-amylase, wherein the IF is determined as residual activity of the variant alpha-amylase (ratio of activity in a themo-stressed sample over activity in a sample incubated at 4° C.) over residual activity of the parent alpha-amylase (ratio of activity in a themo-stressed sample over activity in a sample incubated at 4° C.), in particular the variants have an IF of at least 1.1, at least 1.2, at least 1.3, at least 1.4, at least 1.5, at least 1.6, at least 1.7, at least 1.8, at least 1.9, at least 2.0 compared to the alpha-amylase of SEQ ID NO: 2.

In another embodiment the present invention relates to alpha-amylase variants comprising at least substitutions corresponding to position 268 and 293 of SEQ ID NO: 1, in particular substitutions selected from the group consisting of:
268G+293Y; 268G+293F; 268G+293W; 268G+293H; 268G+293A; 268G+293Q; 268A+293Y; 268A+293F; 268A+293W; 268A+293H; 268A+293A; 268A+293Q;

268P+293Y; 268P+293F; 268P+293W; 268P+293H; 268P+293A; 268P+293Q; 268S+293Y; 268S+293F; 268S+293W; 268S+293H; 268S+293A; 268S+293Q; 268T+293Y; 268T+293F; 268T+293W; 268T+293H; 268T+293A; 268T+293Q; 268V+293Y; 268V+293F; 268V+293W; 268V+293H; 268V+293A; 268V+293Q; 268I+293Y; 268I+293F; 268I+293W; 268I+293H; 268I+293A; 268I+293Q; 268L+293Y; 268L+293F; 268L+293W; 268L+293H; 268L+293A; 268L+293Q; 268M+293Y; 268M+293F; 268M+293W; 268M+293H; 268M+293A; 268M+293Q, and wherein the variant has at least 60%, at least 65%, at least 70%, at least 75%, at least 80%, at least 85%, at least 90%, at least 95%, at least 96%, at least 97%, at least 98%, or at least 99%, but less than 100% sequence identity to SEQ ID NO: 3, and wherein the variants have increased thermo-stability determined as an improvement factor (IF) over the parent alpha-amylase, wherein the IF is determined as residual activity of the variant alpha-amylase (ratio of activity in a themo-stressed sample over activity in a sample incubated at 4° C.) over residual activity of the parent alpha-amylase (ratio of activity in a themo-stressed sample over activity in a sample incubated at 4° C.), in particular the variants have an IF of at least 1.1, at least 1.2, at least 1.3, at least 1.4, at least 1.5, at least 1.6, at least 1.7, at least 1.8, at least 1.9, at least 2.0 compared to the alpha-amylase of SEQ ID NO: 3.

In another embodiment the present invention relates to alpha-amylase variants comprising at least substitutions corresponding to position 268 and 293 of SEQ ID NO: 1, in particular substitutions selected from the group consisting of:
268G+293Y; 268G+293F; 268G+293W; 268G+293H; 268G+293A; 268G+293Q; 268A+293Y; 268A+293F; 268A+293W; 268A+293H; 268A+293A; 268A+293Q; 268P+293Y; 268P+293F; 268P+293W; 268P+293H; 268P+293A; 268P+293Q; 268S+293Y; 268S+293F; 268S+293W; 268S+293H; 268S+293A; 268S+293Q; 268T+293Y; 268T+293F; 268T+293W; 268T+293H; 268T+293A; 268T+293Q; 268V+293Y; 268V+293F; 268V+293W; 268V+293H; 268V+293A; 268V+293Q; 268I+293Y; 268I+293F; 268I+293W; 268I+293H; 268I+293A; 268I+293Q; 268L+293Y; 268L+293F; 268L+293W; 268L+293H; 268L+293A; 268L+293Q; 268M+293Y; 268M+293F; 268M+293W; 268M+293H; 268M+293A; 268M+293Q, and wherein the variant has at least 60%, at least 65%, at least 70%, at least 75%, at least 80%, at least 85%, at least 90%, at least 95%, at least 96%, at least 97%, at least 98%, or at least 99%, but less than 100% sequence identity to SEQ ID NO: 4, and wherein the variants have increased thermo-stability determined as an improvement factor (IF) over the parent alpha-amylase, wherein the IF is determined as residual activity of the variant alpha-amylase (ratio of activity in a themo-stressed sample over activity in a sample incubated at 4° C.) over residual activity of the parent alpha-amylase (ratio of activity in a themo-stressed sample over activity in a sample incubated at 4° C.), in particular the variants have an IF of at least 1.1, at least 1.2, at least 1.3, at least 1.4, at least 1.5, at least 1.6, at least 1.7, at least 1.8, at least 1.9, at least 2.0 compared to the alpha-amylase of SEQ ID NO: 4.

In another embodiment the present invention relates to alpha-amylase variants comprising at least substitutions corresponding to position 268 and 293 of SEQ ID NO: 1, in particular substitutions selected from the group consisting of:
268G+293Y; 268G+293F; 268G+293W; 268G+293H; 268G+293A; 268G+293Q; 268A+293Y; 268A+293F; 268A+293W; 268A+293H; 268A+293A; 268A+293Q; 268P+293Y; 268P+293F; 268P+293W; 268P+293H; 268P+293A; 268P+293Q; 268S+293Y; 268S+293F; 268S+293W; 268S+293H; 268S+293A; 268S+293Q; 268T+293Y; 268T+293F; 268T+293W; 268T+293H; 268T+293A; 268T+293Q; 268V+293Y; 268V+293F; 268V+293W; 268V+293H; 268V+293A; 268V+293Q; 268I+293Y; 268I+293F; 268I+293W; 268I+293H; 268I+293A; 268I+293Q; 268L+293Y; 268L+293F; 268L+293W; 268L+293H; 268L+293A; 268L+293Q; 268M+293Y; 268M+293F; 268M+293W; 268M+293H; 268M+293A; 268M+293Q, and wherein the variant has at least 60%, at least 65%, at least 70%, at least 75%, at least 80%, at least 85%, at least 90%, at least 95%, at least 96%, at least 97%, at least 98%, or at least 99%, but less than 100% sequence identity to SEQ ID NO: 18, and wherein the variants have increased thermo-stability determined as an improvement factor (IF) over the parent alpha-amylase, wherein the IF is determined as residual activity of the variant alpha-amylase (ratio of activity in a themo-stressed sample over activity in a sample incubated at 4° C.) over residual activity of the parent alpha-amylase (ratio of activity in a themo-stressed sample over activity in a sample incubated at 4° C.), in particular the variants have an IF of at least 1.1, at least 1.2, at least 1.3, at least 1.4, at least 1.5, at least 1.6, at least 1.7, at least 1.8, at least 1.9, at least 2.0 compared to the alpha-amylase of SEQ ID NO: 18.

The variants of the invention may further have a deletion of two amino acids in the region corresponding to positions 179-182 using SEQ ID NO: 1 for numbering. More particularly the deletion may be selected from the group consisting of 179*+180*, 179*+181*, 179*+182*, 180*+181*, 180*+182*, and 181*+182*, particularly I181*+G182*.

In one embodiment, the alpha-amylase variants further comprise at least the substitutions corresponding to V59A+E129V+K177L+R179E+V212T+Q254S+M284V+Y268G+N293Y+T297N of SEQ ID NO: 1, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 1 or SEQ ID NO: 18, and wherein the variant has increased thermo-stability, particularly increased stability measured as residual alpha-amylase activity after heat-stress (or as HIF) compared to a parent alpha-amylase selected as SEQ ID NO: 1 having the substitutions corresponding to V59A+E129V+K177L+R179E+V212T+Q254S+M284V of SEQ ID NO: 1.

In one embodiment, the alpha-amylase variants comprise at least the substitutions corresponding to V59A+E129V+K177L+R179E+181*+182*+V212T+Q254S+M284V+Y268G+N293Y+T297N of SEQ ID NO: 1, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 1 or SEQ ID NO: 18, and wherein the variant has increased thermo-stability, particularly increased stability measured as residual alpha-amylase activity after heat-stress (or as HIF) compared to a parent alpha-amylase selected as SEQ ID NO: 1 having the substitutions corresponding to V59A+E129V+K177L+R179E+181*+182*+V212T+Q254S+M284V of SEQ ID NO: 1.

In one embodiment, the alpha-amylase variants comprise at least the substitutions corresponding to V59A+E129V+K177L+R179E+181*+182*+N193F+V212T+Q254S+M284V+Y268G+N293Y+T297N of SEQ ID NO: 1, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 1 or SEQ ID NO: 18, and wherein the variant has increased thermo-stability, particularly increased stability measured as residual alpha-amylase activity after heat-stress (or as HIF) compared to a parent alpha-amylase selected as SEQ ID NO: 1 having the substitutions corresponding to V59A+E129V+K177L+R179E+181*+182*+N193F+V212T+Q254S+M284V of SEQ ID NO: 1.

In one embodiment, the alpha-amylase variants comprise at least the substitutions corresponding to V59A+E129V+K177L+R179E+V212T+Q254S+M284V+Y268G+N293Y+T297N of SEQ ID NO: 1, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 2, and wherein the variant has increased thermo-stability, particularly increased stability measured as residual alpha-amylase activity after heat-stress (or as HIF) compared to a parent alpha-amylase selected as SEQ ID NO: 2 having the substitutions corresponding to V59A+E129V+K177L+R179E+V212T+Q254S+M284V of SEQ ID NO: 1.

In one embodiment, the alpha-amylase variants comprise at least the substitutions corresponding to V59A+E129V+K177L+R179E+181*+182*+V212T+Q254S+M284V+Y268G+N293Y+T297N of SEQ ID NO: 1, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 2, and wherein the variant has increased thermo-stability, particularly increased stability measured as residual alpha-amylase activity after heat-stress (or as HIF) compared to a parent alpha-amylase selected as SEQ ID NO: 2 having the substitutions corresponding to V59A+E129V+K177L+R179E+181*+182*+V212T+Q254S+M284V of SEQ ID NO: 1.

In one embodiment, the alpha-amylase variants comprise at least the substitutions corresponding to V59A+E129V+K177L+R179E+181*+182*+N193F+V212T+Q254S+M284V+Y268G+N293Y+T297N of SEQ ID NO: 1, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 2, and wherein the variant has increased thermo-stability, particularly increased stability measured as residual alpha-amylase activity after heat-stress (or as HIF) compared to a parent alpha-amylase selected as SEQ ID NO: 2 having the substitutions corresponding to V59A+E129V+K177L+R179E+181*+182*+N193F+V212T+Q254S+M284V of SEQ ID NO: 1.

In one embodiment, the alpha-amylase variants comprise at least the substitutions corresponding to V59A+E129V+K177L+R179E+V212T+Q254S+M284V+Y268G+N293Y+T297N of SEQ ID NO: 1, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3, and wherein the variant has increased thermo-stability, particularly increased stability measured as residual alpha-amylase activity after heat-stress (or as HIF) compared to a parent alpha-amylase selected as SEQ ID NO: 3 having the substitutions corresponding to V59A+E129V+K177L+R179E+V212T+Q254S+M284V of SEQ ID NO: 1.

In one embodiment, the alpha-amylase variants comprise at least the substitutions corresponding to V59A+E129V+K177L+R179E+181*+182*+V212T+Q254S+M284V+Y268G+N293Y+T297N of SEQ ID NO: 1, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3, and wherein the variant has increased thermo-stability, particularly increased stability measured as residual alpha-amylase activity after heat-stress (or as HIF) compared to a parent alpha-amylase selected as SEQ ID NO: 3 having the substitutions corresponding to V59A+E129V+K177L+R179E+181*+182*+V212T+Q254S+M284V of SEQ ID NO: 1.

In one embodiment, the alpha-amylase variants comprise at least the substitutions corresponding to V59A+E129V+K177L+R179E+181*+182*+N193F+V212T+Q254S+M284V+Y268G+N293Y+T297N of SEQ ID NO: 1, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3, and wherein the variant has increased thermo-stability, particularly increased stability measured as residual alpha-amylase activity after heat-stress (or as HIF) compared to a parent alpha-amylase selected as SEQ ID NO: 3 having the substitutions corresponding to V59A+E129V+K177L+R179E+181*+182*+N193F+V212T+Q254S+M284V of SEQ ID NO: 1.

In one embodiment, the alpha-amylase variants comprise at least the substitutions corresponding to V59A+E129V+K177L+R179E+181*+182*+E188P+T191N+V212T+Q254S+M284V+Y268G+N293Y+T297N of SEQ ID NO: 1, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 1, and wherein the variant has increased thermo-stability, particularly increased stability measured as residual alpha-amylase activity after heat-stress (or as HIF) compared to a parent alpha-amylase selected as SEQ ID NO: 1 having the substitutions corresponding to V59A+E129V+K177L+R179E+181*+182*+V212T+Q254S+M284V+Y268G+N293Y+T297N of SEQ ID NO: 1.

In one embodiment, the alpha-amylase variants comprise at least the substitutions corresponding to V59A+E129V+K177L+R179E+181*+182*+E188P+T191N+N193F+V212T+Q254S+M284V+Y268G+N293Y+T297N of SEQ ID NO: 1, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 1 or SEQ ID NO: 18, and wherein the variant has increased thermo-stability, particularly increased stability measured as residual alpha-amylase activity after heat-stress (or as HIF) compared to a parent alpha-amylase selected as SEQ ID NO: 1 having the substitutions corresponding to V59A+E129V+K177L+R179E+181*+182*+N193F+V212T+Q254S+M284V+Y268G+N293Y+T297N of SEQ ID NO: 1.

In one embodiment, the alpha-amylase variants comprise at least the substitutions corresponding to V59A+E129V+K177L+V212T+Q254S+M284V+Y268G+N293Y+T297N, and further a combination of substitutions selected from:
R179E+W115D+D117Q+T133P;
R179E+E188P+K279W;
R179S+A184Q+E188P+T191N+S242Y+K279I;
R179S+A184Q+E188P+T191N;
S173N+R179E+E188P+H208Y+S242Y+K279I;
and wherein the alpha-amylase variant has at least 70%, at least 75%, at least 80%, at least 85%, at least 90%, at least 95%, at least 96%, at least 97%, at least 98%, or at least 99% sequence identity to SEQ ID NO: 1 or SEQ ID NO: 18, and wherein the variant has increased thermo-stability, particularly increased stability measured as residual alpha-amylase activity after heat-stress (or as HIF) compared to a parent alpha-amylase, particularly a parent amylase selected from SEQ ID NO: 5.

In one embodiment, the alpha-amylase variants comprise at least the substitutions corresponding to V59A+E129V+K177L+V212T+Q254S+M284V+Y268G+N293Y+T297N, and optionally a deletion of two amino acids in the region corresponding to positions 179-182, particularly 181*+182*, and further a combination of substitutions selected from:
R179E+W115D+D117Q+T133P;
R179E+E188P+K279W;
R179S+A184Q+E188P+T191N+S242Y+K279I;
R179S+A184Q+E188P+T191N;
S173N+R179E+E188P+H208Y+S242Y+K279I;
and wherein the alpha-amylase variant has at least 70%, at least 75%, at least 80%, at least 85%, at least 90%, at least 95%, at least 96%, at least 97%, at least 98%, or at least 99% sequence identity to SEQ ID NO: 1 or SEQ ID NO: 18, and wherein the variant has increased thermo-stability, particularly increased stability measured as residual alpha-amylase activity after heat-stress (or as HIF) compared to a parent alpha-amylase, particularly a parent amylase selected from SEQ ID NO: 5.

In one embodiment, the alpha-amylase variants comprise at least the substitutions corresponding to V59A+E129V+K177L+N193F+V212T+Q254S+M284V+Y268G+N293Y+T297N, and optionally a deletion of two amino acids in the region corresponding to positions 179-182, particularly 181*+182*, and further a combination of substitutions selected from:
R179E+W115D+D117Q+T133P;
R179E+E188P+K279W;
R179S+A184Q+E188P+T191N+S242Y+K279I;
R179S+A184Q+E188P+T191N;
S173N+R179E+E188P+H208Y+S242Y+K279I;
and wherein the alpha-amylase variant has at least 70%, at least 75%, at least 80%, at least 85%, at least 90%, at least 95%, at least 96%, at least 97%, at least 98%, or at least 99% sequence identity to SEQ ID NO: 1 or SEQ ID NO: 18, and wherein the variant has increased thermo-stability, particularly increased stability measured as residual alpha-amylase activity after heat-stress (or as HIF) compared to a parent alpha-amylase, particularly a parent amylase selected from SEQ ID NO: 5.

In one embodiment, the alpha-amylase variants comprise at least the substitutions corresponding to V59A+E129V+K177L+V212T+Q254S+M284V+Y268G+N293Y+T297N, and further a combination of substitutions selected from:
R179E+W115D+D117Q+T133P;
R179E+E188P+K279W;
R179S+A184Q+E188P+T191N+S242Y+K279I;
R179S+A184Q+E188P+T191N;
S173N+R179E+E188P+H208Y+S242Y+K279I;
and wherein the alpha-amylase variant has at least 70%, at least 75%, at least 80%, at least 85%, at least 90%, at least 95%, at least 96%, at least 97%, at least 98%, or at least 99% sequence identity to SEQ ID NO: 1 or SEQ ID NO: 18, and wherein the variants have an improvement factor greater than 1.0, e.g., at least 1.05, at least 1.1, at least 1.2, at least 1.3, at least 1.4, at least 1.5, at least 1.6, and wherein the improvement factor is calculated as the ratio of retained activity (measured as ratio of DP3/DP4+ at 91° C. to DP3/DP4+ at 85° C.) for a given variant to the retained activity of the amylase of SEQ ID NO: 5.

In one embodiment, the alpha-amylase variants comprise at least the substitutions corresponding to V59A+E129V+K177L+V212T+Q254S+M284V+Y268G+N293Y+T297N, and optionally a deletion of two amino acids in the region corresponding to positions 179-182, particularly 181*+182*, and further a combination of substitutions selected from:
R179E+W115D+D117Q+T133P;
R179E+E188P+K279W;
R179S+A184Q+E188P+T191N+S242Y+K279I;
R179S+A184Q+E188P+T191N;
S173N+R179E+E188P+H208Y+S242Y+K279I;
and wherein the alpha-amylase variant has at least 70%, at least 75%, at least 80%, at least 85%, at least 90%, at least 95%, at least 96%, at least 97%, at least 98%, or at least 99% sequence identity to SEQ ID NO: 1 or SEQ ID NO: 18, and wherein the variants have an improvement factor greater than 1.0, e.g., at least 1.05, at least 1.1, at least 1.2, at least 1.3, at least 1.4, at least 1.5, at least 1.6, and wherein the improvement factor is calculated as the ratio of retained activity (measured as ratio of DP3/DP4+ at 91° C. to DP3/DP4+ at 85° C.) for a given variant to the retained activity of the amylase of SEQ ID NO: 5.

In one embodiment, the alpha-amylase variants comprise at least the substitutions corresponding to V59A+E129V+K177L+N193F+V212T+Q254S+M284V+Y268G+N293Y+T297N, and optionally a deletion of two amino acids in the region corresponding to positions 179-182, particularly 181*+182*, and further a combination of substitutions selected from:
R179E+W115D+D117Q+T133P;
R179E+E188P+K279W;
R179S+A184Q+E188P+T191N+S242Y+K279I;
R179S+A184Q+E188P+T191N;
S173N+R179E+E188P+H208Y+S242Y+K279I;
and wherein the alpha-amylase variant has at least 70%, at least 75%, at least 80%, at least 85%, at least 90%, at least 95%, at least 96%, at least 97%, at least 98%, or at least 99% sequence identity to SEQ ID NO: 1 or SEQ ID NO: 18, and wherein the variants have an improvement factor greater than 1.0, e.g., at least 1.05, at least 1.1, at least 1.2, at least 1.3, at least 1.4, at least 1.5, at least 1.6, and wherein the improvement factor is calculated as the ratio of retained activity (measured as ratio of DP3/DP4+ at 91° C. to DP3/DP4+ at 85° C.) for a given variant to the retained activity of the amylase of SEQ ID NO: 5.

In one embodiment, the alpha-amylase variants comprise at least the substitutions corresponding to N126Y+F153W+R178*+G179*+T180H+E187P+I203Y+N267G+Y292Y of SEQ ID NO: 6, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 6, and wherein the variant has increased thermo-stability, particularly increased stability measured as residual alpha-amylase activity after heat-stress (or as HIF) compared to a parent alpha-amylase selected as SEQ ID NO: 6 having the substitutions corresponding to N126Y+F153W+R178*+G179*+T180H+E187P+I203Y.

In one embodiment, the alpha-amylase variants comprise at least the substitutions corresponding to N126Y+F153W+R178*+G179*+T180H+E187P+I203Y+N267G+Y292Y+A296N of SEQ ID NO: 6, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 6, and wherein the variant has increased thermo-stability, particularly increased stability measured as residual alpha-amylase activity after heat-stress (or as HIF) compared to a parent alpha-amylase selected as SEQ ID NO: 6 having the substitutions corresponding to N126Y+F153W+R178*+G179*+T180H+E187P+I203Y.

In one embodiment, the alpha-amylase variants comprise at least the substitutions corresponding to N126Y+F153W+R178*+G179*+T180H+I203Y+S239Q+N267G+Y292Y of SEQ ID NO: 6, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 6, and wherein the variant has increased thermo-stability, particularly increased stability measured as residual alpha-amylase activity after heat-stress (or as HIF) compared to a parent alpha-amylase selected as SEQ ID NO: 6 having the substitutions corresponding to N126Y+F153W+R178*+G179*+T180H+I203Y+S239Q.

In one embodiment, the alpha-amylase variants comprise at least the substitutions corresponding to N126Y+F153W+R178*+G179*+T180H+I203Y+S239Q+N267G+Y292Y+A296N of SEQ ID NO: 6, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 6, and wherein the variant has increased thermo-stability, particularly increased stability measured as residual alpha-amylase activity after heat-stress (or as HIF) compared to a parent alpha-amylase selected as SEQ ID NO: 6 having the substitutions corresponding to N126Y+F153W+R178*+G179*+T180H+I203Y+S239Q.

In one embodiment, the alpha-amylase variants comprise at least the substitutions corresponding to V59A+E129V+K177L+R179E+V212T+Q254S+M284V+Y268G+N293Y+T297N of SEQ ID NO: 1 and optionally a deletion of two amino acids in the region corresponding to positions 179-182, particularly 181*+182*, and further the variant comprises one of the specific combinations of substitutions selected from:
H208Y+N217R;
E179S+A184Q+E188P+T191N;
I389K+R392K+D393L;
W115D+D117Q+T133P;
T24K+K25R+A27Q+E29D+N32H+Q86S+A90S+A93S;
Q86S+A90S+A93S;
D385E+I389K+R392K+D393N;
G416S+T417S+E418S+K419V;
T21Q+T24N+K25R;
T21Q+T24N+K25R+E29D;
T21Q+Q86K+D117Q+S173N+H208Y+S382H;
E179S+A184Q+E188P+T191N+S242Y; and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 1 or SEQ ID NO: 18, and wherein the variant has increased thermo-stability, particularly increased stability measured as residual alpha-amylase activity after heat-stress (or as HIF) compared to a parent alpha-amylase selected as SEQ ID NO: 1 having the substitutions corresponding to V59A+E129V+K177L+R179E+V212T+Q254S+M284V+Y268G+N293Y+T297N of SEQ ID NO: 1 and optionally a deletion of two amino acids in the region corresponding to positions 179-182, particularly 181*+182*.

In one embodiment, the alpha-amylase variants comprise at least the substitutions corresponding to V59A+E129V+K177L+R179E+N193F+V212T+Q254S+M284V+Y268G+N293Y+T297N of SEQ ID NO: 1 and optionally a deletion of two amino acids in the region corresponding to positions 179-182, particularly 181*+182*, and further the variant comprises one of the specific combinations of substitutions selected from:
H208Y+N217R;
E179S+A184Q+E188P+T191N;
I389K+R392K+D393L;
W115D+D117Q+T133P;
T24K+K25R+A27Q+E29D+N32H+Q86S+A90S+A93S;
Q86S+A90S+A93S;
D385E+I389K+R392K+D393N;
G416S+T417S+E418S+K419V;
T21Q+T24N+K25R;
T21Q+T24N+K25R+E29D;
T21Q+Q86K+D117Q+S173N+H208Y+S382H;
E179S+A184Q+E188P+T191N+S242Y; and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 1 or SEQ ID NO: 18, and wherein the variant has increased thermo-stability, particularly increased stability measured as residual alpha-amylase activity after heat-stress (or as HIF) compared to a parent alpha-amylase selected as SEQ ID NO: 1 having the substitutions corresponding to V59A+E129V+K177L+R179E+N193F+V212T+Q254S+M284V+Y268G+N293Y+T297N of SEQ ID NO: 1 and optionally a deletion of two amino acids in the region corresponding to positions 179-182, particularly 181*+182*.

In one embodiment, the alpha-amylase variants comprise at least the substitutions corresponding to V59A+E129V+

K177L+R179E+V212T+Q254S+M284V+Y268G+
N293Y+T297N of SEQ ID NO: 1 and optionally a deletion
of two amino acids in the region corresponding to positions
179-182, particularly 181*+182*, and further the variant
comprises one of the specific combinations of substitutions
selected from:
H208Y+N217R;
E179S+A184Q+E188P+T191N;
I389K+R392K+D393L;
W115D+D117Q+T133P;
T24K+K25R+A27Q+E29D+N32H+Q86S+A90S+A93S;
Q86S+A90S+A93S;
D385E+I389K+R392K+D393N;
G416S+T417S+E418S+K419V;
T21Q+T24N+K25R;
T21Q+T24N+K25R+E29D;
T21Q+Q86K+D117Q+S173N+H208Y+S382H;
E179S+A184Q+E188P+T191N+S242Y; and wherein the
variant has at least 60%, e.g., at least 65%, at least 70%, at
least 75%, at least 80%, at least 85%, at least 90%, at least
91%, at least 92%, at least 93%, at least 94%, at least 95%,
such as at least 96%, at least 97%, at least 98%, or at least
99%, but less than 100%, sequence identity to the polypeptide of SEQ ID NO: 2, and wherein the variant has increased
thermo-stability, particularly increased stability measured as
residual alpha-amylase activity after heat-stress (or as HIF)
compared to a parent alpha-amylase selected as SEQ ID NO:
2 having the substitutions corresponding to V59A+E129V+
K177L+R179E+V212T+Q254S+M284V+Y268G+
N293Y+T297N of SEQ ID NO: 1 and optionally a deletion
of two amino acids in the region corresponding to positions
179-182, particularly 181*+182*.

In one embodiment, the alpha-amylase variants comprise
at least the substitutions corresponding to V59A+E129V+
K177L+R179E+N193F+V212T+Q254S+M284V+Y268G+
N293Y+T297N of SEQ ID NO: 1 and optionally a deletion
of two amino acids in the region corresponding to positions
179-182, particularly 181*+182*, and further the variant
comprises one of the specific combinations of substitutions
selected from:
H208Y+N217R;
E179S+A184Q+E188P+T191N;
I389K+R392K+D393L;
W115D+D117Q+T133P;
T24K+K25R+A27Q+E29D+N32H+Q86S+A90S+A93S;
Q86S+A90S+A93S;
D385E+I389K+R392K+D393N;
G416S+T417S+E418S+K419V;
T21Q+T24N+K25R;
T21Q+T24N+K25R+E29D;
T21Q+Q86K+D117Q+S173N+H208Y+S382H;
E179S+A184Q+E188P+T191N+S242Y; and wherein the
variant has at least 60%, e.g., at least 65%, at least 70%, at
least 75%, at least 80%, at least 85%, at least 90%, at least
91%, at least 92%, at least 93%, at least 94%, at least 95%,
such as at least 96%, at least 97%, at least 98%, or at least
99%, but less than 100%, sequence identity to the polypeptide of SEQ ID NO: 2, and wherein the variant has increased
thermo-stability, particularly increased stability measured as
residual alpha-amylase activity after heat-stress (or as HIF)
compared to a parent alpha-amylase selected as SEQ ID NO:
2 having the substitutions corresponding to V59A+E129V+
K177L+R179E+N193F+V212T+Q254S+M284V+Y268G+
N293Y+T297N of SEQ ID NO: 1 and optionally a deletion
of two amino acids in the region corresponding to positions
179-182, particularly 181*+182*.

In one embodiment, the alpha-amylase variants comprise
at least the substitutions corresponding to V59A+E129V+
K177L+R179E+V212T+Q254S+M284V+Y268G+
N293Y+T297N of SEQ ID NO: 1 and optionally a deletion
of two amino acids in the region corresponding to positions
179-182, particularly 181*+182*, and further the variant
comprises one of the specific combinations of substitutions
selected from:
H208Y+N217R;
E179S+A184Q+E188P+T191N;
I389K+R392K+D393L;
W115D+D117Q+T133P;
T24K+K25R+A27Q+E29D+N32H+Q86S+A90S+A93S;
Q86S+A90S+A93S;
D385E+I389K+R392K+D393N;
G416S+T417S+E418S+K419V;
T21Q+T24N+K25R;
T21Q+T24N+K25R+E29D;
T21Q+Q86K+D117Q+S173N+H208Y+S382H;
E179S+A184Q+E188P+T191N+S242Y; and wherein the
variant has at least 60%, e.g., at least 65%, at least 70%, at
least 75%, at least 80%, at least 85%, at least 90%, at least
91%, at least 92%, at least 93%, at least 94%, at least 95%,
such as at least 96%, at least 97%, at least 98%, or at least
99%, but less than 100%, sequence identity to the polypeptide of SEQ ID NO: 3, and wherein the variant has increased
thermo-stability, particularly increased stability measured as
residual alpha-amylase activity after heat-stress (or as HIF)
compared to a parent alpha-amylase selected as SEQ ID NO:
3 having the substitutions corresponding to V59A+E129V+
K177L+R179E+V212T+Q254S+M284V+Y268G+
N293Y+T297N of SEQ ID NO: 1 and optionally a deletion
of two amino acids in the region corresponding to positions
179-182, particularly 181*+182*.

In one embodiment, the alpha-amylase variants comprise
at least the substitutions corresponding to V59A+E129V+
K177L+R179E+N193F+V212T+Q254S+M284V+Y268G+
N293Y+T297N of SEQ ID NO: 1 and optionally a deletion
of two amino acids in the region corresponding to positions
179-182, particularly 181*+182*, and further the variant
comprises one of the specific combinations of substitutions
selected from:
H208Y+N217R;
E179S+A184Q+E188P+T191N;
I389K+R392K+D393L;
W115D+D117Q+T133P;
T24K+K25R+A27Q+E29D+N32H+Q86S+A90S+A93S;
Q86S+A90S+A93S;
D385E+I389K+R392K+D393N;
G416S+T417S+E418S+K419V;
T21Q+T24N+K25R;
T21Q+T24N+K25R+E29D;
T21Q+Q86K+D117Q+S173N+H208Y+S382H;
E179S+A184Q+E188P+T191N+S242Y; and wherein the
variant has at least 60%, e.g., at least 65%, at least 70%, at
least 75%, at least 80%, at least 85%, at least 90%, at least
91%, at least 92%, at least 93%, at least 94%, at least 95%,
such as at least 96%, at least 97%, at least 98%, or at least
99%, but less than 100%, sequence identity to the polypeptide of SEQ ID NO: 3, and wherein the variant has increased
thermo-stability, particularly increased stability measured as
residual alpha-amylase activity after heat-stress (or as HIF)
compared to a parent alpha-amylase selected as SEQ ID NO:
3 having the substitutions corresponding to V59A+E129V+
K177L+R179E+N193F+V212T+Q254S+M284V+Y268G+
N293Y+T297N of SEQ ID NO: 1 and optionally a deletion of two amino acids in the region corresponding to positions 179-182, particularly 181*+182*.

In one embodiment, the alpha-amylase variants comprise at least the substitutions corresponding to V59A+E129V+K177L+R179E+V212T+Q254S+M284V+Y268G+N293Y+T297N of SEQ ID NO: 1 and optionally a deletion of two amino acids in the region corresponding to positions 179-182, particularly 181*+182*, and further the variant comprises one of the specific combinations of substitutions or deletions selected from:
G112A;
T309W;
T312W;
T309W+T312W;
E179G;
T212I;
S173N;
K141H;
T50I;
G108A;
T398R;
P320A;
T225N;
S382H;
I277L+G282H;
L36Q;
A91I;
P258E;
T21Q;
T133P+E179G;
A304N;
S406W;
A2*+P3*;
D328E+E333Q;
E210D;
L16T+T21K+L22Q+T24D;
N127Y+E188P;
and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 1 SEQ ID NO: 18, and wherein the variant has increased thermo-stability, particularly increased stability measured as residual alpha-amylase activity after heat-stress (or as HIF) compared to a parent alpha-amylase selected as SEQ ID NO: 1 having the substitutions corresponding to V59A+E129V+K177L+R179E+V212T+Q254S+M284V+Y268G+N293Y+T297N of SEQ ID NO: 1 and optionally a deletion of two amino acids in the region corresponding to positions 179-182, particularly 181*+182*.

In one embodiment, the alpha-amylase variants comprise at least the substitutions corresponding to V59A+E129V+K177L+R179E+N193F+V212T+Q254S+M284V+Y268G+N293Y+T297N of SEQ ID NO: 1 and optionally a deletion of two amino acids in the region corresponding to positions 179-182, particularly 181*+182*, and further the variant comprises one of the specific combinations of substitutions or deletions selected from:
G112A;
T309W;
T312W;
T309W+T312W;
E179G;
T212I;
S173N;
K141H;
T50I;
G108A;
T398R;
P320A;
T225N;
S382H;
I277L+G282H;
L36Q;
A91I;
P258E;
T21Q;
T133P+E179G;
A304N;
S406W;
A2*+P3*;
D328E+E333Q;
E210D;
L16T+T21K+L22Q+T24D;
N127Y+E188P;
and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 1 or SEQ ID NO: 18, and wherein the variant has increased thermo-stability, particularly increased stability measured as residual alpha-amylase activity after heat-stress (or as HIF) compared to a parent alpha-amylase selected as SEQ ID NO: 1 having the substitutions corresponding to V59A+E129V+K177L+R179E+N193F+V212T+Q254S+M284V+Y268G+N293Y+T297N of SEQ ID NO: 1 and optionally a deletion of two amino acids in the region corresponding to positions 179-182, particularly 181*+182*.

In one embodiment, the alpha-amylase variants comprise at least the substitutions corresponding to V59A+E129V+K177L+R179E+V212T+Q254S+M284V+Y268G+N293Y+T297N of SEQ ID NO: 1 and optionally a deletion of two amino acids in the region corresponding to positions 179-182, particularly 181*+182*, and further the variant comprises one of the specific combinations of substitutions or deletions selected from:
G112A;
T309W;
T312W;
T309W+T312W;
E179G;
T212I;
S173N;
K141H;
T50I;
G108A;
T398R;
P320A;
T225N;
S382H;
I277L+G282H;
L36Q;
A91I;
P258E;
T21Q;
T133P+E179G;
A304N;
S406W;
A2*+P3*;
D328E+E333Q;

E210D;
L16T+T21K+L22Q+T24D;
N127Y+E188P;
and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 2, and wherein the variant has increased thermo-stability, particularly increased stability measured as residual alpha-amylase activity after heat-stress (or as HIF) compared to a parent alpha-amylase selected as SEQ ID NO: 2 having the substitutions corresponding to V59A+E129V+K177L+R179E+V212T+Q254S+M284V+Y268G+N293Y+T297N of SEQ ID NO: 1 and optionally a deletion of two amino acids in the region corresponding to positions 179-182, particularly 181*+182*.

In one embodiment, the alpha-amylase variants comprise at least the substitutions corresponding to V59A+E129V+K177L+R179E+N193F+V212T+Q254S+M284V+Y268G+N293Y+T297N of SEQ ID NO: 1 and optionally a deletion of two amino acids in the region corresponding to positions 179-182, particularly 181*+182*, and further the variant comprises one of the specific combinations of substitutions or deletions selected from:
G112A;
T309W;
T312W;
T309W+T312W;
E179G;
T212I;
S173N;
K141H;
T50I;
G108A;
T398R;
P320A;
T225N;
S382H;
I277L+G282H;
L36Q;
A91I;
P258E;
T21Q;
T133P+E179G;
A304N;
S406W;
A2*+P3*;
D328E+E333Q;
E210D;
L16T+T21K+L22Q+T24D;
N127Y+E188P;
and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 2, and wherein the variant has increased thermo-stability, particularly increased stability measured as residual alpha-amylase activity after heat-stress (or as HIF) compared to a parent alpha-amylase selected as SEQ ID NO: 2 having the substitutions corresponding to V59A+E129V+K177L+R179E+N193F+V212T+Q254S+M284V+Y268G+N293Y+T297N of SEQ ID NO: 1 and optionally a deletion of two amino acids in the region corresponding to positions 179-182, particularly 181*+182*.

In one embodiment, the alpha-amylase variants comprise at least the substitutions corresponding to V59A+E129V+K177L+R179E+V212T+Q254S+M284V+Y268G+N293Y+T297N of SEQ ID NO: 1 and optionally a deletion of two amino acids in the region corresponding to positions 179-182, particularly 181*+182*, and further the variant comprises one of the specific combinations of substitutions or deletions selected from:
G112A;
T309W;
T312W;
T309W+T312W;
E179G;
T212I;
S173N;
K141H;
T50I;
G108A;
T398R;
P320A;
T225N;
S382H;
I277L+G282H;
L36Q;
A91I;
P258E;
T21Q;
T133P+E179G;
A304N;
S406W;
A2*+P3*;
D328E+E333Q;
E210D;
L16T+T21K+L22Q+T24D;
N127Y+E188P;
and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3, and wherein the variant has increased thermo-stability, particularly increased stability measured as residual alpha-amylase activity after heat-stress (or as HIF) compared to a parent alpha-amylase selected as SEQ ID NO: 3 having the substitutions corresponding to V59A+E129V+K177L+R179E+V212T+Q254S+M284V+Y268G+N293Y+T297N of SEQ ID NO: 1 and optionally a deletion of two amino acids in the region corresponding to positions 179-182, particularly 181*+182*.

In one embodiment, the alpha-amylase variants comprise at least the substitutions corresponding to V59A+E129V+K177L+R179E+N193F+V212T+Q254S+M284V+Y268G+N293Y+T297N of SEQ ID NO: 1 and optionally a deletion of two amino acids in the region corresponding to positions 179-182, particularly 181*+182*, and further the variant comprises one of the specific combinations of substitutions or deletions selected from:
G112A;
T309W;
T312W;
T309W+T312W;
E179G;
T212I;
S173N;
K141H;
T50I;
G108A;

T398R;
P320A;
T225N;
S382H;
I277L+G282H;
L36Q;
A91I;
P258E;
T21Q;
T133P+E179G;
A304N;
S406W;
A2*+P3*;
D328E+E333Q;
E210D;
L16T+T21K+L22Q+T24D;
N127Y+E188P;
and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3, and wherein the variant has increased thermo-stability, particularly increased stability measured as residual alpha-amylase activity after heat-stress (or as HIF) compared to a parent alpha-amylase selected as SEQ ID NO: 3 having the substitutions corresponding to V59A+E129V+K177L+R179E+N193F+V212T+Q254S+M284V+Y268G+N293Y+T297N of SEQ ID NO: 1 and optionally a deletion of two amino acids in the region corresponding to positions 179-182, particularly 181*+182*.

In one embodiment, the alpha-amylase variants comprise at least the substitutions corresponding to V59A+E129V+K177L+R179E+V212T+Q254S+M284V+Y268G+N293Y+T297N of SEQ ID NO: 1 and optionally a deletion of two amino acids in the region corresponding to positions 179-182, particularly 181*+182*, and further the variant comprises one of the specific combinations of substitutions or deletions selected from:
W115D+D117Q+T133P;
E188P;
E188P+N275F;
E188P+N275H;
E188P+K279F;
E188P+K279Y;
E188P+K279W;
E188P+K279H;
E179S+A184Q+E188P+T191N;
E188P+S242Y+I479V;
E188P+S242Y+F403L;
E188P+S242Y+K279Y;
G180*+I181*+E188P+N193F+S242Y;
E188P+S242Y;
T21Q+Q86K+D117Q+S173N+E188P+H208Y+S242Y+S382H;
S173N+E188P+S242Y;
E188P+K279I;
E179S+A184Q+E188P+T191N+S242Y+K279W;
E179S+A184Q+E188P+T191N+S242Y+K279I;
E188P+S242Y+K279I;
E188P+N193F+S242Y;
T21Q+T24N+K25R+E29D+E188P+S242Y;
E188P+S242Y+K279F;
E188P+S242Y+K279W+F449L;
E188P+S242Y+K279H;

and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 1 or SEQ ID NO: 18, and wherein the variant has increased thermo-stability, particularly increased stability measured as residual alpha-amylase activity after heat-stress (or as HIF) compared to a parent alpha-amylase selected as SEQ ID NO: 1 having the substitutions corresponding to V59A+E129V+K177L+R179E+V212T+Q254S+M284V+Y268G+N293Y+T297N of SEQ ID NO: 1 and optionally a deletion of two amino acids in the region corresponding to positions 179-182, particularly 181*+182*.

In one embodiment, the alpha-amylase variants comprise at least the substitutions corresponding to V59A+E129V+K177L+R179E+N193F+V212T+Q254S+M284V+Y268G+N293Y+T297N of SEQ ID NO: 1 and optionally a deletion of two amino acids in the region corresponding to positions 179-182, particularly 181*+182*, and further the variant comprises one of the specific combinations of substitutions or deletions selected from:
W115D+D117Q+T133P;
E188P;
E188P+N275F;
E188P+N275H;
E188P+K279F;
E188P+K279Y;
E188P+K279W;
E188P+K279H;
E179S+A184Q+E188P+T191N;
E188P+S242Y+I479V;
E188P+S242Y+F403L;
E188P+S242Y+K279Y;
G180*+I181*+E188P+N193F+S242Y;
E188P+S242Y;
T21Q+Q86K+D117Q+S173N+E188P+H208Y+S242Y+S382H;
S173N+E188P+S242Y;
E188P+K279I;
E179S+A184Q+E188P+T191N+S242Y+K279W;
E179S+A184Q+E188P+T191N+S242Y+K279I;
E188P+S242Y+K279I;
E188P+N193F+S242Y;
T21Q+T24N+K25R+E29D+E188P+S242Y;
E188P+S242Y+K279F;
E188P+S242Y+K279W+F449L;
E188P+S242Y+K279H; and
wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 1 or SEQ ID NO: 18, and wherein the variant has increased thermo-stability, particularly increased stability measured as residual alpha-amylase activity after heat-stress (or as HIF) compared to a parent alpha-amylase selected as SEQ ID NO: 1 having the substitutions corresponding to V59A+E129V+K177L+R179E+N193F+V212T+Q254S+M284V+Y268G+N293Y+T297N of SEQ ID NO: 1 and optionally a deletion of two amino acids in the region corresponding to positions 179-182, particularly 181*+182*.

In one embodiment, the alpha-amylase variants comprise at least the substitutions corresponding to V59A+E129V+K177L+R179E+V212T+Q254S+M284V+Y268G+

N293Y+T297N of SEQ ID NO: 1 and optionally a deletion of two amino acids in the region corresponding to positions 179-182, particularly 181*+182*, and further the variant comprises one of the specific combinations of substitutions or deletions selected from:
W115D+D117Q+T133P;
E188P;
E188P+N275F;
E188P+N275H;
E188P+K279F;
E188P+K279Y;
E188P+K279W;
E188P+K279H;
E179S+A184Q+E188P+T191N;
E188P+S242Y+I479V;
E188P+S242Y+F403L;
E188P+S242Y+K279Y;
G180*+I181*+E188P+N193F+S242Y;
E188P+S242Y;
T21Q+Q86K+D117Q+S173N+E188P+H208Y+S242Y+S382H;
S173N+E188P+S242Y;
E188P+K279I;
E179S+A184Q+E188P+T191N+S242Y+K279W;
E179S+A184Q+E188P+T191N+S242Y+K279I;
E188P+S242Y+K279I;
E188P+N193F+S242Y;
T21Q+T24N+K25R+E29D+E188P+S242Y;
E188P+S242Y+K279F;
E188P+S242Y+K279W+F449L;
E188P+S242Y+K279H; and
wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 2, and wherein the variant has increased thermo-stability, particularly increased stability measured as residual alpha-amylase activity after heat-stress (or as HIF) compared to a parent alpha-amylase selected as SEQ ID NO: 2 having the substitutions corresponding to V59A+E129V+K177L+R179E+V212T+Q254S+M284V+Y268G+N293Y+T297N of SEQ ID NO: 1 and optionally a deletion of two amino acids in the region corresponding to positions 179-182, particularly 181*+182*.

In one embodiment, the alpha-amylase variants comprise at least the substitutions corresponding to V59A+E129V+K177L+R179E+N193F+V212T+Q254S+M284V+Y268G+N293Y+T297N of SEQ ID NO: 1 and optionally a deletion of two amino acids in the region corresponding to positions 179-182, particularly 181*+182*, and further the variant comprises one of the specific combinations of substitutions or deletions selected from:
W115D+D117Q+T133P;
E188P;
E188P+N275F;
E188P+N275H;
E188P+K279F;
E188P+K279Y;
E188P+K279W;
E188P+K279H;
E179S+A184Q+E188P+T191N;
E188P+S242Y+I479V;
E188P+S242Y+F403L;
E188P+S242Y+K279Y;
G180*+I181*+E188P+N193F+S242Y;
E188P+S242Y;
T21Q+Q86K+D117Q+S173N+E188P+H208Y+S242Y+S382H;
S173N+E188P+S242Y;
E188P+K279I;
E179S+A184Q+E188P+T191N+S242Y+K279W;
E179S+A184Q+E188P+T191N+S242Y+K279I;
E188P+S242Y+K279I;
E188P+N193F+S242Y;
T21Q+T24N+K25R+E29D+E188P+S242Y;
E188P+S242Y+K279F;
E188P+S242Y+K279W+F449L;
E188P+S242Y+K279H; and
wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 2, and wherein the variant has increased thermo-stability, particularly increased stability measured as residual alpha-amylase activity after heat-stress (or as HIF) compared to a parent alpha-amylase selected as SEQ ID NO: 2 having the substitutions corresponding to V59A+E129V+K177L+R179E+N193F+V212T+Q254S+M284V+Y268G+N293Y+T297N of SEQ ID NO: 1 and optionally a deletion of two amino acids in the region corresponding to positions 179-182, particularly 181*+182*.

In one embodiment, the alpha-amylase variants comprise at least the substitutions corresponding to V59A+E129V+K177L+R179E+V212T+Q254S+M284V+Y268G+N293Y+T297N of SEQ ID NO: 1 and optionally a deletion of two amino acids in the region corresponding to positions 179-182, particularly 181*+182*, and further the variant comprises one of the specific combinations of substitutions or deletions selected from:
W115D+D117Q+T133P;
E188P;
E188P+N275F;
E188P+N275H;
E188P+K279F;
E188P+K279Y;
E188P+K279W;
E188P+K279H;
E179S+A184Q+E188P+T191N;
E188P+S242Y+I479V;
E188P+S242Y+F403L;
E188P+S242Y+K279Y;
G180*+I181*+E188P+N193F+S242Y;
E188P+S242Y;
T21Q+Q86K+D117Q+S173N+E188P+H208Y+S242Y+S382H;
S173N+E188P+S242Y;
E188P+K279I;
E179S+A184Q+E188P+T191N+S242Y+K279W;
E179S+A184Q+E188P+T191N+S242Y+K279I;
E188P+S242Y+K279I;
E188P+N193F+S242Y;
T21Q+T24N+K25R+E29D+E188P+S242Y;
E188P+S242Y+K279F;
E188P+S242Y+K279W+F449L;
E188P+S242Y+K279H; and
wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3, and wherein the variant has increased thermo-stability, particularly increased stability measured as residual alpha-amylase activity after heat-stress (or as HIF) compared to a parent alpha-amylase selected as SEQ ID NO: 3 having the substitutions corresponding to V59A+E129V+K177L+R179E+V212T+Q254S+M284V+ Y268G+N293Y+T297N of SEQ ID NO: 1 and optionally a deletion of two amino acids in the region corresponding to positions 179-182, particularly 181*+182*.

In one embodiment, the alpha-amylase variants comprise at least the substitutions corresponding to V59A+E129V+ K177L+R179E+N193F+V212T+Q254S+M284V+Y268G+ N293Y+T297N of SEQ ID NO: 1 and optionally a deletion of two amino acids in the region corresponding to positions 179-182, particularly 181*+182*, and further the variant comprises one of the specific combinations of substitutions or deletions selected from:
W115D+D117Q+T133P;
E188P;
E188P+N275F;
E188P+N275H;
E188P+K279F;
E188P+K279Y;
E188P+K279W;
E188P+K279H;
E179S+A184Q+E188P+T191N;
E188P+S242Y+I479V;
E188P+S242Y+F403L;
E188P+S242Y+K279Y;
G180*+I181*+E188P+N193F+5242Y;
E188P+5242Y;
T21Q+Q86K+D117Q+S173N+E188P+H208Y+S242Y+ S382H;
S173N+E188P+5242Y;
E188P+K279I;
E179S+A184Q+E188P+T191N+S242Y+K279W;
E179S+A184Q+E188P+T191N+S242Y+K279I;
E188P+S242Y+K279I;
E188P+N193F+5242Y;
T21Q+T24N+K25R+E29D+E188P+5242Y;
E188P+S242Y+K279F;
E188P+S242Y+K279W+F449L;
E188P+S242Y+K279H; and
wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3, and wherein the variant has increased thermo-stability, particularly increased stability measured as residual alpha-amylase activity after heat-stress (or as HIF) compared to a parent alpha-amylase selected as SEQ ID NO: 3 having the substitutions corresponding to V59A+E129V+K177L+R179E+N193F+V212T+Q254S+ M284V+Y268G+N293Y+T297N of SEQ ID NO: 1 and optionally a deletion of two amino acids in the region corresponding to positions 179-182, particularly 181*+ 182*.

In one aspect, the number of alterations in the variants of the present invention is 1-20, e.g., 1-10 and 1-5, such as 1, 2, 3, 4, 5, 6, 7, 8, 9 or 10 alterations.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for alpha-amylase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

The variants may consist of C-terminally truncated versions, e.g., the variant is truncated, preferably to have a length of around 490 amino acids, such as from 482-493 amino acids.

In another embodiment the variant alpha-amylase is truncated, preferably after position 484 of SEQ ID NO: 1, particularly after position 485, particularly after position 486, particularly after position 487, particularly after position 488, particularly after position 489, particularly after position 490, particularly after position 491, particularly after position 492, more particularly after position 493.

In an embodiment, the variants have increased thermo-stability, particularly increased stability measured as residual alpha-amylase activity determined by EnzCheck assay after 15 min or 30 min incubation at 90° C., pH 4.5, 5 ppm $Ca^{2+}$ compared to a parent alpha-amylase, particularly a parent amylase selected from the group consisting of SEQ ID NO: 1, SEQ ID NO: 2, SEQ ID NO: 3, SEQ ID NO: 4, and SEQ ID NO: 5.

Preparation of Variants

The present invention also relates to a method for obtaining a variant having alpha-amylase activity, comprising introducing substitutions at positions corresponding to position 268 and 293 of SEQ ID NO: 1, in particular substitutions selected from the group consisting of: 268G+293Y; 268G+293F; 268G+293W; 268G+293H; 268G+293A; 268G+293Q; 268A+293Y; 268A+293F; 268A+293W; 268A+293H; 268A+293A; 268A+293Q; 268P+293Y;

268P+293F; 268P+293W; 268P+293H; 268P+293A; 268P+293Q; 268S+293Y; 268S+293F; 268S+293W; 268S+293H; 268S+293A; 268S+293Q; 268T+293Y; 268T+293F; 268T+293W; 268T+293H; 268T+293A; 268T+293Q; 268V+293Y; 268V+293F; 268V+293W; 268V+293H; 268V+293A; 268V+293Q; 268I+293Y; 268I+293F; 268I+293W; 268I+293H; 268I+293A; 268I+293Q; 268L+293Y; 268L+293F; 268L+293W; 268L+293H; 268L+293A; 268L+293Q; 268M+293Y; 268M+293F; 268M+293W; 268M+293H; 268M+293A; 268M+293Q, and wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of SEQ ID NO: 1, SEQ ID NO: 2, SEQ ID NO: 3, and SEQ ID NO: 4, and seq ID NO: 18; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences. The control sequence(s) may be foreign/heterologous to the polynucleotide encoding a variant of the present invention.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, Journal of Bacteriology 177: 3465-3471).

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT).

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. In one embodiment the one or more control sequences are heterologous to the polynucleotide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*. The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell, e.g. a yeast cell, such as a *Saccharomyces cerevisiae* cell.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Compositions

The present invention also relates to compositions comprising a variant alpha-amylase of the present invention.

The compositions may comprise a variant alpha-amylase of the present invention as the major enzymatic component, e.g., a mono-component composition. Alternatively, the compositions may comprise multiple enzymatic activities, such as one or more (e.g., several) enzymes selected from the group consisting of protease, glucoamylase, beta-amylase, pullulanase.

In one embodiment the composition comprises a variant alpha-amylase of the invention and a second alpha-amylase derived form *Bacillus licheniformis*, particularly a second alpha-amylase having at least 70%, at least 75%, at least 80%, at least 85%, at least 90%, at least 95%, at least 96%, at least 97%, at least 98%, or at least 99% sequence identity to SEQ ID NO: 17.

In one embodiment the composition comprises a variant alpha-amylase of the invention and a second alpha-amylase derived form *Cytophaga* sp., particularly a second alpha-amylase having at least 70%, at least 75%, at least 80%, at least 85%, at least 90%, at least 95%, at least 96%, at least 97%, at least 98%, or at least 99% sequence identity to SEQ ID NO: 6.

In another embodiment the composition comprises a variant alpha-amylase of the invention and a second alpha-amylase having at least 70%, at least 75%, at least 80%, at least 85%, at least 90%, at least 95%, at least 96%, at least 97%, at least 98%, or at least 99% sequence identity to SEQ ID NO: 15 or 16, wherein the second alpha-amylase comprises the substitutions: G48A+T49I+H68W+G107A+H156Y+A181T+E185P+N190F+A209V+Q264S+K176L+F201Y+H205Y+K213T+E255P+Q360S+D416V+R437W using SEQ ID NO: 17 for numbering.

In a further embodiment the composition comprises an alpha-amylase of the invention having at least 70%, at least 75%, at least 80%, at least 85%, at least 90%, at least 95%, at least 96%, at least 97%, at least 98%, or at least 99% sequence identity to SEQ ID NO: 1 and wherein the alpha-amylase comprises the substitutions V59A+E129V+K177L+V212T+Q254S+M284V+Y268G+N293Y+T297N, and optionally a deletion of two amino acids in the region corresponding to positions 179-182, particularly 181*+182*, and further a combination of substitutions selected from:

R179E+W115D+D117Q+T133P;
R179E+E188P+K279W;
R179S+A184Q+E188P+T191N+S242Y+K279I;
R179S+A184Q+E188P+T191N;
S173N+R179E+E188P+H208Y+S242Y+K279I;
and a second alpha-amylase having at least 70%, at least 75%, at least 80%, at least 85%, at least 90%, at least 95%, at least 96%, at least 97%, at least 98%, or at least 99% sequence identity to SEQ ID NO: 15 or 16, wherein the second alpha-amylase comprises the substitutions: G48A+ T49I+H68W+G107A+H156Y+A181T+E185P+N190F+ A209V+Q264S+K176L+F201Y+H205Y+K213T+E255P+ Q360S+D416V+R437W using SEQ ID NO: 17 for numbering.

In a further embodiment the composition comprises an alpha-amylase of the invention having at least 70%, at least 75%, at least 80%, at least 85%, at least 90%, at least 95%, at least 96%, at least 97%, at least 98%, or at least 99% sequence identity to SEQ ID NO: 1 and wherein the alpha-amylase comprises the substitutions V59A+E129V+ K177L+N193F+V212T+Q254S+M284V+Y268G+ N293Y+T297N, and optionally a deletion of two amino acids in the region corresponding to positions 179-182, particularly 181*+182*, and further a combination of substitutions selected from:
R179E+W115D+D117Q+T133P;
R179E+E188P+K279W;
R179S+A184Q+E188P+T191N+S242Y+K279I;
R179S+A184Q+E188P+T191N;
S173N+R179E+E188P+H208Y+S242Y+K279I,
and a second alpha-amylase having at least 70%, at least 75%, at least 80%, at least 85%, at least 90%, at least 95%, at least 96%, at least 97%, at least 98%, or at least 99% sequence identity to SEQ ID NO: 15 or 16, wherein the second alpha-amylase comprises the substitutions: G48A+ T49I+H68W+G107A+H156Y+A181T+E185P+N190F+ A209V+Q264S+K176L+F201Y+H205Y+K213T+E255P+ Q360S+D416V+R437W using SEQ ID NO: 17 for numbering.

In a particular embodiment the composition comprises a variant alpha-amylase of the present invention and a protease, particularly a protease from *Pyrococcus* sp., or *Thermococcus* sp., or a protease from *Thermoascus aurantiacus*.

In one embodiment the protease is selected from a S8 protease from *Pyrococcus furiosus* shown in SEQ ID NO: 7 or a protease having at least 85%, at least 90%, at least 95%, at least 96%, at least 97%, at least 98%, or at least 99%, or 100% sequence identity to the polypeptide of SEQ ID NO: 7.

In another embodiment the protease is selected from a variant *Thermoascus aurantiacus* protease, wherein the variant protease comprises one of the following combinations of mutations:
D79L+S87P+A112P+D142L;
D79L+S87P+D142L; or
A27K+D79L+Y82F+S87G+D104P+A112P+A126V+ D142L; and the protease variant has at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 8.

The compositions may be prepared in accordance with methods known in the art and may be in the form of a liquid or a dry composition. The compositions may be stabilized in accordance with methods known in the art.

Methods of Using the Variant Alpha-Amylase of the Invention—Industrial Applications The variant alpha-amylases of the present invention possess valuable properties allowing for a variety of industrial applications. In particular, the alpha-amylases may be used in ethanol production, and starch conversion processes.

Further, the alpha-amylases of the invention are particularly useful in the production of sweeteners/syrups and ethanol (see, e.g., U.S. Pat. No. 5,231,017, which is hereby incorporated by reference), such as fuel, drinking and industrial ethanol, from starch or whole grains.

In one embodiment the present invention relates to a use of the alpha-amylase according to the invention in a liquefaction process. The produced liquefact may be further processed into a syrup and/or a fermentation product.

Starch Processing

Native starch consists of microscopic granules, which are insoluble in water at room temperature. When aqueous starch slurry is heated, the granules swell and eventually burst, dispersing the starch molecules into the solution. At temperatures up to about 50° C. to 75° C. the swelling may be reversible. However, with higher temperatures an irreversible swelling called "gelatinization" begins. During this "gelatinization" process there is a dramatic increase in viscosity. Granular starch to be processed may be a highly refined starch quality, preferably at least 90%, at least 95%, at least 97% or at least 99.5% pure or it may be a more crude starch-containing materials comprising (e.g., milled) whole grains including non-starch fractions such as germ residues and fibers. The raw material, such as whole grains, may be reduced in particle size, e.g., by milling, in order to open up the structure and allowing for further processing. In dry milling whole kernels are milled and used. Wet milling gives a good separation of germ and meal (starch granules and protein) and is often applied at locations where the starch hydrolyzate is used in the production of, e.g., syrups. Both dry and wet milling is well known in the art of starch processing and may be used in a process of the invention. Methods for reducing the particle size of the starch containing material are well known to those skilled in the art.

As the solids level is 30-40% in a typical industrial process, the starch has to be thinned or "liquefied" so that it can be suitably processed. This reduction in viscosity is primarily attained by enzymatic degradation in current commercial practice.

Liquefaction is carried out in the presence of an alpha-amylase, preferably a bacterial alpha-amylase and/or acid fungal alpha-amylase. In an embodiment, a phytase is also present during liquefaction. In an embodiment, viscosity reducing enzymes such as a xylanase and/or beta-glucanase is also present during liquefaction.

During liquefaction, the long-chained starch is degraded into branched and linear shorter units (maltodextrins) by an alpha-amylase. Liquefaction may be carried out as a three-step hot slurry process. The slurry is heated to between 60-95° C. (e.g., 70-90° C., such as 77-86° C., 80-85° C., 83-85° C.) and an alpha-amylase is added to initiate liquefaction (thinning).

The slurry may in an embodiment be jet-cooked at between 95-140° C., e.g., 105-125° C., for about 1-15 minutes, e.g., about 3-10 minutes, especially around 5 minutes. The slurry is then cooled to 60-95° C. and more alpha-amylase is added to obtain final hydrolysis (secondary liquefaction). The jet-cooking process is carried out at pH 4.5-6.5, typically at a pH between 5 and 6. The alpha-amylase may be added as a single dose, e.g., before jet cooking.

The liquefaction process is carried out at between 70-95° C., such as 80-90° C., such as around 85° C., for about 10 minutes to 5 hours, typically for 1-2 hours. The pH is between 4 and 7, such as between 5.5 and 6.2. In order to ensure optimal enzyme stability under these conditions, calcium may optionally be added (to provide 1-60 ppm free calcium ions, such as about 40 ppm free calcium ions). After such treatment, the liquefied starch will typically have a "dextrose equivalent" (DE) of 10-16.

Generally liquefaction and liquefaction conditions are well known in the art.

Saccharification may be carried out using conditions well-known in the art with a carbohydrate-source generating enzyme, in particular a glucoamylase, or a beta-amylase and optionally a debranching enzyme, such as an isoamylase or a pullulanase. For instance, a full saccharification step may last from about 24 to about 72 hours. However, it is common to do a pre-saccharification of typically 40-90 minutes at a temperature between 30-65° C., typically about 60° C., followed by complete saccharification during fermentation in a simultaneous saccharification and fermentation (SSF) process. Saccharification is typically carried out at a temperature in the range of 20-75° C., e.g., 25-65° C. and 40-70° C., typically around 60° C., and at a pH between about 4 and 5, normally at about pH 4.5.

The saccharification and fermentation steps may be carried out either sequentially or simultaneously. In an embodiment, saccharification and fermentation are performed simultaneously (referred to as "SSF"). However, it is common to perform a pre-saccharification step for about 30 minutes to 2 hours (e.g., 30 to 90 minutes) at a temperature of 30 to 65° C., typically around 60° C. which is followed by a complete saccharification during fermentation referred to as simultaneous saccharification and fermentation (SSF). The pH is usually between 4.2-4.8, e.g., pH 4.5. In a simultaneous saccharification and fermentation (SSF) process, there is no holding stage for saccharification, rather, the yeast and enzymes are added together.

In a typical saccharification process, maltodextrins produced during liquefaction are converted into dextrose by adding a glucoamylase and optionally a debranching enzyme, such as an isoamylase (U.S. Pat. No. 4,335,208) or a pullulanase. The temperature is lowered to 60° C., prior to the addition of the glucoamylase and debranching enzyme. The saccharification process proceeds for 24-72 hours. Prior to addition of the saccharifying enzymes, the pH is reduced to below 4.5, while maintaining a high temperature (above 95° C.), to inactivate the liquefying alpha-amylase. This process reduces the formation of short oligosaccharide called "panose precursors," which cannot be hydrolyzed properly by the debranching enzyme. Normally, about 0.2-0.5% of the saccharification product is the branched trisaccharide panose (Glc pα1-6Glc pα1-4Glc), which cannot be degraded by a pullulanase. If active amylase from the liquefaction remains present during saccharification (i.e., no denaturing), the amount of panose can be as high as 1-2%, which is highly undesirable since it lowers the saccharification yield significantly.

Other fermentation products may be fermented at conditions and temperatures well known to persons skilled in the art, suitable for the fermenting organism in question.

The fermentation product may be recovered by methods well known in the art, e.g., by distillation.

In a particular embodiment, the process of the invention further comprises, prior to the conversion of a starch-containing material to sugars/dextrins the steps of:

(x) reducing the particle size of the starch-containing material; and (y) forming a slurry comprising the starch-containing material and water.

In an embodiment, the starch-containing material is milled to reduce the particle size. In an embodiment the particle size is reduced to between 0.05-3.0 mm, preferably 0.1-0.5 mm, or so that at least 30%, preferably at least 50%, more preferably at least 70%, even more preferably at least 90% of the starch-containing material fits through a sieve with a 0.05-3.0 mm screen, preferably 0.1-0.5 mm screen.

The aqueous slurry may contain from 10-55 wt. % dry solids (DS), preferably 25-45 wt. % dry solids (DS), more preferably 30-40 wt. % dry solids (DS) of starch-containing material.

Conventional starch-conversion processes, such as liquefaction and saccharification processes are described, e.g., in U.S. Pat. No. 3,912,590, EP 252730 and EP 063909, which are incorporated herein by reference.

In an embodiment, the conversion process degrading starch to lower molecular weight carbohydrate components such as sugars or fat replacers includes a debranching step.

In the case of converting starch into a sugar, the starch is depolymerized. Such a depolymerization process consists of, e.g., a pre-treatment step and two or three consecutive process steps, i.e., a liquefaction process, a saccharification process, and depending on the desired end-product, an optional isomerization process.

When the desired final sugar product is, e.g., high fructose syrup the dextrose syrup may be converted into fructose. After the saccharification process, the pH is increased to a value in the range of 6-8, e.g., pH 7.5, and the calcium is removed by ion exchange. The dextrose syrup is then converted into high fructose syrup using, e.g., an immobilized glucose isomerase.

Production of Fermentation Products

Fermentable sugars (e.g., dextrins, monosaccharides, particularly glucose) are produced from enzymatic saccharification. These fermentable sugars may be further purified and/or converted to useful sugar products. In addition, the sugars may be used as a fermentation feedstock in a microbial fermentation process for producing end-products, such as alcohol (e.g., ethanol, and butanol), organic acids (e.g., succinic acid, 3-HP and lactic acid), sugar alcohols (e.g., glycerol), ascorbic acid intermediates (e.g., gluconate, 2-keto-D-gluconate, 2,5-diketo-D-gluconate, and 2-keto-L-gulonic acid), amino acids (e.g., lysine), proteins (e.g., antibodies and fragment thereof).

In an embodiment, the fermentable sugars obtained during the liquefaction process steps are used to produce alcohol and particularly ethanol. In ethanol production, an SSF process is commonly used wherein the saccharifying enzymes and fermenting organisms (e.g., yeast) are added together and then carried out at a temperature of 30-40° C.

The organism used in fermentation will depend on the desired end-product. Typically, if ethanol is the desired end product yeast will be used as the fermenting organism. In some preferred embodiments, the ethanol-producing microorganism is a yeast and specifically *Saccharomyces* such as strains of *S. cerevisiae* (U.S. Pat. No. 4,316,956). A variety of *S. cerevisiae* are commercially available and these include but are not limited to FALI (Fleischmann's Yeast), SUPERSTART (Alltech), FERMIOL (DSM Specialties), RED STAR and ETHANOL RED™ (Lesaffre) and Angel alcohol yeast (Angel Yeast Company, China), Innova® Drive (Novozymes A/S), Innova® Lift (Novozymes A/S). The amount of starter yeast employed in the methods is an amount effective to produce a commercially significant amount of ethanol in a suitable amount of time, (e.g., to produce at least 10% ethanol from a substrate having between 25-40% DS in less than 72 hours). Yeast cells are generally supplied in amounts of about $10^4$ to about $10^{12}$, and preferably from about $10^7$ to about $10^{10}$ viable yeast count per mL of fermentation broth. After yeast is added to the mash, it is typically subjected to fermentation for about 24-96 hours, e.g., 35-60 hours. The temperature is between about 26-34° C., typically at about 32° C., and the pH is from pH 3-6, e.g., around pH 4-5.

The fermentation may include, in addition to a fermenting microorganisms (e.g., yeast), nutrients, and additional enzymes, including phytases. The use of yeast in fermentation is well known in the art.

In further embodiments, use of appropriate fermenting microorganisms, as is known in the art, can result in fermentation end product including, e.g., glycerol, 1,3-propanediol, gluconate, 2-keto-D-gluconate, 2,5-diketo-D-gluconate, 2-keto-L-gulonic acid, succinic acid, lactic acid, amino acids, and derivatives thereof. More specifically when lactic acid is the desired end product, a *Lactobacillus* sp. (*L. casei*) may be used; when glycerol or 1,3-propanediol are the desired end-products *E. coli* may be used; and when 2-keto-D-gluconate, 2,5-diketo-D-gluconate, and 2-keto-L-gulonic acid are the desired end products, *Pantoea citrea* may be used as the fermenting microorganism. The above enumerated list are only examples and one skilled in the art will be aware of a number of fermenting microorganisms that may be used to obtain a desired end product.

Processes for Producing Fermentation Products from Gelatinized Starch-Containing Material In this aspect, the invention relates to processes for producing fermentation products, especially ethanol, from starch-containing material, which process includes a liquefaction step and sequentially or simultaneously performed saccharification and fermentation steps. Consequently, the invention relates to processes for producing fermentation products from starch-containing material comprising the steps of:

(a) liquefying starch-containing material in the presence of a variant alpha-amylase of the invention;
(b) saccharifying the liquefied material obtained in step (a) using a glucoamylase;
(c) fermenting using a fermenting organism.

In an embodiment, a protease, such as an acid fungal protease or a metallo protease is added before, during and/or after liquefaction. In an embodiment the metalloprotease is derived from a strain of *Thermoascus*, e.g., a strain of *Thermoascus aurantiacus*, especially *Thermoascus aurantiacus* CGMCC No. 0670. In another embodiment the protease is a bacterial protease, particularly a serine protease, more particularly an S8 protease, particularly a protease derived from a strain of *Pyrococcus*, more particularly from *Pyrococcus furiosus* disclosed in U.S. Pat. No. 6,358,726.

A further glucoamylase may be added. In an embodiment the further glucoamylase derived from a strain of *Aspergillus*, e.g., *Aspergillus niger* or *Aspergillus awamori*, a strain of *Talaromyces*, especially *Talaromyces emersonii*; or a strain of *Athelia*, especially *Athelia rolfsii*; a strain of *Trametes*, e.g., *Trametes cingulata*; a strain of *Gloeophyllum*, especially *Gloeophyllum trabeum* or *Gloeophyllum sepiarium*; or a mixture thereof. Other suitable glucoamylases may also be used, see section on "Glucoamylase Present And/Or Added In Saccharification And/Or Fermentation". Saccharification step (b) and fermentation step (c) may be carried out either sequentially or simultaneously. A pullulanase and/or protease may be added during saccharification and/or fermentation when the process is carried out as a sequential saccharification and fermentation process and before or during fermentation when steps (b) and (c) are carried out simultaneously (SSF process). The pullulanase and/or protease may also advantageously be added before liquefaction (pre-liquefaction treatment), i.e., before or during step (a), and/or after liquefaction (post liquefaction treatment), i.e., after step (a). The pullulanase is most advantageously added before or during liquefaction, i.e., before or during step (a). The fermentation product, such as especially ethanol, may optionally be recovered after fermentation, e.g., by distillation. The fermenting organism is preferably yeast, preferably a strain of *Saccharomyces cerevisiae*. In a preferred embodiment, the yeast is expressing the variant glucoamylase of the invention. In a particular embodiment, the process of the invention further comprises, prior to step (a), the steps of:

x) reducing the particle size of the starch-containing material, preferably by milling (e.g., using a hammer mill);
y) forming a slurry comprising the starch-containing material and water.

In an embodiment, the particle size is smaller than a #7 screen, e.g., a #6 screen. A #7 screen is usually used in conventional prior art processes. The aqueous slurry may contain from 10-55, e.g., 25-45 and 30-40, w/w % dry solids (DS) of starch-containing material. The slurry is heated to above the gelatinization temperature and an alpha-amylase variant may be added to initiate liquefaction (thinning). The slurry may in an embodiment be jet-cooked to further gelatinize the slurry before being subjected to alpha-amylase in step (a). Liquefaction may in an embodiment be carried out as a three-step hot slurry process. The slurry is heated to between 60-95° C., preferably between 70-90° C., such as preferably between 80-85° C. at pH 4-6, preferably 4.5-5.5, and alpha-amylase variant, optionally together with a pullulanase and/or protease, preferably metalloprotease, are added to initiate liquefaction (thinning). In an embodiment the slurry may then be jet-cooked at a temperature between 95-140° C., preferably 100-135° C., such as 105-125° C., for about 1-15 minutes, preferably for about 3-10 minutes, especially around about 5 minutes. The slurry is cooled to 60-95° C. and more alpha-amylase and optionally pullulanase and/or protease, preferably metalloprotease, is(are) added to finalize hydrolysis (secondary liquefaction). The liquefaction process is usually carried out at pH 4.0-6, in particular at a pH from 4.5 to 5.5. Saccharification step (b) may be carried out using conditions well known in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 20-75° C., preferably from 40-70° C., typically around 60° C., and at a pH between 4 and 5, normally at about pH 4.5. The most widely used process to produce a fermentation product, especially ethanol, is a simultaneous saccharification and fermentation (SSF) process, in which there is no holding stage for the saccharification, meaning that a fermenting organism, such as yeast, and enzyme(s), may be added together. SSF may typically be carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours.

Protease Present and/or Added During Liquefaction

According to the invention a thermostable protease may in one embodiment be present and/or added during liquefaction together with an alpha-amylase, such as a thermostable alpha-amylase, and optionally a carbohydrate-source generating enzyme, in particular a thermostable glucoamylase or thermostable pullulanase.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In a preferred embodiment the thermostable protease used according to the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section, of which the so-called "AZCL-Casein Assay" is the preferred assay.

There are no limitations on the origin of the protease used in a process of the invention as long as it fulfills the thermostability properties defined below.

The protease may be a variant of, e.g., a wild-type protease as long as the protease has the thermostability properties defined herein.

In an embodiment the protease has a thermostability above 60%, such as above 90%, such as above 100%, such as above 110% at 85° C. as determined using the Zein-BCA assay.

In an embodiment protease has a thermostability between 60-120, such as between 70-120%, such as between 80-120%, such as between 90-120%, such as between 100-120%, such as 110-120% at 85° C. as determined using the Zein-BCA assay.

In one embodiment the thermostable protease is a variant of a metallo protease as defined above. In an embodiment the thermostable protease used in a process of the invention is of fungal origin, such as a fungal metallo protease, such as a fungal metallo protease derived from a strain of the genus *Thermoascus*, preferably a strain of *Thermoascus aurantiacus*, especially *Thermoascus aurantiacus* CGMCC No. 0670 (classified as EC 3.4.24.39).

In an embodiment the thermostable protease is a variant of the mature part of the metallo protease shown in SEQ ID NO: 2 disclosed in WO 2003/048353 or the mature part of SEQ ID NO: 1 in WO 2010/008841 and shown as SEQ ID NO: 4 herein further with mutations selected from below list:

S5*+D79L+S87P+A112P+D142L;
D79L+S87P+A112P+T124V+D142L;
S5*+N26R+D79L+S87P+A112P+D142L;
N26R+T46R+D79L+S87P+A112P+D142L;
T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+Y82F+S87P+A112P+T124V+D142L;
D79L+S87P+A112P+T124V+A126V+D142L;
D79L+S87P+A112P+D142L;
D79L+Y82F+S87P+A112P+D142L;
S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M161C;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;
D79L+Y82F+S87G+A112P+D142L;
S70V+D79L+Y82F+S87G+Y97W+A112P+D142L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A112P+A126V+D142L;
Y82F+S87G+S70V+D79L+D104P+A112P+D142L;
Y82F+S87G+D79L+D104P+A112P+A126V+D142L;
A27K+D79L+Y82F+S87G+D104P+A112P+A126V+D142L;
A27K+Y82F+S87G+D104P+A112P+A126V+D142L;
A27K+D79L+Y82F+D104P+A112P+A126V+D142L;
A27K+Y82F+D104P+A112P+A126V+D142L;
A27K+D79L+S87P+A112P+D142L;
D79L+S87P+D142L.

In an preferred embodiment the thermostable protease is a variant of the metallo protease disclosed as the mature part of SEQ ID NO: 2 disclosed in WO 2003/048353 or the mature part of SEQ ID NO: 1 in WO 2010/008841 or SEQ ID NO: 8 herein with the following mutations:
D79L+S87P+A112P+D142L;
D79L+S87P+D142L; or
A27K+D79L+Y82F+S87G+D104P+A112P+A126V+D142L.

In an embodiment the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 8 herein.

The thermostable protease may also be derived from a bacterium, particularly an S8 protease, more particularly an S8 protease from *Pyrococcus* sp or *Thermococcus* sp.

In an embodiment the thermostable protease is derived from a strain of the bacterium *Pyrococcus*, such as a strain of *Pyrococcus furiosus* (pfu protease).

In an embodiment the protease is one shown as SEQ ID NO: 1 in U.S. Pat. No. 6,358,726-B1 (Takara Shuzo Company) and SEQ ID NO: 7 herein.

In another embodiment the thermostable protease is one disclosed in SEQ ID NO: 7 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 7 herein. The *Pyrococcus furiosus* protease can be purchased from Takara Bio, Japan.

Glucoamylase Present and/or Added in Liquefaction

In an embodiment a glucoamylase is present and/or added in liquefaction step a) in a process of the invention (i.e., oil recovery process and fermentation product production process).

In a preferred embodiment the glucoamylase present and/or added in liquefaction step a) is derived from a strain of the genus *Penicillium*, especially a strain of *Penicillium oxalicum* disclosed as SEQ ID NO: 2 in WO 2011/127802 or SEQ ID NO: 9 herein.

In an embodiment the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NO: 9 herein.

In a preferred embodiment the glucoamylase is a variant of the *Penicillium oxalicum* glucoamylase shown in SEQ ID NO: 2 in WO 2011/127802 or SEQ ID NO: 9 herein having a K79V substitution (using the mature sequence shown in SEQ ID NO: 9 for numbering), such as a variant disclosed in WO 2013/053801.

In an embodiment the *Penicillium oxalicum* glucoamylase has a K79V substitution (using SEQ ID NO: 9 for numbering) and preferably further one of the following substitutions:
T65A; or
Q327F; or
E501V; or
Y504T; or
Y504*; or
T65A+Q327F; or
T65A+E501V; or
T65A+Y504T; or
T65A+Y504*; or
Q327F+E501V; or
Q327F+Y504T; or
Q327F+Y504*; or
E501V+Y504T; or
E501V+Y504*; or
T65A+Q327F+E501V; or
T65A+Q327F+Y504T; or
T65A+E501V+Y504T; or
Q327F+E501V+Y504T; or
T65A+Q327F+Y504*; or
T65A+E501V+Y504*; or
Q327F+E501V+Y504*; or
T65A+Q327F+E501V+Y504T; or
T65A+Q327F+E501V+Y504*;
E501V+Y504T; or
T65A+K161S; or
T65A+Q405T; or
T65A+Q327W; or
T65A+Q327F; or
T65A+Q327Y; or
P11F+T65A+Q327F; or
R1K+D3W+K5Q+G7V+N8S+T10K+P11S+T65A+Q327F; or
P2N+P4S+P11F+T65A+Q327F; or
P11F+D26C+K330+T65A+Q327F; or
P2N+P4S+P11F+T65A+Q327W+E501V+Y504T; or
R1E+D3N+P4G+G6R+G7A+N8A+T10D+P11D+T65A+Q327F; or
P11F+T65A+Q327W; or
P2N+P4S+P11F+T65A+Q327F+E501V+Y504T; or
P11F+T65A+Q327W+E501V+Y504T; or
T65A+Q327F+E501V+Y504T; or
T65A+S105P+Q327W; or
T65A+S105P+Q327F; or
T65A+Q327W+S364P; or
T65A+Q327F+S364P; or
T65A+S103N+Q327F; or
P2N+P4S+P11F+K34Y+T65A+Q327F; or
P2N+P4S+P11F+T65A+Q327F+D445N+V447S; or
P2N+P4S+P11F+T65A+I172V+Q327F; or
P2N+P4S+P11F+T65A+Q327F+N502*; or
P2N+P4S+P11F+T65A+Q327F+N502T+P563S+K571E; or
P2N+P4S+P11F+R31S+K33V+T65A+Q327F+N564D+K571S; or
P2N+P4S+P11F+T65A+Q327F+S377T; or
P2N+P4S+P11F+T65A+V325T+Q327W; or
P2N+P4S+P11F+T65A+Q327F+D445N+V447S+E501V+Y504T; or
P2N+P4S+P11F+T65A+I172V+Q327F+E501V+Y504T; or
P2N+P4S+P11F+T65A+Q327F+S377T+E501V+Y504T; or
P2N+P4S+P11F+D26N+K34Y+T65A+Q327F; or
P2N+P4S+P11F+T65A+Q327F+I375A+E501V+Y504T; or
P2N+P4S+P11F+T65A+K218A+K221D+Q327F+E501V+Y504T; or
P2N+P4S+P11F+T65A+S103N+Q327F+E501V+Y504T; or
P2N+P4S+T10D+T65A+Q327F+E501V+Y504T; or
P2N+P4S+F12Y+T65A+Q327F+E501V+Y504T; or
K5A+P11F+T65A+Q327F+E501V+Y504T; or
P2N+P4S+T10E+E18N+T65A+Q327F+E501V+Y504T; or
P2N+T10E+E18N+T65A+Q327F+E501V+Y504T; or
P2N+P4S+P11F+T65A+Q327F+E501V+Y504T+T568N; or
P2N+P4S+P11F+T65A+Q327F+E501V+Y504T+K524T+G526A; or
P2N+P4S+P11F+K34Y+T65A+Q327F+D445N+V447S+E501V+Y504T; or
P2N+P4S+P11F+R31S+K33V+T65A+Q327F+D445N+V447S+E501V+Y504T; or
P2N+P4S+P11F+D26N+K34Y+T65A+Q327F+E501V+Y504T; or
P2N+P4S+P11F+T65A+F80*+Q327F+E501V+Y504T; or
P2N+P4S+P11F+T65A+K112S+Q327F+E501V+Y504T; or
P2N+P4S+P11F+T65A+Q327F+E501V+Y504T+T516P+K524T+G526A; or
P2N+P4S+P11F+T65A+Q327F+E501V+N502T+Y504*; or
P2N+P4S+P11F+T65A+Q327F+E501V+Y504T; or
P2N+P4S+P11F+T65A+S103N+Q327F+E501V+Y504T; or
K5A+P11F+T65A+Q327F+E501V+Y504T; or
P2N+P4S+P11F+T65A+Q327F+E501V+Y504T+T516P+K524T+G526A; or P2N+P4S+P11F+T65A+K79A+Q327F+E501V+Y504T; or
P2N+P4S+P11F+T65A+K79G+Q327F+E501V+Y504T; or
P2N+P4S+P11F+T65A+K79I+Q327F+E501V+Y504T; or
P2N+P4S+P11F+T65A+K79L+Q327F+E501V+Y504T; or
P2N+P4S+P11F+T65A+K79S+Q327F+E501V+Y504T; or
P2N+P4S+P11F+T65A+L72V+Q327F+E501V+Y504T; or
S255N+Q327F+E501V+Y504T; or
P2N+P4S+P11F+T65A+E74N+V79K+Q327F+E501V+Y504T; or
P2N+P4S+P11F+T65A+G220N+Q327F+E501V+Y504T; or
P2N+P4S+P11F+T65A+Y245N+Q327F+E501V+Y504T; or
P2N+P4S+P11F+T65A+Q253N+Q327F+E501V+Y504T; or
P2N+P4S+P11F+T65A+D279N+Q327F+E501V+Y504T; or
P2N+P4S+P11F+T65A+Q327F+S359N+E501V+Y504T; or
P2N+P4S+P11F+T65A+Q327F+D370N+E501V+Y504T; or
P2N+P4S+P11F+T65A+Q327F+V460S+E501V+Y504T; or
P2N+P4S+P11F+T65A+Q327F+V460T+P468T+E501V+Y504T; or
P2N+P4S+P11F+T65A+Q327F+T463N+E501V+Y504T; or
P2N+P4S+P11F+T65A+Q327F+S465N+E501V+Y504T; or
P2N+P4S+P11F+T65A+Q327F+T477N+E501V+Y504T.

In a preferred embodiment the glucoamylase present and/or added in liquefaction is the *Penicillium oxalicum* glucoamylase having a K79V substitution and preferably further one of the following substitutions:
P11F+T65A+Q327F;
P2N+P4S+P11F+T65A+Q327F (using SEQ ID NO: 9 for numbering).

In an embodiment the glucoamylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 9 herein. The glucoamylase may be added in amounts from 0.1-100 micro grams EP/g, such as 0.5-50 micro grams EP/g, such as 1-25 micrograms EP/g, such as 2-12 micrograms EP/g DS.

Glucoamylase Present and/or Added in Saccharification and/or Fermentation

A glucoamylase is present and/or added in saccharification and/or fermentation, preferably simultaneous saccharification and fermentation (SSF), in a process of the invention (i.e., oil recovery process and fermentation product production process).

In an embodiment the glucoamylase present and/or added in saccharification and/or fermentation is of fungal origin, preferably from a stain of *Aspergillus*, preferably *A. niger, A. awamori*, or *A. oryzae*; or a strain of *Trichoderma*, preferably *T. reesei*; or a strain of *Talaromyces*, preferably *T. emersonii* or a strain of *Trametes*, preferably *T. cingulata*, or a strain of *Pycnoporus*, or a strain of *Gloeophyllum*, such as *G. serpiarium* or *G. trabeum*, or a strain of the *Nigrofomes*.

In an embodiment the glucoamylase is derived from *Talaromyces*, such as a strain of *Talaromyces emersonii*, such as the one shown in SEQ ID NO: 10 herein, In an embodiment the glucoamylase is selected from the group consisting of:
(i) a glucoamylase comprising the polypeptide of SEQ ID NO: 10 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 10 herein.

In an embodiment the glucoamylase is derived from a strain of the genus *Pycnoporus*, in particular a strain of *Pycnoporus sanguineus* described in WO 2011/066576 (SEQ ID NOs 2, 4 or 6), such as the one shown as SEQ ID NO: 4 in WO 2011/066576, or in SEQ ID NO: 11 herein.

In an embodiment the glucoamylase is selected from the group consisting of:
(i) a glucoamylase comprising the polypeptide of SEQ ID NO: 11 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 11 herein.

In an embodiment the glucoamylase is derived from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is the *Gloeophyllum sepiarium* shown in SEQ ID NO: 2 in WO 2011/068803 or SEQ ID NO: 12 herein.

In a preferred embodiment the glucoamylase is derived from *Gloeophyllum* serpiarium, such as the one shown in SEQ ID NO: 12 herein. In an embodiment the glucoamylase is selected from the group consisting of:
(i) a glucoamylase comprising the polypeptide of SEQ ID NO: 12 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 12 herein.

In another embodiment the glucoamylase is derived from *Gloeophyllum trabeum* such as the one shown in SEQ ID NO: 13 herein. In an embodiment the glucoamylase is selected from the group consisting of:
(i) a glucoamylase comprising the polypeptide of SEQ ID NO: 13 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 13 herein.

In an embodiment the glucoamylase is derived from a strain of the genus *Nigrofomes*, in particular a strain of *Nigrofomes* sp. disclosed in WO 2012/064351.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Commercially available compositions comprising glucoamylase include AMG 200 L; AMG 300 L; SANT™ SUPER, SANT™ EXTRA L, SPIRIZYME™ PLUS, SPI- RIZYME™ FUEL, SPIRIZYME™ B4U, SPIRIZYME™ ULTRA, SPIRIZYME™ EXCEL and AMG™ E (from Novozymes A/S); OPTIDEX™ 300, GC480, GC417 (from DuPont); AMIGASE™ and AMIGASE™ PLUS (from DSM); G-ZYME™ G900, G-ZYME™ and G990 ZR (from DuPont).

According to a preferred embodiment of the invention the glucoamylase is present and/or added in saccharification and/or fermentation in combination with an alpha-amylase. Examples of suitable alpha-amylase are described below.

Alpha-Amylase Present and/or Added in Saccharification and/or Fermentation

In an embodiment an alpha-amylase is present and/or added in saccharification and/or fermentation in a process of the invention. In a preferred embodiment the alpha-amylase is of fungal or bacterial origin. In a preferred embodiment the alpha-amylase is a fungal acid stable alpha-amylase. A fungal acid stable alpha-amylase is an alpha-amylase that has activity in the pH range of 3.0 to 7.0 and preferably in the pH range from 3.5 to 6.5, including activity at a pH of about 4.0, 4.5, 5.0, 5.5, and 6.0.

In a preferred embodiment the alpha-amylase present and/or added in saccharification and/or fermentation is derived from a strain of the genus *Rhizomucor*, preferably a strain the *Rhizomucor pusillus*, such as one shown in SEQ ID NO: 3 in WO 2013/006756, such as a *Rhizomucor pusillus* alpha-amylase hybrid having an *Aspergillus niger* linker and starch-binding domain, such as the one shown in SEQ ID NO: 14 herein, or a variant thereof.

In an embodiment the alpha-amylase present and/or added in saccharification and/or fermentation is selected from the group consisting of:
(i) an alpha-amylase comprising the polypeptide of SEQ ID NO: 14 herein;
(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 14 herein.

In a preferred embodiment the alpha-amylase is a variant of the alpha-amylase shown in SEQ ID NO: 14 having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 14 for numbering).

In an embodiment the alpha-amylase is derived from a *Rhizomucor pusillus* with an *Aspergillus niger* glucoamylase linker and starch-binding domain (SBD), preferably disclosed as SEQ ID NO: 9 herein, preferably having one or more of the following substitutions: G128D, D143N, preferably G128D+D143N (using SEQ ID NO: 14 for numbering).

In an embodiment the alpha-amylase variant present and/or added in saccharification and/or fermentation has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 14 herein.

In a preferred embodiment the ratio between glucoamylase and alpha-amylase present and/or added during saccharification and/or fermentation may preferably be in the range from 500:1 to 1:1, such as from 250:1 to 1:1, such as from 100:1 to 1:1, such as from 100:2 to 100:50, such as from 100:3 to 100:70.

Pullulanase Present and/or Added in Liquefaction and/or Saccharification and/or Fermentation.

A pullulanase may be present and/or added during liquefaction step a) and/or saccharification step b) or fermentation step c) or simultaneous saccharification and fermentation.

Pullulanases (E.C. 3.2.1.41, pullulan 6-glucano-hydrolase), are debranching enzymes characterized by their ability to hydrolyze the alpha-1,6-glycosidic bonds in, for example, amylopectin and pullulan.

Contemplated pullulanases according to the present invention include the pullulanases from *Bacillus amyloderamificans* disclosed in U.S. Pat. No. 4,560,651 (hereby incorporated by reference), the pullulanase disclosed as SEQ ID NO: 2 in WO 01/51620 (hereby incorporated by reference), the *Bacillus deramificans* disclosed as SEQ ID NO: 4 in WO 01/51620 (hereby incorporated by reference), and the pullulanase from *Bacillus acidopullulyticus* disclosed as SEQ ID NO: 6 in WO 01/51620 (hereby incorporated by reference) and also described in FEMS Mic. Let. (1994) 115, 97-106.

The pullulanase may according to the invention be added in an effective amount which include the preferred amount of about 0.0001-10 mg enzyme protein per gram DS, preferably 0.0001-0.10 mg enzyme protein per gram DS, more preferably 0.0001-0.010 mg enzyme protein per gram DS. Pullulanase activity may be determined as NPUN. An Assay for determination of NPUN is described in the "Materials & Methods"-section below.

Suitable commercially available pullulanase products include PROMOZYME D, PROMOZYME™ D2 (Novozymes A/S, Denmark), OPTIMAX L-300 (Genencor Int., USA), and AMANO 8 (Amano, Japan).

The fermentation product, such as especially ethanol, may optionally be recovered after fermentation, e.g., by distillation. Suitable starch-containing starting materials are listed in the section "Starch-Containing Materials"-section below. In an embodiment the starch-containing materials is corn or wheat.

The fermenting organism is preferably yeast, preferably a strain of *Saccharomyces*, especially a strain of *Saccharomyces cerevisae*. Suitable fermenting organisms are listed in the "Fermenting Organisms"-section above. In a preferred embodiment steps ii) and iii) are carried out sequentially or simultaneously (i.e., as SSF process). The aqueous slurry may contain from 10-55 wt.-% dry solids, preferably 25-45 wt.-% dry solids, more preferably 30-40 wt.-% dry solids of starch-containing material. The slurry is heated to above the initial gelatinization temperature. Alpha-amylase, preferably bacterial alpha-amylase, may be added to the slurry. In an embodiment the slurry is also jet-cooked to further gelatinize the slurry before being subjected to an alpha-amylase in liquefaction step i).

The temperature during step (i) is above the initial gelatinization temperature, such as between 80-90° C., such as around 85° C.

In an embodiment liquefaction is carried out as a three-step hot slurry process. The slurry is heated to between 60-95° C., preferably between 80-90° C., and alpha-amylase is added to initiate liquefaction (thinning). Then the slurry is jet-cooked at a temperature between 95-140° C., preferably 105-125° C., for 1-15 minutes, preferably for 3-10 minutes, especially around 5 minutes. The slurry is cooled to 60-95° C., preferably 80-90° C., and more alpha-amylase is added to finalize hydrolysis (secondary liquefaction). The liquefaction process is usually carried out at pH 4.5-6.5, such as around 4.8, or a pH between 5.0-6.2, such as 5.0-6.0, such as between 5.0-5.5, such as around 5.2, such as around 5.4, such as around 5.6, such as around 5.8. Milled and liquefied starch is known as "mash".

The saccharification in step ii) may be carried out using conditions well known in the art. For instance, a full saccharification process may last up to from about 24 to about 72 hours. In an embodiment a pre-saccharification step is done at 40-90 minutes at a temperature between 30-65° C., typically at about 60° C., followed by complete saccharification during fermentation in a simultaneous saccharification and fermentation step (SSF). Saccharification is typically carried out at temperatures from 30-70° C., such as 55-65° C., typically around 60° C., and at a pH between 4 and 5, normally at about pH 4.5.

The most widely used process in fermentation product production, especially ethanol production, is simultaneous saccharification and fermentation (SSF) process, in which there is no holding stage for the saccharification.

SSF may typically be carried out at a temperature between 25° C. and 40° C., such as between 28° C. and 36° C., such as between 30° C. and 34° C., such as around 32° C., when the fermentation organism is yeast, such as a strain of Saccharomyces cerevisiae, and the desired fermentation product is ethanol. In an embodiment fermentation is ongoing for 6 to 120 hours, in particular 24 to 96 hours.

Other fermentation products may be fermented at conditions and temperatures, well known to the skilled person in the art, suitable for the fermenting organism in question.

Fermentation Medium

The environment in which fermentation is carried out is often referred to as the "fermentation media" or "fermentation medium". The fermentation medium includes the fermentation substrate, that is, the carbohydrate source that is metabolized by the fermenting organism. According to the invention the fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms

The term "fermenting organism" refers to any organism, including bacterial and fungal organisms, especially yeast, suitable for use in a fermentation process and capable of producing the desired fermentation product. Especially suitable fermenting organisms are able to ferment, i.e., convert, sugars, such as glucose or maltose, directly or indirectly into the desired fermentation product, such as ethanol. Examples of fermenting organisms include fungal organisms, such as yeast. Preferred yeast includes strains of Saccharomyces spp., in particular, Saccharomyces cerevisiae. Suitable concentrations of the viable fermenting organism during fermentation, such as SSF, are well known in the art or can easily be determined by the skilled person in the art. In one embodiment the fermenting organism, such as ethanol fermenting yeast, (e.g., Saccharomyces cerevisiae) is added to the fermentation medium so that the viable fermenting organism, such as yeast, count per mL of fermentation medium is in the range from $10^5$ to $10^{12}$, preferably from $10^7$ to $10^{10}$, especially about $5\times10^7$.

Examples of commercially available yeast includes, e.g., RED START™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties), Innova® Drive (Novozymes A/S), Innova® Lift (Novozymes A/S).

Starch-Containing Materials

Any suitable starch-containing material may be used according to the present invention. The starting material is generally selected based on the desired fermentation product. Examples of starch-containing materials, suitable for use in a process of the invention, include whole grains, corn, wheat, barley, rye, milo, sago, cassava, tapioca, sorghum, rice, peas, beans, or sweet potatoes, or mixtures thereof or starches derived therefrom, or cereals. Contemplated are also waxy and non-waxy types of corn and barley. In a preferred embodiment the starch-containing material, used for ethanol production according to the invention, is corn or wheat.

Fermentation Products

The term "fermentation product" means a product produced by a process including a fermentation step using a fermenting organism. Fermentation products contemplated according to the invention include alcohols (e.g., ethanol, methanol, butanol; polyols such as glycerol, sorbitol and inositol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferably processes of the invention are used for producing an alcohol, such as ethanol. The fermentation product, such as ethanol, obtained according to the invention, may be used as fuel, which is typically blended with gasoline. However, in the case of ethanol it may also be used as potable ethanol.

Recovery of Fermentation Products

Subsequent to fermentation, or SSF, the fermentation product may be separated from the fermentation medium. The slurry may be distilled to extract the desired fermentation product (e.g., ethanol). Alternatively the desired fermentation product may be extracted from the fermentation medium by micro or membrane filtration techniques. The fermentation product may also be recovered by stripping or other method well known in the art.

The present invention is further disclosed in the following numbered embodiments.

Embodiment 1

An alpha-amylase variant comprising substitutions at positions corresponding to positions 268 and 293 of SEQ ID NO: 1, in particular substitutions selected from the group consisting of:

268G+293Y; 268G+293F; 268G+293W; 268G+293H; 268G+293A; 268G+293Q; 268A+293Y; 268A+293F; 268A+293W; 268A+293H; 268A+293A; 268A+293Q; 268P+293Y; 268P+293F; 268P+293W; 268P+293H; 268P+293A; 268P+293Q; 268S+293Y; 268S+293F; 268S+293W; 268S+293H; 268S+293A; 268S+293Q; 268T+293Y; 268T+293F; 268T+293W; 268T+293H; 268T+293A; 268T+293Q; 268V+293Y; 268V+293F; 268V+293W; 268V+293H; 268V+293A; 268V+293Q; 268I+293Y; 268I+293F; 268I+293W; 268I+293H; 268I+293A; 268I+293Q; 268L+293Y; 268L+293F; 268L+293W; 268L+293H; 268L+293A; 268L+293Q; 268M+293Y; 268M+293F; 268M+293W; 268M+293H; 268M+293A; 268M+293Q; and wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of SEQ ID NO: 1, SEQ ID NO: 2, SEQ ID NO: 3, SEQ ID NO: 4, and SEQ ID NO: 18.

Embodiment 2

The alpha-amylase variant according to embodiment 1, wherein the substitutions are selected from the group consisting of: Y268G+N293Y; Y268G+N293F; Y268G+N293W; Y268G+N293H; Y268G+N293A; Y268A+N293Y; Y268P+N293Y; Y268S+N293Y.

Embodiment 3

The variant of embodiment 1 or 2, further having a substitution corresponding to T297N of SEQ ID NO: 1.

Embodiment 4

The variant of any of embodiments 1-3, wherein the variant comprises the substitutions Y268G+N293Y+T297N.

Embodiment 5

The variant of any of embodiments 1-4, further comprising the substitutions corresponding to V59A+E129V+K177L+R179E+V212T+Q254S+M284V of SEQ ID NO: 1.

Embodiment 6

The variant of any of embodiments 1-5, wherein the variant has increased thermo-stability, particularly increased stability measured as residual alpha-amylase activity after heat-stress, compared to a parent alpha-amylase, particularly a parent amylase selected from the group consisting of SEQ ID NO: 1, SEQ ID NO: 2, SEQ ID NO: 3, SEQ ID NO: 4, SEQ ID NO: 5, and SEQ ID NO: 18.

Embodiment 7

The variant of any of embodiments 1-6, wherein the increased thermo-stability is determined as Half-life Improvement Factor (HIF), and wherein the HIF is at least 1.1, at least 1.2, at least 1.3, at least 1.4, at least 1.5, at least 1.6, at least 1.7, at least 1.8, at least 1.9, at least 2.0.

Embodiment 8

The variant of any of embodiments 1-7, wherein the variant further comprises one of the specific combinations of substitutions or deletions selected from:

H208Y+N217R;
R,E179S+A184Q+E188P+T191N;
I389K+R392K+D393L;
W115D+D117Q+T133P;
T24K+K25R+A27Q+E29D+N32H+Q86S+A90S+A93S;
Q86S+A90S+A93S;
D385E+I389K+R392K+D393N;
G416S+T417S+E418S+K419V;
T21Q+T24N+K25R;
T21Q+T24N+K25R+E29D;
T21Q+Q86K+D117Q+S173N+H208Y+S382H;
R,E179S+A184Q+E188P+T191N+S242Y;
and, wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, and SEQ ID NO: 18.

Embodiment 9

The variants according to embodiment 8, wherein the variant has increased thermo-stability, particularly increased stability measured as residual alpha-amylase activity determined by EnzCheck assay after 15 min incubation at 95° C., pH 4.5, 5 ppm $Ca^{2+}$, compared to a parent alpha-amylase, particularly a parent amylase selected from SEQ ID NO: 5.

Embodiment 10

The variant of any of embodiments 1-7, wherein the variant further comprises one of the specific combinations of substitutions or deletions selected from:
G112A;
T309W;
T312W;
T309W+T312W;
R,E179G;
T212I;
S173N;
K141H;
T50I;
G108A;
T398R;
P320A;
T225N;
S382H;
I277L+G282H;
L36Q;
A91I;
P258E;
T21Q;
T133P+E179G;
A304N;
S406W;
A2*+P3*;
D328E+E333Q;
E210D;
L16T+T21K+L22Q+T24D;
N127Y+E188P;
and, wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, and SEQ ID NO: 18.

Embodiment 11

The variants according to embodiment 10, wherein the variant has increased thermo-stability, particularly increased stability measured as residual alpha-amylase activity determined by EnzCheck assay after 30 min incubation at 95° C., pH 4.5, 5 ppm $Ca^{2+}$, compared to a parent alpha-amylase, particularly a parent amylase selected from SEQ ID NO: 5.

Embodiment 12

The variant of any of embodiments 1-7, wherein the variant further comprises one of the specific combinations of substitutions or deletions selected from:
G112A,
T309W
T312W
T309W+T312W
T212I
E210D
L16T T21K L22Q T24D
N127Y E188P
E179S A184Q E188P T191N
E188P
E188P K279F
E188P K279Y
E188P K279W
E188P K279H
W115D D117Q T133P; and
wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, and SEQ ID NO: 18.

Embodiment 13

The variant of any of embodiments 1-7, wherein the variant further comprises one of the specific combinations of substitutions or deletions selected from:
W115D+D117Q+T133P;
E188P;
E188P+N275F;
E188P+N275H;
E188P+K279F;
E188P+K279Y;
E188P+K279W;
E188P+K279H;
R, E179S+A184Q+E188P+T191N;
E188P+S242Y+I479V;
E188P+S242Y+F403L;
E188P+S242Y+K279Y;
G180*+I181*+E188P+N193F+S242Y;
E188P+S242Y;
T21Q+Q86K+D117Q+S173N+E188P+H208Y+S242Y+S382H;
S173N+E188P+S242Y;
E188P+K279I;
R, E179S+A184Q+E188P+T191N+S242Y+K279W;
R, E179S+A184Q+E188P+T191N+S242Y+K279I;
E188P+S242Y+K279I;
E188P+N193F+S242Y;
T21Q+T24N+K25R+E29D+E188P+S242Y;
E188P+S242Y+K279F;
E188P+S242Y+K279W+F449L;
E188P+S242Y+K279H; and
wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, and SEQ ID NO: 18.

Embodiment 14

The variant according to any of embodiments 12-13, wherein the variant has increased thermo-stability, and wherein increased thermo-stability is expressed as an improvement factor (IF), and wherein the variant have an improvement factor greater than 1.0 and wherein the improvement factor is calculated as the ratio of retained activity (measured as ratio of DP3/DP4+ at 91° C. to DP3/DP4+ at 85° C.) for a given variant to the retained activity of the the amylase of SEQ ID NO: 5.

Embodiment 15

The variant of embodiment 14, wherein the improvement factor is at least 1.05, at least 1.1, at least 1.2, at least 1.3, at least 1.4, at least 1.5, at least 1.6.

Embodiment 16

The variant of any of embodiments 1-13, wherein the variant has increased thermo-stability at pH 4.5-5.0, particularly increased stability determined as an improvement factor (IF) over the parent alpha-amylase, wherein the IF is determined as residual activity of the variant alpha-amylase (ratio of activity in a themo-stressed sample over activity in a sample incubated at 4° C.) over residual activity of the parent alpha-amylase (ratio of activity in a themo-stressed sample over activity in a sample incubated at 4° C.), in particular the variants have an IF of at least 1.1, at least 1.2, at least 1.3, at least 1.4, at least 1.5, at least 1.6, at least 1.7, at least 1.8, at least 1.9, at least 2.0 compared to the alpha-amylase of SEQ ID NO: 1, SEQ ID NO: 2, SEQ ID NO: 3, SEQ ID NO: 4, SEQ ID NO: 5, and SEQ ID NO: 18.

Embodiment 17

The variant according to any of the preceding embodiments wherein the variant further comprises a deletion of two amino acids in the region corresponding to positions 179-182 using SEQ ID NO: 1 for numbering.

Embodiment 18

The variant according to embodiment 14, wherein the deletion is selected from the group consisting of 179*+180*, 179*+181*, 179*+182*, 180*+181*, 180*+182*, and 181*+182*, particularly I181*+G182*.

Embodiment 19

The variant according to any of embodiments 1-18, further comprising substitution N193F using SEQ ID NO: 1 for numbering.

Embodiment 20

The variant of embodiment 1, wherein the variant alpha-amylase is isolated.

Embodiment 21

The variant of any of embodiments 1-20, wherein the number of alterations is 1-20, e.g., 1-10 and 1-5, such as 1, 2, 3, 4, 5, 6, 7, 8, 9 or 10 alterations.

Embodiment 22

The variant of any of embodiments 1-21, wherein the variant has increased specific activity compared to the parent alpha-amylase measured in the same assay under the same conditions, particularly compared to a parent alpha-amylase selected from the group of SEQ ID NO: 1, SEQ ID NO: 2, SEQ ID NO: 3, SEQ ID NO: 4, SEQ ID NO: 5, and SEQ ID NO: 18.

Embodiment 23

A polynucleotide encoding the variant of any of embodiments 1-22.

Embodiment 24

A composition comprising the variant alpha-amylase of any of the embodiments 1-22.

Embodiment 25

The composition of embodiment 24, wherein the composition further comprises a second alpha-amylase having at least 70%, at least 75%, at least 80%, at least 85%, at least 90%, at least 95%, at least 96%, at least 97%, at least 98%, or at least 99% sequence identity to SEQ ID NO: 17 or SEQ ID NO: 6.

Embodiment 26

The composition according to embodiment 25, wherein the second alpha-amylase is selected from the group consisting of an alpha-amylases having at least 70%, at least 75%, at least 80%, at least 85%, at least 90%, at least 95%, at least 96%, at least 97%, at least 98%, or at least 99% sequence identity to SEQ ID NO: 15 and wherein the second alpha-amylase comprises the substitutions: G48A+T49I+H68W+G107A+H156Y+A181T+E185P+N190F+A209V+Q264S+K176L+F201Y+H205Y+K213T+E255P+Q360S+D416V+R437W using SEQ ID NO: 17 for numbering.

Embodiment 27

The composition according to any of the embodiments 24-26, wherein the alpha-amylase according to any of the embodiments 1-22 is selected from an alpha-amylase having at least 70%, at least 75%, at least 80%, at least 85%, at least 90%, at least 95%, at least 96%, at least 97%, at least 98%, or at least 99% sequence identity to SEQ ID NO: 1 and wherein the alpha-amylase comprises the substitutions V59A+E129V+K177L+V212T+Q254S+M284V+Y268G+N293Y+T297N, and further a combination of substitutions selected from:
R179E+W115D+D117Q+T133P;
R179E+E188P+K279W;
R179S+A184Q+E188P+T191N+S242Y+K279I;
R179S+A184Q+E188P+T191N;
S173N+R179E+E188P+H208Y+S242Y+K279I.

Embodiment 28

The composition according to embodiment 27, wherein the alpha-amylase further comprises a deletion selected from the group consisting of 179*+180*, 179*+181*, 179*+182*, 180*+181*, 180*+182*, and 181*+182*, particularly I181*+G182*.

Embodiment 29

The composition according to any of embodiments 27-28, wherein the alpha-amylase further comprises the substitution N193F.

Embodiment 30

The composition according to any of embodiments 24-29, further comprising a protease, particularly an S8 protease, more particularly an S8 protease from Pyrococcus or Thermococcus, more particularly a protease having at least 70%, at least 75%, at least 80%, at least 85%, at least 90%, at least 95%, at least 96%, at least 97%, at least 98%, or at least 99% sequence identity to SEQ ID NO: 7.

Embodiment 31

A nucleic acid construct comprising the polynucleotide of embodiment 23.

Embodiment 32

An expression vector comprising the polynucleotide of embodiment 23, or the nucleic acid construct of embodiment 31.

Embodiment 33

A host cell comprising the polynucleotide of embodiment 23.

Embodiment 34

A method of producing an alpha-amylase variant of embodiments 1-22, comprising: cultivating the host cell of embodiment 33 under conditions suitable for expression of the variant; and optionally recovering the variant.

Embodiment 35

A use of the variant of any of embodiments 1-22 or the composition according to any of embodiment 24-30 for liquefying a starch-containing material.

Embodiment 36

A use of the variant of any of embodiments 1-22 in a detergent.

Embodiment 37

A process for producing a syrup from starch-containing material comprising the steps of:
a) liquefying the starch-containing material at a temperature above the initial gelatinization temperature in the presence of a variant alpha-amylase according to embodiment 1-22 or a composition of embodiment 24-30; and
b) saccharifying the product of step a) in the presence of a glucoamylase.

Embodiment 38

The process according to embodiment 37, wherein step b) is performed in the presence of a glucoamylase and:
i) a fungal alpha-amylase;
ii) an isoamylase;
iii) a fungal alpha-amylase and an isoamylase.

Embodiment 39

The process according to any of embodiments 37-38, wherein a pullulanase is present in step a) and/or b).

Embodiment 40

The process according to embodiment 37 further comprising:
c) fermenting the product of step b) using a fermenting organism to produce a fermentation product.

Embodiment 41

The process of embodiment 40, wherein the fermenting organism is a yeast and the fermentation product is alcohol.

Embodiment 42

The process of embodiment 41, wherein the yeast is *Saccharomyces cerevisiae* and the alcohol is ethanol.

Embodiment 43

The process of any of embodiments 40-42, wherein steps b) and c) are performed simultaneously.

Embodiment 44

The process of embodiment 43, wherein saccharification and fermentation is performed at a temperature between 25° C. and 40° C., such as between 28° C. and 36° C., such as between 30° C. and 34° C., such as around 32° C.

Embodiment 45

The process of any of embodiments 40-44, wherein fermentation is ongoing for 6 to 120 hours, in particular 24 to 96 hours, at a pH of 4-6.

Embodiment 46

The process of embodiment 37, wherein liquefaction is performed at a temperature between 65-95° C., particularly between 75-95° C., more particularly between 80-92° C., at pH 4.5-6.5, such as around 4.8, or a pH between 5.0-6.2, such as 5.0-6.0, such as between 5.0-5.5, such as around 5.2, such as around 5.4, such as around 5.6, such as around 5.8.

Embodiment 47

The process of embodiment 37, wherein saccharification is performed at temperatures from 30-70° C., such as 55-65° C., typically around 60° C., and at a pH between 4 and 5, normally at about pH 4.5.

The present invention is further described by the following examples that should not be construed as limiting the scope of the invention.

EXAMPLES

Alpha-Amylase Assays:
pNP-G7 Assay

The alpha-amylase activity may be determined by a method employing the G7-pNP substrate. G7-pNP which is an abbreviation for 4,6-ethylidene($G_7$)-p-nitrophenyl($G_1$)-α, D-maltoheptaoside, a blocked oligosaccharide which can be cleaved by an endo-amylase, such as an alpha-amylase. Following the cleavage, the alpha-Glucosidase included in the kit digest the hydrolysed substrate further to liberate a free PNP molecule which has a yellow color and thus can be measured by visible spectophometry at λ=405 nm (400-420 nm.). Kits containing G7-pNP substrate and alpha-Glucosidase is manufactured by Roche/Hitachi (cat. No. 11876473).
Reagents:

The G7-pNP substrate from this kit contains 22 mM 4,6-ethylidene-G7-pNP and 52.4 mM HEPES (2-[4-(2-hydroxyethyl)-1-piperazinyl]-ethanesulfonic acid), pH 7.0).

The alpha-Glucosidase reagent contains 52.4 mM HEPES, 87 mM NaCl, 12.6 mM $MgCl_2$, 0.075 mM $CaCl_2$, ≥4 kU/L alpha-glucosidase).

The substrate working solution is made by mixing 1 mL of the alpha-Glucosidase reagent with 0.2 mL of the G7-pNP substrate. This substrate working solution is made immediately before use.

Dilution buffer: 50 mM MOPS, 0.05% (w/v) Triton X100 (polyethylene glycol p-(1,1,3,3-tetramethylbutyl)-phenyl ether ($C_{14}H_{22}O(C_2H_4O)_n$, (n=9–10))), 1 mM $CaCl_2$), pH8.0.
Procedure:

The amylase sample to be analyzed is diluted in dilution buffer to ensure the pH in the diluted sample is 7. The assay is performed by transferring 20 µl diluted enzyme samples to 96 well microtiter plate and adding 80 µl substrate working solution. The solution is mixed and pre-incubated 1 minute at room temperature and absorption is measured every 20 sec. over 5 minutes at OD405 nm.

The slope (absorbance per minute) of the time dependent absorption-curve is directly proportional to the specific activity (activity per mg enzyme) of the alpha-amylase in question under the given set of conditions. The amylase sample should be diluted to a level where the slope is below 0.4 absorbance units per minute.
Phadebas Activity Assay:

The alpha-amylase activity may also be determined by a method using the Phadebas substrate (from for example Magle Life Sciences, Lund, Sweden). A Phadebas tablet includes interlinked starch polymers that are in the form of globular microspheres that are insoluble in water. A blue dye is covalently bound to these microspheres. The interlinked starch polymers in the microsphere are degraded at a speed that is proportional to the alpha-amylase activity. When the alpha-amylase degrades the starch polymers, the released blue dye is water soluble and concentration of dye can be determined by measuring absorbance at 620 nm. The concentration of blue is proportional to the alpha-amylase activity in the sample.

The amylase sample to be analyzed is diluted in activity buffer with the desired pH. One substrate tablet is suspended in 5 mL activity buffer and mixed on magnetic stirrer. During mixing of substrate transfer 150 µl to microtiter plate (MTP) or PCR-MTP. Add 30 µl diluted amylase sample to 150 µl substrate and mix. Incubate for 15 minutes at 37° C.

The reaction is stopped by adding 30 µl 1 M NaOH and mix. Centrifuge MTP for 5 minutes at 4000×g. Transfer 100 µl to new MTP and measure absorbance at 620 nm.

The amylase sample should be diluted so that the absorbance at 620 nm is between 0 and 2.2, and is within the linear range of the activity assay.

Reducing Sugar Activity Assay:

The alpha-amylase activity can also be determined by reducing sugar assay with for example corn starch substrate. The number of reducing ends formed by the alpha-amylase hydrolysing the alpha-1,4-glycosidic linkages in starch is determined by reaction with p-Hydroxybenzoic acid hydrazide (PHBAH). After reaction with PHBAH the number of reducing ends can be measured by absorbance at 405 nm and the concentration of reducing ends is proportional to the alpha-amylase activity in the sample.

The corns starch substrate (3 mg/ml) is solubilised by cooking for 5 minutes in milliQ water and cooled down before assay. For the stop solution prepare a Ka-Na-tartrate/NaOH solution (K—Na-tartrate (Merck 8087) 50 g/l, NaOH 20 g/l) and prepare freshly the stop solution by adding p-Hydroxybenzoic acid hydrazide (PHBAH, Sigma H9882) to Ka-Na-tartrate/NaOH solution to 15 mg/ml.

In PCR-MTP 50 µl activity buffer is mixed with 50 µl substrate. Add 50 µl diluted enzyme and mix. Incubate at the desired temperature in PCR machine for 5 minutes. Reaction is stopped by adding 75 µl stop solution (Ka-Na-tartrate/NaOH/PHBAH). Incubate in PCR machine for 10 minutes at 95° C. Transfer 150 µl to new MTP and measure absorbance at 405 nm.

The amylase sample should be diluted so that the absorbance at 405 nm is between 0 and 2.2, and is within the linear range of the activity assay.

EnzChek® assay: EnzChek® Ultra Amylase assay kit, E33651, Molecular Probes was used.

Assay Principle

The thermostability of a reference alpha-amylase and alpha-amylase variants thereof was determined by incubating the reference alpha-amylase and variants at pH in range from 4.5-5.0 and temperatures in range of 75-95° C. (for specific pH and temperatures see examples below) in the presence of 0.9% w/v corn starch, 0.12 mM $CaCl_2$ and 2 mM NaCl followed by determination of residual activity using the EnzChek® substrate (EnzChek® Ultra Amylase assay kit, E33651, Molecular Probes). Residual activity was determined relative to control samples, which were incubated at room temperature at low sodium and starch concentration The residual activity (% RA) was calculated as Activity in heat stressed sample/Activity in control sample*100. Before calculating the residual activity, it was ensured that the activity of the heat stressed samples and in the control samples were within the linear range of the activity assay. The linear range can be determined by measuring the activity of a range of standards (typically 0-100 ng/mL) of the reference amylase.

Assuming logarithmic decay, half life time (T½ (min)) was calculated using the equation: T½ (min)=T(min)*LN (0.5)/LN(% RA/100), where T is assay incubation time in minutes, and % RA is % residual activity determined in assay. Half-life improvement factor (HIF) was calculated as: Half-life improvement Factor (HIF) of variant=(half-life (T½) of the variant/half-life (T½) of the reference backbone).

The specific procedure is explained in more detail in the examples below.

Example 1: Thermostability of Alpha-Amylase Variants at pH 5.0

Assay Principle

The thermostability of a reference alpha-amylase and alpha-amylase variants thereof was determined by incubating the reference alpha-amylase and variants at pH 4.5 and temperatures of 75° C. in the presence of 0.9% w/v corn starch, 0.12 mM $CaCl_2$) and 2 mM NaCl followed by determination of residual activity using the EnzChek® substrate (EnzChek® Ultra Amylase assay kit, E33651, Molecular Probes). Residual activity was determined relative to control samples, which were incubated at room temperature at low sodium and starch concentration.

Materials

Enzyme Dilution Buffer: 10 mM potassium acetate, 0.01% Triton X-100, 0.125 mM $CaCl_2$, pH adjusted to 4.5 using 1M HCl or 2 M KOH Stability Buffer: 100 mM potassium acetate, 0.01% Triton X100, 0.12 mM $CaCl_2$, 2.17 mM NaCl and 1% starch from corn, pH 4.5 using 1 M HCl or 2M KOH Residual Activity Buffer: 100 mM potassium acetate, 0.01% Triton X100, 0.12 mM $CaCl_2$, pH adjusted to 5.5 using 1 M HCl or 2M KOH Substrate Buffer: 50 mM Sodium acetate, adjusted to pH 4.0 using 1 M HCl or 1 M NaOH Substrate: 1 mg/mL BODIPY® FL labelled DQTM starch substrate (from EnzChek® Ultra Amylase assay kit, E33651, Molecular Probes) in Substrate Buffer Substrate Working Solution: Substrate diluted 10-fold in Residual Activity Buffer Procedure The residual activity is determined at two final enzyme concentrations 2 ng/mL and 4 ng/mL. Samples having activities outside the linear range were excluded from the calculation of residual activity. Within the linear range, the average residual activity is used.

Purified enzyme samples were diluted to working concentrations of 1 ppm (micrograms/ml) in Enzyme Dilution Buffer.

10 µL enzyme and 140 µL Stability Buffer (15× dilution) was transferred to a 96-well PCR microtiter plate and mixed (Plate 1) in duplicates. After mix the enzyme concentration was 66.6 ng/mL and the concentrations of the buffer components were 92 mM potassium acetate, 0.01% Triton X-100, 0.12% $CaCl_2$, 1 mM NaCl, and 0.9% starch From Plate 1, an aliquot of 15 µL was transferred to a new plate (Plate 2) together with 235 µL Residual Activity Buffer, Enzyme concentration after dilution was 4 ng/mL and the concentrations of the buffer components were 99% potassium acetate, 0.01% Triton X-100, 0.12% $CaCl_2$, 0.1 mM NaCl and 0.09% starch.

Plate 2 was stored at room temperature and used as control samples.

The remaining part of the samples in Plate 1 were heat stressed by incubation for 40 minutes at 75° C. in PCR machine (Bio-Rad T100 Thermal Cycler).

After incubation, samples on Plate 1 were diluted 16.6-fold (15 µL sample+235 µL Residual Activity Buffer) to a final enzyme concentration of 4 ng/mL.

Incubated samples and control samples were further diluted 2-fold (100 µL sample+100 µL Residual Activity Buffer) to a final enzyme concentration of 2 ng/mL For the activity measurements, 25 µL diluted enzyme (both 2 ng/mL and 4 ng/mL samples) were transferred to black 384-well microtiter plates.

Reaction was started by adding 25 μL Substrate Working Solution.

Immediately after addition of Substrate, fluorescence was read at 25° C. every minute for 15 minutes (Ex: 485 nm, Em: 555 nm). Activity was determined from the slope of measured fluorescence versus time.

The residual activity (% RA) was calculated as Activity in heat stressed sample/Activity in control sample*100. Before calculating the residual activity, it was ensured that the activity of the heat stressed samples and in the control samples were within the linear range of the activity assay. The linear range can be determined by measuring the activity of a range of standards (typically 0-100 ng/mL) of the reference amylase.

Assuming logarithmic decay, half life time (T½(min)) was calculated using the equation: T½ (min)=T(min)*LN (0.5)/LN(% RA/100), where T is assay incubation time in minutes, and % RA is % residual activity determined in assay. Half-life improvement factor (HIF) was calculated as: Half-life improvement Factor (HIF) of variant=(half-life (T½) of the variant/half-life (T½) of the reference backbone).

Using this assay setup, the half-life time was determined as a measure of thermostability for the reference alpha-amylase and variants thereof as shown in Tables 1.

TABLE 1

| Mutations using SEQ ID NO: 1 for numbering | Half-life (min) | HIF (rel. SEQ ID NO: 4) | HIF (rel. SEQ ID NO: 5) |
| --- | --- | --- | --- |
| Control amylase V59A + E129V + K177L + R179E + Q254S + M284V + V212T + I181* + G182* | 38.65 | 1.00 | 0.46 |
| V59A + E129V + K177L + R179E + Q254S + M284V + V212T + I181* + G182* + Y268G + N293Y + T297N | 88.24 | 2.35 | 1.00 |

The results demonstrate an improved stability of the variant alpha-amylase over the control amylase disclosed in SEQ ID NO: 4.

Example 2. Thermostability Assay for Alpha-Amylase Variants at pH 5.0

Assay Principle

The thermostability of a reference alpha-amylase (SEQ ID NO: 5 a derivative of SEQ ID NO: 1) and alpha-amylase variants thereof was determined by incubating the reference alpha-amylase and variants at pH 5.0 and temperatures of 95° C. in the presence of 0.9% w/v corn starch, 0.12 mM $CaCl_2$) and 2. mM NaCl followed by determination of residual activity using the EnzChek® substrate (EnzChek® Ultra Amylase assay kit, E33651, Molecular Probes). Residual activity was determined relative to control samples, which were incubated at room temperature at low sodium and starch concentration.

Materials

| | |
| --- | --- |
| Enzyme Dilution Buffer: | 10 mM potassium acetate, 0.01% Triton X-100, 0.125 mM $CaCl_2$, pH adjusted to 5.0 using 1M HCl or 2M KOH |
| Stability Buffer: | 100 mM potassium acetate, 0.01% Triton X100, 0.12 mM $CaCl_2$, 2.17 mM NaCl and 1% starch from corn, pH 5.0 using 1M HCl or 2M KOH |
| Residual Activity Buffer: | 100 mM potassium acetate, 0.01% Triton X100, 0.12 mM $CaCl_2$, pH adjusted to 5.5 using 1M HCl or 2M KOH) |
| Substrate Buffer: | 50 mM Sodium acetate, adjusted to pH 4.0 using 1M HCl or 1M NaOH |
| Substrate: | 1 mg/mL BODIPY ® FL labelled DQTM starch substrate (from EnzChek ® Ultra Amylase assay kit, E33651, Molecular Probes) in Substrate Buffer |
| Substrate Working Solution: | Substrate diluted 10-fold in Residual Activity Buffer |

Procedure Examples for 12 and 24 ng/mL Final Enzyme Concentration

The residual activity is determined at two final enzyme concentrations (either 8 ng/mL and 16 ng/mL or 12 ng/mL and 24 ng/mL). Samples having activities outside the linear range were excluded from the calculation of residual activity. Within the linear range, the average residual activity is used.

Purified enzyme samples were diluted to working concentrations of 2.4 ppm (micrograms/ml) in Enzyme Dilution Buffer.

15 μL enzyme and 135 μL Stability Buffer was transferred to a 96-well PCR microtiter plate and mixed (Plate 1) in duplicates. After mix the enzyme concentration was 240 ng/mL and the concentrations of the buffer components were 92 mM potassium acetate, 0.01% Triton X-100, 0.12% $CaCl_2$, 1 mM NaCl, and 0.9% starch From Plate 1, an aliquot of 16 μL was transferred to a new plate (Plate 2) together with 144 μL Residual Activity Buffer, Enzyme concentration after dilution was 24 ng/mL and the concentrations of the buffer components were 99% potassium acetate, 0.01% Triton X-100, 0.12% $CaCl_2$, 0.1 mM NaCl and 0.09% starch.

Plate 2 was stored at room temperature and used as control samples.

The remaining part of the samples in Plate 1 were heat stressed by incubation for 15 or 30 minutes at 95° C. in PCR machine (Bio-Rad T100 Thermal Cycler).

After incubation, samples on Plate 1 were diluted 10-fold (16 μL sample+144 μL Residual Activity Buffer) to a final enzyme concentration of 24 ng/mL.

Incubated samples and control samples were further diluted 2-fold (67 μL sample+67 μL Residual Activity Buffer) to a final enzyme concentration of 12 ng/mL For the activity measurements, 25 μL diluted enzyme (both 12 ng/mL and 24 ng/mL samples) were transferred to black 384-well microtiter plates.

Reaction was started by adding 25 μL Substrate Working Solution.

Immediately after addition of Substrate, fluorescence was read at 25° C. every minute for 10 minutes (Ex: 485 nm, Em: 555 nm). Activity was determined from the slope of measured fluorescence versus time.

The residual activity (% RA) was calculated as Activity in heat stressed sample/Activity in control sample*100. Before calculating the residual activity, it was ensured that the activity of the heat stressed samples and in the control samples were within the linear range of the activity assay. The linear range can be determined by measuring the activity of a range of standards (typically 0-100 ng/mL) of the reference amylase.

Assuming logarithmic decay, half life time (T½(min)) was calculated using the equation:

$$T^{1/2}\min = t_{min} \times \frac{\ln(0.5)}{\ln\left(\frac{RA}{100}\right)}$$

where T is assay incubation time in minutes, and % RA is % residual activity determined in assay. Using this assay setup, the half-life time was determined as a measure of thermostability for the reference alpha-amylase and variants thereof as shown in Tables 2 and 3.

TABLE 2

Half-life improvement factor (HIF) after heat shock based on residual activity measurements

| Substitution added to control | Incubation T [° C.] | Incubation time [min] | HIF relative to SEQ ID NO: 5 |
|---|---|---|---|
| Control | 95° C. | 15 min | 1.0 |
| H208Y + N217R | 95° C. | 15 min | 1.15 |
| E179S + A184Q + E188P + T191N | 95° C. | 15 min | 1.22 |
| I389K + R392K + D393L | 95° C. | 15 min | 1.15 |
| W115D + D117Q + T133P | 95° C. | 15 min | 1.19 |
| T24K + K25R + A27Q + E29D + N32H + Q86S + A90S A93S | 95° C. | 15 min | 1.18 |
| Q86S + A90S + A93S | 95° C. | 15 min | 1.32 |
| D385E + I389K + R392K + D393N | 95° C. | 15 min | 1.15 |
| G416S + T417S + E418S + K419V | 95° C. | 15 min | 1.22 |
| T21Q + T24N + K25R | 95° C. | 15 min | 1.73 |
| T21Q + T24N + K25R + E29D | 95° C. | 15 min | 1.51 |
| T21Q + Q86K + D117Q + S173N + H208Y + S382H | 95° C. | 15 min | 1.15 |
| E179S + A184Q + E188P + T191N + S242Y | 95° C. | 15 min | 1.53 |

TABLE 3

Half-life improvement factor (HIF) after heat shock based on residual activity measurements

| Substitution added to control | Incubation T [° C.] | Incubation time [min] | HIF relative to SEQ ID NO: 5 |
|---|---|---|---|
| Control | 95° C. | 30 min | 1.0 |
| G112A | 95° C. | 30 min | 1.37 |
| T309W | 95° C. | 30 min | 1.12 |
| T312W | 95° C. | 30 min | 1.47 |
| T309W + T312W | 95° C. | 30 min | 1.55 |
| E179G | 95° C. | 30 min | 1.39 |
| T212I | 95° C. | 30 min | 1.18 |
| S173N | 95° C. | 30 min | 3.09 |
| K141H | 95° C. | 30 min | 1.18 |
| T50I | 95° C. | 30 min | 1.15 |
| G108A | 95° C. | 30 min | 1.18 |
| T398R | 95° C. | 30 min | 1.37 |
| P320A | 95° C. | 30 min | 1.10 |
| T225N | 95° C. | 30 min | 1.10 |
| S382H | 95° C. | 30 min | 1.20 |
| I277L + G282H | 95° C. | 30 min | 1.14 |
| L36Q | 95° C. | 30 min | 1.20 |
| A91I | 95° C. | 30 min | 1.20 |
| P258E | 95° C. | 30 min | 1.14 |
| T21Q | 95° C. | 30 min | 1.34 |
| T133P + E179G | 95° C. | 30 min | 1.55 |
| A304N | 95° C. | 30 min | 1.18 |
| S406W | 95° C. | 30 min | 1.13 |
| A2* + P3* | 95° C. | 30 min | 1.20 |
| D328E + E333Q | 95° C. | 30 min | 1.13 |
| E210D | 95° C. | 30 min | 1.13 |
| L16T + T21K + L22Q + T24D | 95° C. | 30 min | 1.13 |
| N127Y + E188P | 95° C. | 30 min | 1.23 |

The results demonstrate an improved stability of all variant alpha-amylases over the control amylase disclosed in SEQ ID NO: 5.

Example 3. Thermostability of Alpha Amylase Variants in Liquefaction

A slurry of whole ground corn thin stillage and tap water was prepared to 32% dry solids and pH was adjusted to 5.0 with either 45% w/v potassium hydroxide or 40% v/v sulfuric acid; thin stillage was blended at 30% weight of backset per weight of slurry. Approximately, 4.5 grams of corn slurry was added to. Glass vials and were capped with a screw cap. Mass of the slurry was determined by weighing the vial before and after addition of slurry. Alpha amylase was dosed at 2.1 μg/g dry solids just prior to liquefaction in a shaking heater block. Incubation in the heater block was for two hours at a set point of 85 or 91° C. Samples were run in duplicate or triplicate. Sampling was done by adding approximately 0.5 g of liquefact to 4.5 ml of 5 mM H2SO4. Diluted samples were mixed and filtered through a 0.45 μm Whatman PP filter. Samples were stored at 4° C. prior to and during HPLC analysis.

HPLC analysis: HPLC analysis used an Agilent 1100/1200 combined with a Bio-Rad HPX-87H ion Exclusion column (300 mm×7.8 mm) and a Bio-Rad Cation H guard cartridge. The mobile phase was 0.005 M sulfuric acid and processed samples at a flow rate of 0.6 ml/min, with column and RI detector temperatures of 65 and 55° C., 10 respectively. The method quantified analytes using calibration standards for DP4+, DP3, DP2, glucose, fructose, acetic acid, lactic acid, glycerol and ethanol (% w/v). A four point calibration including the origin is used for quantification. The ratio of DP3 to DP4+ was used to evaluate the progress of liquefaction. A Retained Activity was calculated as the ratio of DP3/DP4+ at 91° C. to DP3/DP4+ at 85° C. The Improvement Factor is the ratio of the Retained Activity for a given variant to the Retained activity of the control.

TABLE 4

Performance of Alpha Amylase Variants at 91° C. compared to a control alpha-amylase disclosed in SEQ ID NO: 5.

| Curated mutation relative to control (SEQ ID NO: 5) | Improvement Factor |
|---|---|
| Control | 1.000 |
| G112A | 1.021 |
| T309W | 1.136 |
| T312W | 1.217 |
| T309W + T312W | 1.228 |
| T212I | 1.094 |
| E210D | 1.219 |

TABLE 4-continued

Performance of Alpha Amylase Variants at 91° C. compared to a control alpha-amylase disclosed in SEQ ID NO: 5.

| Curated mutation relative to control (SEQ ID NO: 5) | Improvement Factor |
|---|---|
| L16T T21K L22Q T24D | 1.178 |
| N127Y E188P | 1.393 |
| E179S A184Q E188P T191N | 1.422 |
| E188P | 1.567 |
| E188P K279F | 2.174 |
| E188P K279Y | 2.440 |
| E188P K279W | 2.788 |
| E188P K279H | 1.842 |
| W115D D117Q T133P | 1.663 |

The results demonstrate an improved performance in liquefaction of the tested variant alpha-amylases over the control amylase disclosed in SEQ ID NO: 5.

Example 4. Variants of the Invention Tested in Liquefaction at pH 5.0

A slurry of whole ground corn and tap water was prepared to 32% dry solids and pH was adjusted to 5.0 with either 45% w/v potassium hydroxide or 40% v/v sulfuric acid. Approximately, 4.5 grams of corn slurry was added to glass vials that were capped with a screw cap. Mass of the slurry was determined by weighing the vial before and after addition of slurry. Alpha amylase was dosed at 2.1 μg/g dry solids just prior to liquefaction in a shaking heater block. Incubation in the heater block was for two hours at a set point of 85 or 91° C. Samples were run in triplicate. Sampling was done by adding approximately 0.5 g of liquefact to 4.5 ml of 5 mM H2SO4. Diluted samples were mixed and filtered through a 0.45 μm Whatman PP filter. Samples were stored at 4° C. prior to and during HPLC analysis.

HPLC analysis: HPLC analysis used an Agilent 1100/1200 combined with a Bio-Rad HPX-87H ion Exclusion column (300 mm×7.8 mm) and a Bio-Rad Cation H guard cartridge. The mobile phase was 0.005 M sulfuric acid and processed samples at a flow rate of 0.6 ml/min, with column and RI detector temperatures of 65 and 55° C., 10 respectively. The method quantified analytes using calibration standards for DP4+, DP3, DP2, glucose, fructose, acetic acid, lactic acid, glycerol and ethanol (% w/v). A four point calibration including the origin was used for quantification.

The ratio of DP3 to DP4+ was used to evaluate the progress of liquefaction. A Retained Activity was calculated as the ratio of DP3/DP4+ at 91° C. to DP3/DP4+ at 85° C. The Improvement Factor is the ratio of the Retained Activity for a given variant to the Retained activity of the control.

TABLE 5

Performance of Alpha Amylase variants at 91° C. compared to a control alpha-amylase disclosed in SEQ ID NO: 5.

| Curated mutation relative to control (SEQ ID NO: 5) | Improvement Factor |
|---|---|
| Control | 1.000 |
| W115D D117Q T133P | 1.276 |
| E188P | 1.125 |
| E188P N275F | 1.138 |
| E188P N275H | 1.079 |
| E188P K279F | 1.531 |
| E188P K279Y | 1.562 |
| E188P K279W | 1.752 |
| E188P K279H | 1.267 |
| E179S A184Q E188P T191N | 1.653 |
| E188P S242Y I479V | 1.249 |
| E188P S242Y F403L | 1.704 |
| E188P S242Y K279Y | 1.729 |
| G180* I181* E188P N193F S242Y | 1.210 |
| E188P S242Y | 1.461 |
| T21Q Q86K D117Q S173N E188P H208Y S242Y S382H | 1.156 |
| S173N E188P S242Y | 1.447 |
| E188P K279I | 1.944 |
| E179S A184Q E188P T191N S242Y K279W | 1.436 |
| E179S A184Q E188P T191N S242Y K279I | 1.616 |
| E188P S242Y K279I | 1.619 |
| E188P N193F S242Y | 1.456 |
| T21Q T24N K25R | 1.036 |
| E29D E188P S242Y | |
| E188P S242Y K279F | 1.295 |
| E188P S242Y K279W F449L | 1.085 |
| E188P S242Y K279H | 1.378 |

The results demonstrate an improved performance in liquefaction of all the tested variant alpha-amylases over the control amylase disclosed as SEQ ID NO: 5.

Example 5. Variants of the Invention Tested in Viscosity Reduction after Liquefaction at 91° C.

For liquefaction, sixteen slurries of whole ground corn and tap water were prepared to a total weight of 100 g targeting 32.50% Dry Solids (DS) in canisters. Initial slurry pH was approximately 6.0 and was adjusted to 5.0 with 40% v/v sulfuric acid. The alpha amylases were dose at 2.1 μg EP/gDS. Enzymes were added to each canister, and then each canister was sealed and mixed well prior to loading into the Labomat. All samples were incubated in the Labomat set to the following conditions: 6° C./min. Ramp to 80° C., hold for 2 min, Ramp to 90° C. at 1° C./min, Ramp to 91° C. at 0.2° C./min and holding for 115 min., 40 rpm for 30 seconds to the left and 30 seconds to the right. Once liquefaction was complete, all canisters were cooled in an ice bath for approximately 20 minutes before proceeding to viscosity measurement. For viscosity measurement, approximately 30 g of mash was transferred into canisters for a Super4 RVA Viscometer (Perten Instruments). The instrument was at 160 rpm mixing for 4 minutes at 32° C. An average of the viscosity over the final minute was used for the viscosity determination.

TABLE 6

Final viscosity of liquefacts cooked at 91° C. and treated with the listed alpha amylases.

| Curated mutation relative to control (SEQ ID NO: 5) | Viscosity at 32° C. (cp) |
|---|---|
| Control | 588 |
| E179S A184Q E188P T191N | 511 |

TABLE 6-continued

Final viscosity of liquefacts cooked at 91° C. and treated with the listed alpha amylases.

| Curated mutation relative to control (SEQ ID NO: 5) | Viscosity at 32° C. (cp) |
|---|---|
| W115D D117Q T133P | 446 |
| E188P | 517 |
| E188P N275F | 452 |
| E188P K279Y | 414 |
| E188P K279W | 394 |
| E188P K279H | 468 |
| E188P S242Y F403L | 376 |
| E188P S242Y K279Y | 379 |
| E188P K279I | 339 |
| E179S A184Q E188P T191N S242Y K279I | 359 |
| T21Q T24N K25R E29D E188P S242Y | 486 |
| E188P S242Y K279F | 524 |
| E188P S242Y K279W F449L | 463 |

All tested variants showed a reduction in viscosity over the control.

Example 6. Low pH Stability of *Bacillus stearothermophilus* Alpha-Amylase Variants of the Invention Using standard site directed methods, amino acid substitutions were introduced in a variant of the *Bacillus stearothermophilus* alpha-amylase (SEQ ID NO: 1) having a deletion of the amino acids in position 181 and 182. The substitutions are indicated in the table below and the position numbering is according to SEQ ID NO: 1. The modified amylase genes were transformed into and expressed in *Bacillus subtilis*. The *Bacillus subtilis* broths were centrifuged and the amylase containing supernatants isolated and diluted 10 times in 100 mM K-acetate pH 4.5 with 5 ppm $CaCl_2$. The samples were then split in two samples; one was stored at 4° C. and the other was incubated at 70° C. for 30 minutes. Following that, the samples were diluted 10 times in assay buffer (100 mM Britton-Robinson buffer (100 mM acetic acid+100 mM phosphate acid+100 mM boric acid)+0.12 mM $CaCl_2$+0.01% Brij, pH adjusted to pH 7.3) and the amylase activity measured using Phadebas amylase assay as described under methods. The residual activities were calculated as the ratio between the activity in the samples that have been incubated at 70° C. relative to activity in the samples that have been incubated at 4° C. Further the improvement factor (IF) is calculated as the ratio of the residual activity of the amylase variant divided by the residual activity of the reference amylase. For variants with two substitutions the improvement factor is also calculated by comparing to the residual activity for the variant with only one of the substitutions, i.e. IF-2 is improvement over the variant with a Y268G substitution and IF-3 is improvement over the variant with N293Y substitution.

TABLE 7

Residual activity (RA) of alpha-amylase variants after incubation in pH 4.5 at 70° C. for 30 min.

| | IF | IF-2 | IF-3 |
|---|---|---|---|
| Ref (I181* G182*) | 1.00 | | |
| Y268G | 0.41 | 1.00 | |
| Y268G + N293Y | 1.25 | 3.05 | |
| Y268G + N293F | 1.79 | 4.35 | |
| Y268G + N293W | 0.97 | 2.35 | |
| Y268G + N293H | 2.24 | 5.45 | |
| Y268G + N293A | 1.32 | 3.20 | |
| N293Y | 1.12 | | 1.00 |
| Y268A + N293Y | 1.09 | | 0.98 |
| Y268P + N293Y | 1.23 | | 1.11 |
| Y268S + N293Y | 3.03 | | 2.71 |

This example demonstrates that alpha-amylase variants, introduced in an amylase reference with a deletion of two amino acids in positions 181 and 182 (SEQ ID NO: 1), with substitution in N293 to W, Y, F, H, A OR a and/or in Y268 to G, A, P, S have increased stability at low pH relative to the reference.

Example 7. Increased Specific Activity of the Variant Alpha-Amylases of the Invention Variants of the invention also has increased specific activity compared to their parent alpha-amylase. The specific activity for an amylase variant of the invention can be determined for a purified sample of the variant amylase with a known protein concentration and compared to the specific activity for the reference amylase measured in the same assay and under the same conditions. Assays using natural starch, amylose or amylopectin combined with measuring formation of reducing ends are examples of relevant assay for the invention. Assays are described in Example section under alpha-amylase assays, e.g., the Phadebas activity assay. The amylase variants may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. An alpha-amylase variant comprising substitutions at positions corresponding to positions 268 and 293 of SEQ ID NO: 1, wherein the substitutions are selected from the group consisting of:

268G+293Y; 268G+293F; 268G+293W; 268G+293H; 268G+293A; 268G+293Q; 268A+293Y; 268A+293F; 268A+293W; 268A+293H; 268A+293A; 268A+293Q; 268P+293Y; 268P+293F; 268P+293W; 268P+293H; 268P+293A; 268P+293Q; 268S+293Y; 268S+293F; 268S+293W; 268S+293H; 268S+293A; 268S+293Q; 268T+293Y; 268T+293F; 268T+293W; 268T+293H; 268T+293A; 268T+293Q; 268V+293Y; 268V+293F; 268V+293W; 268V+293H; 268V+293A; 268V+293Q; 268I+293Y; 268I+293F; 268I+293W; 268I+293H; 268I+293A; 268I+293Q; 268L+293Y; 268L+293F; 268L+293W; 268L+293H; 268L+293A; 268L+293Q; 268M+293Y; 268M+293F; 268M+293W; 268M+293H; 268M+293A; 268M+293Q; and wherein the variant has at least 70%, but less than 100% sequence identity to a parent alpha amylase selected from the group consisting of SEQ ID NO: 1, SEQ ID NO: 2, SEQ ID NO: 3, SEQ ID NO: 4, and SEQ ID NO: 18.

2. The alpha-amylase variant according to claim 1, wherein the substitutions are selected from the group consisting of: Y268G+N293Y; Y268G+N293F; Y268G+N293W; Y268G+N293H; Y268G+N293A; Y268A+N293Y; Y268P+N293Y; and Y268S+N293Y.

3. The variant of claim 1, further having a substitution corresponding to T297N of SEQ ID NO: 1.

4. The variant of claim 1, wherein the variant comprises the substitutions Y268G+N293Y+T297N.

5. The variant of claim 1, wherein the variant further comprises one of the specific combinations of substitutions or deletions selected from the group consisting of:
H208Y+N217R;
R,E179S+A184Q+E188P+T191N;
I389K+R392K+D393L;
W115D+D117Q+T133P;
T24K+K25R+A27Q+E29D+N32H+Q86S+A90S+A93S;
Q86S+A90S+A93S;
D385E+I389K+R392K+D393N;
G416S+T417S+E418S+K419V;
T21Q+T24N+K25R;
T21Q+T24N+K25R+E29D;
T21Q+Q86K+D117Q+S173N+H208Y+S382H;
R,E179S+A184Q+E188P+T191N+S242Y;
and, wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, and SEQ ID NO: 18.

6. The variant of claim 1, wherein the variant further comprises one of the specific combinations of substitutions or deletions selected from:
G112A;
T309W;
T312W;
T309W+T312W;
R,E179G;
T212I;
S173N;
K141H;
T50I;
G108A;
T398R;
P320A;
T225N;
S382H;
I277L+G282H;
L36Q;
A91I;
P258E;
T21Q;
T133P+E179G;
A304N;
S406W;
A2*+P3*;
D328E+E333Q;
E210D;
L16T+T21K+L22Q+T24D;
N127Y+E188P;
and, wherein the variant has at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of:
SEQ ID NO: 1, SEQ ID NO: 2, SEQ ID NO: 3, SEQ ID NO: 4, SEQ ID NO: 5, and SEQ ID NO: 18.

7. The variant of claim 1, wherein the variant further comprises one of the specific combinations of substitutions or deletions selected from:
G112A;
T309W;
T312W;
T309W+T312W;
T212I;
E210D;
L16T+T21K+L22Q+T24D;
N127Y E188P
E179S A184Q E188P T191N
E188P
E188P K279F
E188P K279Y
E188P K279W
E188P K279H
W115D D117Q T133P; and
wherein the variant has at least 70%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, and SEQ ID NO: 18.

8. The variant of claim 1, wherein the variant further comprises one of the specific combinations of substitutions or deletions selected from:
W115D+D117Q+T133P;
E188P;
E188P+N275F;
E188P+N275H;
E188P+K279F;
E188P+K279Y;
E188P+K279W;
E188P+K279H;
R, E179S+A184Q+E188P+T191N;
E188P+S242Y+I479V;
E188P+S242Y+F403L;
E188P+S242Y+K279Y;
G180*+I181*+E188P+N193F+S242Y;
E188P+S242Y;
T21Q+Q86K+D117Q+S173N+E188P+H208Y+S242Y+S382H;
S173N+E188P+S242Y;
E188P+K279I;
R, E179S+A184Q+E188P+T191N+S242Y+K279W;
R, E179S+A184Q+E188P+T191N+S242Y+K279I;
E188P+S242Y+K279I;
E188P+N193F+S242Y;
T21Q+T24N+K25R+E29D+E188P+S242Y;
E188P+S242Y+K279F;
E188P+S242Y+K279W+F449L;
E188P+S242Y+K279H; and
wherein the variant has at least 70%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, and SEQ ID NO: 18.

9. A polynucleotide encoding the variant of claim 1.

10. A nucleic acid construct comprising the polynucleotide of claim 9.

11. An expression vector comprising the nucleic acid construct of claim 10.

12. An isolated host cell comprising the polynucleotide of claim 9.

13. A method of producing an alpha-amylase variant having alpha-amylase activity, comprising:
cultivating the host cell of claim 12 under conditions suitable for expression of the variant; and optionally recovering the variant.

14. A process for liquefying a starch-containing material, comprising contacting the starch-containing material with a variant of claim 1.

15. A process for producing a syrup from starch-containing material comprising the steps of:
   a) liquefying the starch-containing material at a temperature above the initial gelatinization temperature in the presence of a variant alpha-amylase according to claim 1; and
   b) saccharifying the product of step a) in the presence of a glucoamylase.

16. The variant alpha-amylase of claim 1, wherein the variant has at least 75%, but less than 100% sequence identity to a parent alpha amylase selected from the group consisting of SEQ ID NO: 1, SEQ ID NO: 2, SEQ ID NO: 3, SEQ ID NO: 4, and SEQ ID 18.

17. The variant alpha-amylase of claim 1, wherein the variant has at least 80%, but less than 100% sequence identity to a parent alpha amylase selected from the group consisting of SEQ ID NO: 1, SEQ ID NO: 2, SEQ ID NO: 3, SEQ ID NO: 4, and SEQ ID 18.

18. The variant alpha-amylase of claim 1, wherein the variant has at least 85%, but less than 100% sequence identity to a parent alpha amylase selected from the group consisting of SEQ ID NO: 1, SEQ ID NO: 2, SEQ ID NO: 3, SEQ ID NO: 4, and SEQ ID 18.

19. The variant alpha-amylase of claim 1, wherein the variant has at least 90%, but less than 100% sequence identity to a parent alpha amylase selected from the group consisting of SEQ ID NO: 1, SEQ ID NO: 2, SEQ ID NO: 3, SEQ ID NO: 4, and SEQ ID 18.

20. The variant alpha-amylase of claim 1, wherein the variant has at least 95%, but less than 100% sequence identity to a parent alpha amylase selected from the group consisting of SEQ ID NO: 1, SEQ ID NO: 2, SEQ ID NO: 3, SEQ ID NO: 4, and SEQ ID 18.

21. The variant alpha-amylase of claim 1, wherein the variant has at least 99%, but less than 100% sequence identity to a parent alpha amylase selected from the group consisting of SEQ ID NO: 1, SEQ ID NO: 2, SEQ ID NO: 3, SEQ ID NO: 4, and SEQ ID 18.

22. A composition comprising the variant alpha-amylase of claim 1 and a second alpha-amylase.

23. The composition of claim 22, wherein the second alpha-amylase has at least 70% sequence identity to SEQ ID NO: 17 or SEQ ID NO: 6.

24. The composition of claim 22, wherein the second alpha-amylase has at least 70% sequence identity to SEQ ID NO: 15 and wherein the second alpha-amylase comprises the substitutions: G48A+T49I+H68W+G107A+H156Y+A181T+E185P+N190F+A209V+Q264S+K176L+F201Y+H205Y+K213T+E255P+Q360S+D416V+R437W using SEQ ID NO: 17 for numbering.

25. The composition of claim 22, wherein the variant alpha-amylase has at least 70% sequence identity to SEQ ID NO: 1 and comprises the substitutions V59A+E129V+K177L+V212T+Q254S+M284V+Y268G+N293Y+T297N, and further a combination of substitutions selected from:
   R179E+W115D+D117Q+T133P;
   R179E+E188P+K279W;
   R179S+A184Q+E188P+T191N+S242Y+K279I;
   R179S+A184Q+E188P+T191N;
   S173N+R179E+E188P+H208Y+S242Y+K279I.

26. The composition of claim 25, wherein the alpha-amylase further comprises a deletion selected from the group consisting of 179*+180*, 179*+181*, 179*+182*, 180*+181*, 180*+182*, and 181*+182*.

27. The composition of claim 26, wherein the alpha-amylase comprises the deletions I181*+G182*.

28. The composition of claim 26, wherein the alpha-amylase further comprises the substitution N193F.

29. A composition comprising a variant alpha-amylase and a second alpha-amylase, wherein the variant alpha-amylase has at least 70% sequence identity to SEQ ID NO: 1 and comprises the substitutions V59A+E129V+K177L+V212T+Q254S+M284V+Y268G+N293Y+T297N, and further a combination of substitutions selected from:
   R179E+W115D+D117Q+T133P;
   R179E+E188P+K279W;
   R179S+A184Q+E188P+T191N+S242Y+K279I;
   R179S+A184Q+E188P+T191N;
   S173N+R179E+E188P+H208Y+S242Y+K279I; and
   wherein the second alpha-amylase has at least 70% sequence identity to SEQ ID NO: 15 and comprises the substitutions: G48A+T49I+H68W+G107A+H156Y+A181T+E185P+N190F+A209V+Q264S+K176L+F201Y+H205Y+K213T+E255P+Q360S+D416V+R437W using SEQ ID NO: 17 for numbering.

30. The composition of claim 29, wherein the alpha-amylase further comprises a deletion selected from the group consisting of 179*+180*, 179*+181*, 179*+182*, 180*+181*, 180*+182*, and 181*+182*.

31. The composition of claim 30, wherein the alpha-amylase comprises the deletions I181*+G182*.

32. The composition of claim 30, wherein the alpha-amylase further comprises the substitution N193F.

33. The composition of claim 29, wherein the variant alpha-amylase has at least 75% sequence identity to SEQ ID NO: 1, and wherein the second alpha-amylase has at least 75% sequence identity to SEQ ID NO: 15.

34. The composition of claim 29, wherein the variant alpha-amylase has at least 80% sequence identity to SEQ ID NO: 1, and wherein the second alpha-amylase has at least 80% sequence identity to SEQ ID NO: 15.

35. The composition of claim 29, wherein the variant alpha-amylase has at least 85% sequence identity to SEQ ID NO: 1, and wherein the second alpha-amylase has at least 85% sequence identity to SEQ ID NO: 15.

36. The composition of claim 29, wherein the variant alpha-amylase has at least 90% sequence identity to SEQ ID NO: 1, and wherein the second alpha-amylase has at least 90% sequence identity to SEQ ID NO: 15.

37. The composition of claim 29, wherein the variant alpha-amylase has at least 95% sequence identity to SEQ ID NO: 1, and wherein the second alpha-amylase has at least 95% sequence identity to SEQ ID NO: 15.

* * * * *